US011180482B2

(12) United States Patent
Huang et al.

(10) Patent No.: US 11,180,482 B2
(45) Date of Patent: Nov. 23, 2021

(54) ANILINOPYRIMIDINES AS HAEMATOPOIETIC PROGENITOR KINASE 1 (HPK1) INHIBITORS

(71) Applicant: Ariad Pharmaceuticals, Inc., Cambridge, MA (US)

(72) Inventors: Wei-Sheng Huang, Cambridge, MA (US); Yun Zhang, Cambridge, MA (US); Willmen Youngsaye, Cambridge, MA (US); Xiaotian Zhu, Cambridge, MA (US); Erin Geno, Cambridge, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/465,073

(22) PCT Filed: Nov. 29, 2017

(86) PCT No.: PCT/US2017/063633

§ 371 (c)(1),
(2) Date: May 29, 2019

(87) PCT Pub. No.: WO2018/102366

PCT Pub. Date: Jun. 7, 2018

(65) Prior Publication Data

US 2019/0382379 A1 Dec. 19, 2019

Related U.S. Application Data

(60) Provisional application No. 62/428,191, filed on Nov. 30, 2016.

(51) Int. Cl.

| | |
|---|---|
| *C07D 403/12* | (2006.01) |
| *C07D 403/14* | (2006.01) |
| *C07D 239/48* | (2006.01) |
| *C07D 401/12* | (2006.01) |
| *C07D 405/14* | (2006.01) |
| *C07D 455/04* | (2006.01) |

(52) U.S. Cl.

CPC ......... *C07D 403/12* (2013.01); *C07D 239/48* (2013.01); *C07D 401/12* (2013.01); *C07D 403/14* (2013.01); *C07D 405/14* (2013.01); *C07D 455/04* (2013.01)

(58) Field of Classification Search

CPC ............................ C07D 403/12; C07D 403/14

See application file for complete search history.

(56) References Cited

U.S. PATENT DOCUMENTS

2015/0225436 A1 8/2015 Wang et al.

FOREIGN PATENT DOCUMENTS

| | | | |
|---|---|---|---|
| WO | 2015/038868 | A1 | 3/2015 |
| WO | 2015/089481 | A2 | 6/2015 |
| WO | 2015/194764 | A2 | 12/2015 |

OTHER PUBLICATIONS

Sawasdikosol et al. Immunologic Research vol. 54, pp. 262-265,2012.*

International Search Report for PCT/US2017/063633, 4 pages (dated Feb. 6, 2018).

* cited by examiner

*Primary Examiner* — Brian E McDowell

(74) *Attorney, Agent, or Firm* — Honigman LLP; Lucy X. Yang; Jonathan P. O'Brien

(57) ABSTRACT

The invention relates to HPK1 inhibitors useful in the treatment of cancers, and other serine-threonine kinase mediated diseases, having the Formula: where A, $R_1$, $R_2$, $R_3$, $R_4$, $R_5$, $R_6$, $R_{16}$, $R_{17}$, $X_1$, $X_2$, $X_3$, $X_4$, m, and n are described herein.

(I)

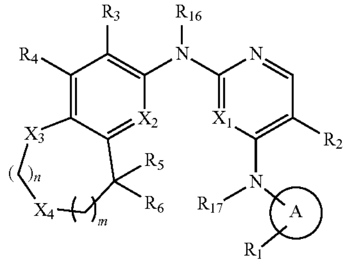

12 Claims, No Drawings

ANILINOPYRIMIDINES AS HAEMATOPOIETIC PROGENITOR KINASE 1 (HPK1) INHIBITORS

CROSS REFERENCE TO RELATED APPLICATIONS

This application is a 35 U.S.C. § 371 National Stage Application of International Application No. PCT/US2017/063633, filed Nov. 29, 2017, which claims priority to U.S. Provisional Patent Application Ser. No. 62/428,191, filed Nov. 30, 2016, the entirety of which is hereby incorporated by reference.

FIELD OF INVENTION

The present invention is directed to inhibitors of haematopoietic progenitor kinase 1 (HPK1) useful in the treatment of diseases or disorders associated with HPK1. Specifically, the invention is concerned with compounds and compositions inhibiting HPK1, methods of treating diseases or disorders associated with HPK1, and methods of synthesis of these compounds.

BACKGROUND OF THE INVENTION

Cancer immunotherapy is treatment that uses the human body's own immune system to help fight cancer. This unique approach has witnessed significant clinical successes in the treatment of a variety of tumor types in recent years, particularly with the application of immune checkpoint inhibitors and chimeric antigen T cell therapy. Two of the most investigated checkpoint blockades (i.e., CTLA4 and PD-1 inhibitors) have demonstrated remarkable antitumor activity by overcoming immunosuppressive mechanisms at the tumor site. CTLA4 blockade predominantly enhances T cell activation during the priming phase of the immune response, whereas PD-1 inhibitors appear to release exhausted but otherwise activated effector T cell populations and reduce regulatory T cell function. While these monoclonal antibody-based T cell interventions have proven to be effective, utility of this approach is limited as they can only target receptors on the cell surface. To the contrary, small-molecule T cell activators offer the opportunity to target both extracellular and intracellular immune targets including kinases. Furthermore, inhibiting immune suppressive kinases has the potential to directly activate T cells, thus bypassing checkpoint inhibitory pathways and overcoming intrinsic and acquired resistance to checkpoint receptor blockade.

Haematopoietic progenitor kinase 1 (HPK1; also known as MAP4K1) is a member of the germinal center kinase family of serine/threonine kinases and is mainly expressed by haematopoietic cells. In T cells, it is believed that HPK1 phosphorylates serine 376 of SLP76 after T cell receptor (TCR) triggers and induces the association of SLP76 with 14-3-3 proteins. Knockdown of HPK1 expression in Jurkat T cells has been shown to increase TCR-induced activation of the IL2 gene. Further, antigen-stimulated T cells from HPK1-deficient mice proliferated more vigorously and produced higher amounts of cytokines as compared to antigen-stimulated T-cells from wild-type mice. Importantly, HPK1-deficient mice developed a more severe form of experimental autoimmune encephalomyelitis (EAE), a model of multiple sclerosis. Both in vitro and in vivo, HPK1 knockout dendritic cells (DC) have demonstrated enhanced antigen presentation function. Particularly, both HPK1 knockout T cells and HPK1 knockout DCs have been implicated in tumor rejection in a murine model of lung cancer. These findings have validated HPK1 as a novel target for anti-cancer immunotherapy. Inhibition of HPK1 with small molecule inhibitors therefore has the potential to be a treatment for cancers and other disorders.

SUMMARY OF THE INVENTION

The present disclosure provides novel 2-(2,4,5-substituted)anilinopyrimidine compounds and pharmaceutically acceptable salts as effective HPK1 inhibitors and T cell activators.

A first aspect of the invention relates to compounds of Formula (I):

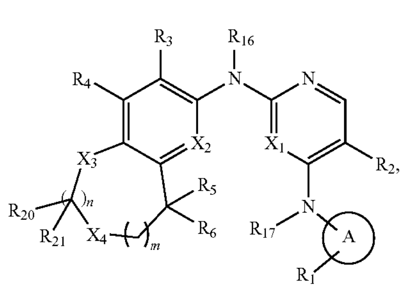

(I)

or a pharmaceutically acceptable salt, hydrate, solvate, prodrug, stereoisomer, and tautomer thereof, wherein:

A is $C_{6-10}$ aryl or 5- or 6-membered heteroaryl;

$X_1$ is N or CH;

$X_2$ is N or CH;

$X_3$ is $CR_7R_8$, NH, O, or $S(O)_q$;

$X_4$ is $NR_9$, O, $S(O)_q$ or $CR_{10}R_{11}$;

$R_1$ is $—P(O)R_{12}R_{13}$;

$R_2$ is H, D, halogen, OH, $C_{1-6}$ alkyl, $C_{2-6}$ alkenyl, $C_{2-6}$ alkynyl, $C_{1-6}$ alkoxy, $C_{6-10}$ aryl, 5- to 7-membered heteroaryl, $C_{3-7}$ cycloalkyl, 3- to 7-membered heterocycloalkyl, CN, $NO_2$, $NR_{14}R_{15}$, $C(O)NR_{14}R_{15}$, $C(O)OR_{14}$, or $NR_{14}C(O)R_{12}$, wherein the $C_{1-6}$ alkyl, $C_{2-6}$ alkenyl, $C_{2-6}$ alkynyl, $C_{1-6}$ alkoxy, $C_{6-10}$ aryl, and 5- to 7-membered heteroaryl are optionally substituted with one or more substituents independently selected from the group consisting of $C_{1-6}$ alkyl, $C_{1-6}$ haloalkyl, halogen, $NR_{14}R_{15}$, CN, $NO_2$, and OH;

$R_3$ is H, D, halogen, OH, CN, $NO_2$, $C_{1-6}$ alkyl, $C_{2-6}$ alkenyl, $C_{2-6}$ alkynyl, $C_{1-6}$ alkoxy,$C(O)NR_{14}R_{15}$, $NR_{14}C(O)R_{12}$, or $NR_{14}R_{15}$ wherein the $C_{1-6}$ alkyl, $C_{2-6}$ alkenyl, $C_{2-6}$ alkynyl,and $C_{1-6}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH;

$R_4$ is H, D, halogen, OH, CN, $NO_2$, $C_{1-6}$ alkyl, $C_{2-6}$ alkenyl, $C_{2-6}$ alkynyl, $C_{1-6}$ alkoxy, $C(O)NR_{14}R_{15}$, $NR_{14}C(O)R_{12}$, or $NR_{14}R_{15}$ wherein the $C_{1-6}$ alkyl, $C_{2-6}$ alkenyl, $C_{2-6}$ alkynyl, $C_{1-6}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_3$ and $R_4$, together with the carbon atoms to which they are attached, form a $C_{5-7}$ cycloalkyl optionally substituted with one or more $R_{18}$; or $R_3$ and $R_4$, together with the carbon atoms to which they are attached, form a 5- to 7-membered heterocycloalkyl ring optionally substituted with one or more $R_{18}$; or $R_3$ and $R_4$, together with the carbon atoms to which they are attached, form a $C_{6-10}$ aryl ring optionally substituted with one or more $R_{18}$; or $R_3$ and $R_4$, together with the carbon atoms to which they are attached, form a 5- to 7-membered heteroaryl ring optionally substituted with one or more $R_{18}$;

$R_5$ and $R_6$ are each independently H, D, $C_{1-6}$ alkyl, $C_{2-6}$ alkenyl, $C_{2-6}$ alkynyl, $C_{3-7}$ cycloalkyl, 3- to 7-membered heterocycloalkyl, $NH_2$, $C_{1-6}$ alkylamino, or $C_{1-6}$ dialkylamino, wherein the $C_{1-6}$ alkyl, $C_{2-6}$ alkenyl, $C_{2-6}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_5$ and $R_6$ together with the carbon atom to which they are attached form an oxo group; or $R_5$ and $R_6$ together with the carbon atom to which they are attached form a $C_{3-7}$ cycloalkyl; or $R_5$ and $R_6$ together with the carbon atom to which they are attached form a 3- to 7-membered heterocycloalkyl ring;

$R_7$ and $R_8$ are each independently H, D, $C_{1-6}$ alkyl, $C_{2-6}$ alkenyl, $C_{2-6}$ alkynyl, $C_{3-7}$ cycloalkyl, 3- to 7-membered heterocycloalkyl, or $NH_2$, wherein the $C_{1-6}$ alkyl, $C_{2-6}$ alkenyl, $C_{2-6}$ alkynyl, $C_{1-6}$ alkoxy, $C_{3-7}$ cycloalkyl, and heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_7$ and $R_8$, together with the carbon atom to which they are attached, form a $C_{5-7}$ cycloalkyl ring optionally substituted with one or more $R_{19}$; or $R_7$ and $R_8$, together with the carbon atom to which they are attached, form a 5- to 7-membered heterocycloalkyl ring optionally substituted with one or more $R_{19}$; or $R_7$ and $R_8$, together with the carbon atom to which they are attached, form a $C_{6-10}$ aryl ring optionally substituted with one or more $R_{19}$; or $R_7$ and $R_8$, together with the carbon atom to which they are attached, form a 5- to 7-membered heteroaryl ring optionally substituted with one or more $R_{19}$;

$R_9$ is H, D, $C_{1-6}$ alkyl, $C_{2-6}$ alkenyl, $C_{2-6}$ alkynyl, —C(O)$R_{12}$, $C_{3-7}$ cycloalkyl, or 3- to 7-membered heterocycloalkyl, wherein the $C_{1-6}$ alkyl, $C_{2-6}$ alkenyl, $C_{2-6}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH;

$R_{10}$ and $R_{11}$ are each independently H, D, $C_{1-6}$ alkyl, $C_{2-6}$ alkenyl, $C_{2-6}$ alkynyl, $NR_{14}R_{15}$, $C_{3-7}$ cycloalkyl, or 3- to 7-membered heterocycloalkyl, wherein $C_{1-6}$ alkyl, $C_{2-6}$ alkenyl, $C_{2-6}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH;

$R_{12}$ and $R_{13}$ are each independently $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-7}$ cycloalkyl, or 3- to 7-membered heterocycloalkyl; or $R_{12}$ and $R_{13}$ together with the phosphorus atom to which they are attached form a 3-8 membered heterocycloalkyl ring;

$R_{14}$ and $R_{15}$ are each independently H, D, $C_{1-6}$ alkyl, $C_{2-6}$ alkenyl, $C_{2-6}$ alkynyl, $C_{1-6}$ haloalkyl, $C_{3-7}$ cycloalkyl, or 5- to 7-membered heterocycloalkyl; or $R_{14}$ and $R_{15}$ together with the nitrogen atom to which they are attached form a 3- to 8-membered heterocycloalkyl ring optionally substituted with one or more substituents independently selected from the group consisting of $C_{1-6}$ alkyl, $C_{1-6}$ haloalkyl, $C_{1-6}$ hydroxyalkyl, halogen, $NR_{16}R_{17}$, CN, $NO_2$, and OH;

$R_{16}$ and $R_{17}$ are each independently H, D, or $C_{1-6}$ alkyl;

each $R_{18}$ is independently selected from the group consisting of halogen, OH, CN, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, C(O)$NR_{14}R_{15}$, $NR_{14}C(O)R_{12}$, and $NR_{14}R_{15}$;

each $R_{19}$ is independently selected from the group consisting of halogen, OH, CN, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, C(O)$NR_{14}R_{15}$, $NR_{14}C(O)R_{12}$, and $NR_{14}R_{15}$;

$R_{20}$ and $R_{21}$ are each independently H, D, or $C_{1-6}$ alkyl; or $R_{20}$ and $R_9$, when on adjacent atoms, together with the atoms to which they are attached form a 5- to 7-membered heterocycloalkyl ring;

each m and n is independently 0, 1, or 2, wherein the sum of m and n is 0, 1, or 2; and q is 0, 1, or 2.

A second aspect of the invention relates to a method of treating a HPK1-mediated disease or disorder. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of preventing a HPK1-mediated disease or disorder. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of inhibiting HPK1. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a disease or disorder associated with inhibiting HPK1. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of preventing a disease or disorder associated with inhibiting HPK1. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a HPK1-mediated disease or disorder comprising administering to a patient in need of a treatment for a HPK1-mediated disease or disorder an effective amount of a compound of Formula (II), or a pharmaceutically acceptable salt, hydrate, solvate, prodrug, stereoisomer, or tautomer thereof, (II)

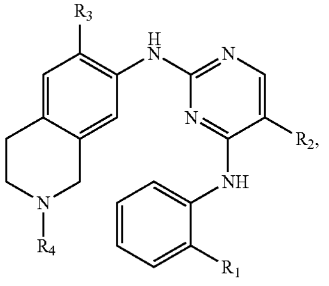

wherein:

$R_1$ is $C_{1-6}$ alkoxy, CN, $NO_2$, $C(O)NR_{14}R_{15}$, $SO_2R_{14}$, $SO_2NR_{14}R_{15}$, $C(O)R_{14}$, or $NR_{16}C(O)R_{14}$;

$R_2$ is halogen;

$R_3$ is $C_{1-6}$ alkoxy;

$R_4$ is H or $C_{1-6}$ alkyl;

$R_{14}$ and $R_{15}$ are each independently H, $C_{1-6}$ alkyl, $C_{2-6}$ alkenyl, $C_{2-6}$ alkynyl, $C_{1-6}$ haloalkyl, $C_{3-7}$ cycloalkyl, or 3- to 7-membered heterocycloalkyl; or $R_{14}$ and $R_{15}$ together with the nitrogen atom to which they are attached form a 3- to 8-membered heterocycloalkyl ring optionally substituted with one or more substituents each independently selected from the group consisting of $C_{1-6}$ alkyl, $C_{1-6}$ haloalkyl, $C_{1-6}$ hydroxyalkyl, halogen, $NR_{16}R_{17}$, CN, $NO_2$, and OH; and $R_{16}$ and $R_{17}$ are each independently H or $C_{1-6}$ alkyl.

Another aspect of the invention relates to a method of preventing a HPK1-mediated disease or disorder comprising administering to a patient in need thereof an effective amount of a compound of Formula (II), or a pharmaceutically acceptable salt, hydrate, solvate, prodrug, stereoisomer, or tautomer thereof.

Another aspect of the invention is directed to a method of inhibiting HPK1. The method involves administering to a patient in need thereof an effective amount of a compound of Formula (II), or a pharmaceutically acceptable salt, hydrate, solvate, prodrug, stereoisomer, or tautomer thereof.

Another aspect of the invention relates to a method of treating a disease or disorder associated with inhibiting HPK1. The method comprises administering to a patient in need thereof an effective amount of a compound of Formula (II), or a pharmaceutically acceptable salt, hydrate, solvate, prodrug, stereoisomer, or tautomer thereof.

Another aspect of the invention relates to a method of preventing a disease or disorder associated with inhibiting HPK1. The method comprises administering to a patient in need thereof an effective amount of a compound of Formula (II), or a pharmaceutically acceptable salt, hydrate, solvate, prodrug, stereoisomer, or tautomer thereof.

Another aspect of the invention relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating cancer. The method comprises administering to a patient in need thereof an effective amount of a compound of Formula (II), or a pharmaceutically acceptable salt, hydrate, solvate, prodrug, stereoisomer, or tautomer thereof.

Another aspect of the invention is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the invention is directed to pharmaceutical compositions comprising a compound of Formula (II), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with inhibiting HPK1.

Another aspect of the present invention relates to a compound of Formula (II), or a pharmaceutically acceptable salt, hydrate, solvate, prodrug, stereoisomer, or tautomer thereof, for use in the manufacture of a medicament for treating a disease associated with inhibiting HPK1.

Another aspect of the present invention relates to a compound of Formula (I), or a pharmaceutically acceptable salt, hydrate, solvate, prodrug, stereoisomer, or tautomer thereof, for use in the manufacture of a medicament for preventing a disease associated with inhibiting HPK1.

Another aspect of the present invention relates to a compound of Formula (II), or a pharmaceutically acceptable salt, hydrate, solvate, prodrug, stereoisomer, or tautomer thereof, for use in the manufacture of a medicament for preventing a disease associated with inhibiting HPK1.

Another aspect of the present invention relates to the use of a compound of Formula (I), or a pharmaceutically acceptable salt, hydrate, solvate, prodrug, stereoisomer, or tautomer thereof, in the treatment of a disease associated with inhibiting HPK1.

Another aspect of the present invention relates to the use of a compound of Formula (II), or a pharmaceutically acceptable salt, hydrate, solvate, prodrug, stereoisomer, or tautomer thereof, in the treatment of a disease associated with inhibiting HPK1.

Another aspect of the present invention relates to the use of a compound of Formula (I), or a pharmaceutically acceptable salt, hydrate, solvate, prodrug, stereoisomer, or tautomer thereof, in the prevention of a disease associated with inhibiting HPK1.

Another aspect of the present invention relates to the use of a compound of Formula (II), or a pharmaceutically acceptable salt, hydrate, solvate, prodrug, stereoisomer, or tautomer thereof, in the prevention of a disease associated with inhibiting HPK1.

The present invention further provides methods of treating or preventing a disease or disorder associated with modulation of HPK1 including, cancer, metastasis, inflammation and auto-immune pathogenesis, comprising administering to a patient suffering from at least one of said diseases or disorder a compound of Formula (I), or a pharmaceutically acceptable salt, hydrate, solvate, prodrug, stereoisomer, or tautomer thereof.

The present invention provides inhibitors of HPK1 that are therapeutic agents in the treatment of diseases such as cancer, metastasis, inflammation and auto-immune pathogenesis.

The present disclosure provides agents with novel mechanisms of action toward HPK1 enzymes in the treatment of various types of diseases including cancer, metastasis, inflammation and auto-immune pathogenesis. Ultimately the present invention provides the medical community with a novel pharmacological strategy for the treatment of diseases and disorders associated with HPK1.

DETAILED DESCRIPTION OF THE INVENTION

The present invention relates to compounds and compositions that are capable of inhibiting the activity of HPK1. The invention features methods of treating, preventing or ameliorating a disease or disorder in which HPK1 plays a role by administering to a patient in need thereof a therapeutically effective amount of a compound of Formula (I), or a pharmaceutically acceptable salt, hydrate, solvate, prodrug, stereoisomer, or tautomer thereof. The invention also features methods of treating, preventing or ameliorating a disease or disorder in which HPK1 plays a role by administering to a patient in need thereof a therapeutically effective amount of a compound of Formula (II), or a pharmaceutically acceptable salt, hydrate, solvate, prodrug, stereoisomer, or tautomer thereof. The methods of the present invention can be used in the treatment of a variety of HPK1 dependent diseases and disorders by inhibiting the activity of HPK1 enzymes. Inhibition of HPK1 provides a novel approach to the treatment, prevention, or amelioration of diseases including, but not limited to, cancer and metastasis.

In a first aspect of the invention, the compounds of Formula (I) are described:

(I)

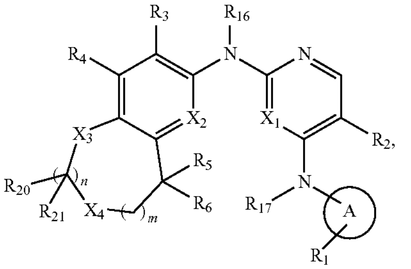

and pharmaceutically acceptable salts, hydrates, solvates, prodrugs, stereoisomers, and tautomers thereof, wherein A, $R_1$, $R_2$, $R_3$, $R_4$, $R_5$, $R_6$, $R_{16}$, $R_{17}$, $R_{20}$, $R_{21}$, $X_1$, $X_2$, $X_3$, $X_4$, m, and n are as described herein above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —$CH_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)$(OH)_2$, —OC(O)($C_1$-$C_6$) alkyl, —C(O)($C_1$-$C_6$)alkyl, —OC(O)O($C_1$-$C_6$) alkyl, —$NH_2$, —NH(($C_1$-$C_6$) alkyl), —N(($C_1$-$C_6$) $alkyl)_2$, —NHC(O)($C_1$-$C_6$) alkyl, —C(O)NH($C_1$-$C_6$) alkyl, —$S(O)_2$($C_1$-$C_6$) alkyl, —S(O)NH($C_1$-$C_6$) alkyl, and S(O)N(($C_1$-$C_6$) $alkyl)_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, $NH_2$, NH(($C_1$-$C_6$) alkyl), N(($C_1$-$C_6$) $alkyl)_2$, —$S(O)_2$—($C_1$-$C_6$) alkyl, —S(O)NH($C_1$-$C_6$) alkyl, and S(O)N(($C_1$-$C_6$) $alkyl)_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d] thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or “halo” refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

“Alkoxy” refers to a straight or branched chain saturated hydrocarbon containing 1-12 carbon atoms containing a terminal “O” in the chain, i.e., —O(alkyl). Examples of alkoxy groups include, without limitation, methoxy, ethoxy, propoxy, butoxy, t-butoxy, or pentoxy groups.

“Alkenyl” refers to a straight or branched chain unsaturated hydrocarbon containing 2-12 carbon atoms. The “alkenyl” group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

“Alkynyl” refers to a straight or branched chain unsaturated hydrocarbon containing 2-12 carbon atoms. The “alkynyl” group contains at least one triple bond in the chain. Examples of alkenyl groups include ethynyl, propargyl, n-butynyl, iso-butynyl, pentynyl, or hexynyl. An alkynyl group can be unsubstituted or substituted.

“Cycloalkyl” means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

“Heterocyclyl” or “heterocycloalkyl” monocyclic rings containing carbon and heteroatoms taken from oxygen, nitrogen, or sulfur and wherein there is not delocalized π electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term “hydroxyalkyl” means an alkyl group as defined above, where the alkyl group is substituted with one or more —OH groups. Examples of hydroxyalkyl groups include $HO—CH_2—$, $HO—CH_2—CH_2—$ and $CH_3—CH(OH)—$.

The term “haloalkyl” as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term “haloalkoxy” as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term “amine” as used herein refers to primary ($R—NH_2$, $R\neq H$), secondary ($R_2—NH$, $R_2\neq H$) and tertiary ($R_3—N$, $R\neq H$) amines. A substituted amine is intended to mean an amine where at least one of the hydrogen atoms has been replaced by the substituent.

The term “amino” as used herein means a substituent containing at least one nitrogen atom. Specifically, $NH_2$, —NH(alkyl) or alkylamino, $—N(alkyl)_2$ or dialkylamino, amide-, carbamide-, urea, and sulfamide substituents are included in the term “amino”.

The term “alkylamino” as used herein refers to an amino or $NH_2$ group where one of the hydrogens has been replaced with an alkyl group, as defined herein above, i.e., —NH(alkyl). Example of alkylamino groups include, but are not limited to, methylamino (i.e., $—NH(CH_3)$), ethylamino, propylamino, iso-propylamino, n-butylamino, sec-butylamino, tert-butylamino, etc.

The term “dialkylamino” as used herein refers to an amino or $NH_2$ group where both of the hydrogens have been replaced with alkyl groups, as defined herein above, i.e., $—N(alkyl)_2$. The alkyl groups on the amino group can be the same or different alkyl groups. Example of alkylamino groups include, but are not limited to, dimethylamino (i.e., $—N(CH_3)_2$), diethylamino, dipropylamino, diiso-propylamino, di-n-butylamino, di-sec-butylamino, di-tert-butylamino, methyl(ethyl)amino, methyl(butylamino), etc.

The term “oxo” as used herein refers to an “═O” group.

The term “solvate” refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

As used herein, "treating" or "treat" describes the management and care of a patient for the purpose of reversing, inhibiting, or combating a disease, condition, or disorder and includes the administration of a compound of the present disclosure (i.e., a compound of Formula (I) or Formula (II)), or a pharmaceutically acceptable salt, prodrug, metabolite, polymorph or solvate thereof, to reverse the disease, condition, or disorder, eliminate the disease, condition, or disorder, or inhibit the process of the disease, condition, or disorder.

A compound of the present disclosure (i.e., a compound of Formula (I) or Formula (II)), or a pharmaceutically acceptable salt, prodrug, metabolite, polymorph or solvate thereof, can also be used to prevent a disease, condition, or disorder or one or more symptoms of such disease, condition, or disorder. As used herein, "preventing" or "prevent" describes reducing or eliminating the onset of the symptoms or complications of the disease, condition, or disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting HPK1, which are useful for the treatment of diseases and disorders associated with modulation of a HPK1 enzyme. The invention further relates to compounds, or pharmaceutically acceptable salts, hydrates, solvates, prodrugs, stereoisomers, or tautomers thereof, which are useful for inhibiting HPK1.

In one embodiment, the compounds of Formula (I) have the structure of Formula (Ia):

(Ia)

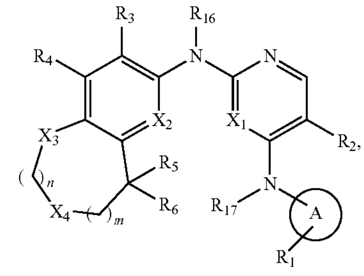

and pharmaceutically acceptable salts, hydrates, solvates, prodrugs, stereoisomers, and tautomers thereof.

In another embodiment, the compounds of Formula (I) have the structure of Formula (Ib):

(Ib)

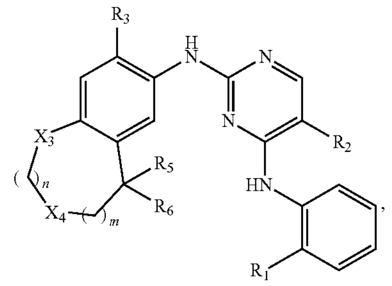

and pharmaceutically acceptable salts, hydrates, solvates, prodrugs, stereoisomers, and tautomers thereof.

In another embodiment, the compounds of Formula (I) have the structure of Formula (Ic):

(Ic)

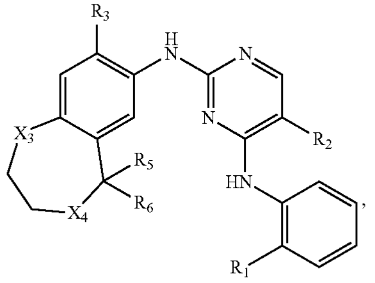

and pharmaceutically acceptable salts, hydrates, solvates, prodrugs, stereoisomers, and tautomers thereof.

In another embodiment, the compounds of Formula (I) have the structure of Formula (Id):

(Id)

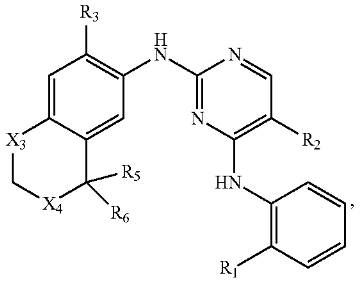

and pharmaceutically acceptable salts, hydrates, solvates, prodrugs, stereoisomers, and tautomers thereof.

In another embodiment, the compounds of Formula (I) have the structure of Formula (Ie):

(Ie)

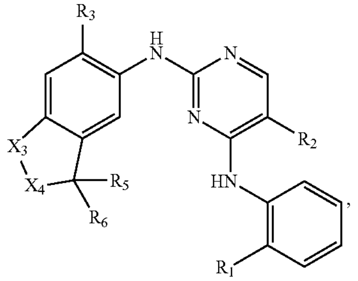

and pharmaceutically acceptable salts, hydrates, solvates, prodrugs, stereoisomers, and tautomers thereof.

In another embodiment, the compounds of Formula (I) have the structure of Formula (If):

(If)

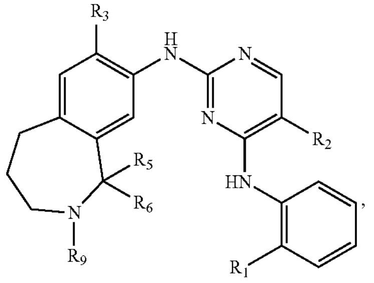

and pharmaceutically acceptable salts, hydrates, solvates, prodrugs, stereoisomers, and tautomers thereof.

In another embodiment, the compounds of Formula (I) have the structure of Formula (Ig):

(Ig)

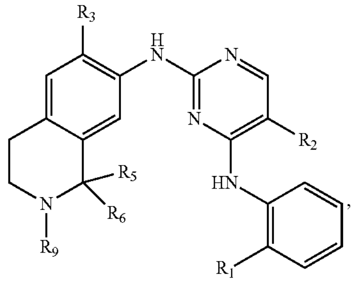

and pharmaceutically acceptable salts, hydrates, solvates, prodrugs, stereoisomers, and tautomers thereof.

In another embodiment, the compounds of Formula (I) have the structure of Formula (Ih):

(Ih)

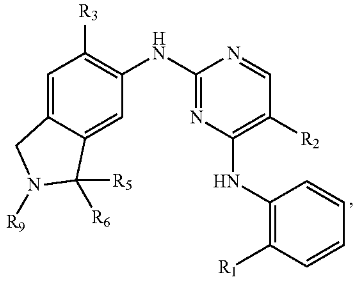

and pharmaceutically acceptable salts, hydrates, solvates, prodrugs, stereoisomers, and tautomers thereof.

In another embodiment, the compounds of Formula (I) have the structure of Formula (Ii):

(Ii)

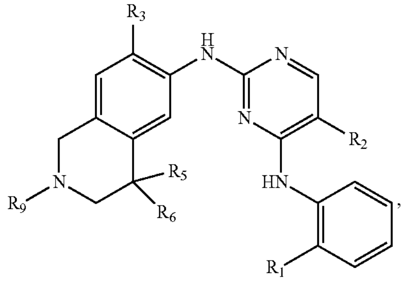

and pharmaceutically acceptable salts, hydrates, solvates, prodrugs, stereoisomers, and tautomers thereof.

In another embodiment, the compounds of Formula (I) have the structure of Formula (Ij):

(Ij)

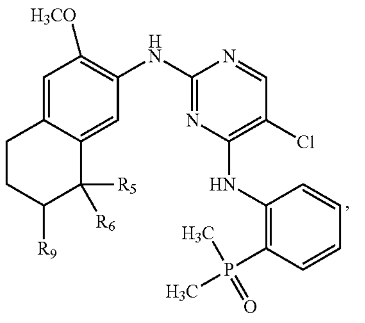

and pharmaceutically acceptable salts, hydrates, solvates, prodrugs, stereoisomers, and tautomers thereof.

In another embodiment, the compounds of Formula (I) have the structure of Formula (Ik):

(Ik)

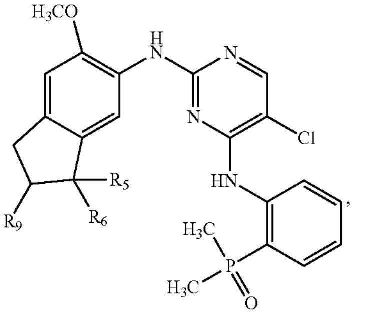

and pharmaceutically acceptable salts, hydrates, solvates, prodrugs, stereoisomers, and tautomers thereof.

In some embodiments of the formulae above:

A is $C_{6-10}$ aryl or 5- or 6-membered heteroaryl;

$X_1$ is N or CH;

$X_2$ is N or CH;

$X_3$ is $CR_7R_8$, NH, O, or $S(O)_q$;

$X_4$ is $NR_9$, O, $S(O)_q$ or $CR_{10}R_{11}$;

$R_1$ is —$P(O)R_{12}R_{13}$;

$R_2$ is H, D, halogen, OH, $C_{1-6}$ alkyl, $C_{2-6}$ alkenyl, $C_{2-6}$ alkynyl, $C_{1-6}$ alkoxy, $C_{6-10}$ aryl, 5- to 7-membered heteroaryl, $C_{3-7}$ cycloalkyl, 3- to 7-membered heterocycloalkyl, CN, $NO_2$, $NR_{14}R_{15}$, $C(O)NR_{14}R_{15}$, $C(O)OR_{14}$, or $NR_{14}C(O)R_{12}$, wherein the $C_{1-6}$ alkyl, $C_{2-6}$ alkenyl, $C_{2-6}$ alkynyl, $C_{1-6}$ alkoxy, $C_{6-10}$ aryl, and 5- to 7-membered heteroaryl are optionally substituted with one or more substituents independently selected from the group consisting of $C_{1-6}$ alkyl, $C_{1-6}$ haloalkyl, halogen, $NR_{14}R_{15}$, CN, $NO_2$, and OH;

$R_3$ is H, halogen, OH, CN, $NO_2$, $C_{1-6}$ alkyl, $C_{2-6}$ alkenyl, $C_{2-6}$ alkynyl, $C_{1-6}$ alkoxy,$C(O)NR_{14}R_{15}$, $NR_{14}C(O)R_{12}$, or $NR_{14}R_{15}$ wherein the $C_{1-6}$ alkyl, $C_{2-6}$ alkenyl, $C_{2-6}$ alkynyl, and $C_{1-6}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH;

$R_4$ is H, halogen, OH, CN, $NO_2$, $C_{1-6}$ alkyl, $C_{2-6}$ alkenyl, $C_{2-6}$ alkynyl, $C_{1-6}$ alkoxy, $C(O)NR_{14}R_{15}$, $NR_{14}C(O)R_{12}$, or $NR_{14}R_{15}$ wherein the $C_{1-6}$ alkyl, $C_{2-6}$ alkenyl, $C_{2-6}$ alkynyl, $C_{1-6}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_3$ and $R_4$, together with the carbon atoms to which they are attached, form a $C_{5-7}$ cycloalkyl optionally substituted with one or more $R_{18}$; or $R_3$ and $R_4$, together with the carbon atoms to which they are attached, form a 5- to 7-membered heterocycloalkyl ring optionally substituted with one or more $R_{18}$; or $R_3$ and $R_4$, together with the carbon atoms to which they are attached, form a $C_{6-10}$ aryl ring optionally substituted with one or more $R_{18}$; or $R_3$ and $R_4$, together with the carbon atoms to which they are attached, form a 5- to 7-membered heteroaryl ring optionally substituted with one or more $R_{18}$;

$R_5$ and $R_6$ are each independently H, D, $C_{1-6}$ alkyl, $C_{2-6}$ alkenyl, $C_{2-6}$ alkynyl, $C_{3-7}$ cycloalkyl, 3- to 7-membered heterocycloalkyl, $NH_2$, $C_{1-6}$ alkylamino, or $C_{1-6}$ dialkylamino, wherein the $C_{1-6}$ alkyl, $C_{2-6}$ alkenyl, $C_{2-6}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_5$ and $R_6$ together with the carbon atom to which they are attached form an oxo group; or $R_5$ and $R_6$ together with the carbon atom to which they are attached form a $C_{3-7}$ cycloalkyl; or $R_5$ and $R_6$ together with the carbon atom to which they are attached form a 3- to 7-membered heterocycloalkyl ring;

$R_7$ and $R_8$ are each independently H, D, $C_{1-6}$ alkyl, $C_{2-6}$ alkenyl, $C_{2-6}$ alkynyl, $C_{3-7}$ cycloalkyl, 3- to 7-membered heterocycloalkyl, or $NH_2$, wherein the $C_{1-6}$ alkyl, $C_{2-6}$ alkenyl, $C_{2-6}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_7$ and $R_8$, together with the carbon atom to which they are attached, form a $C_{5-7}$ cycloalkyl ring optionally substituted with one or more $R_{19}$; or $R_7$ and $R_8$, together with the carbon atom to which they are attached, form a 5- to 7-membered heterocycloalkyl ring optionally substituted with one or more $R_{19}$; or $R_7$ and $R_8$, together with the carbon atom to which they are attached, form a $C_{6-10}$ aryl ring optionally substituted with one or more $R_{19}$; or $R_7$ and $R_8$, together with the carbon atom to which they are attached, form a 5- to 7-membered heteroaryl ring optionally substituted with one or more $R_{19}$;

$R_9$ is H, $C_{1-6}$ alkyl, $C_{2-6}$ alkenyl, $C_{2-6}$ alkynyl, —$C(O)R_{12}$, $C_{3-7}$ cycloalkyl, or 3- to 7-membered heterocycloalkyl, wherein the $C_{1-6}$ alkyl, $C_{2-6}$ alkenyl, $C_{2-6}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH;

$R_{10}$ and $R_{11}$ are each independently H, $C_{1-6}$ alkyl, $C_{2-6}$ alkenyl, $C_{2-6}$ alkynyl, $NR_{14}R_{15}$, $C_{3-7}$ cycloalkyl, or 3- to 7-membered heterocycloalkyl, wherein $C_{1-6}$ alkyl, $C_{2-6}$ alkenyl, $C_{2-6}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH;

$R_{12}$ and $R_{13}$ are each independently $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-7}$ cycloalkyl, or 3- to 7-membered heterocycloalkyl; or $R_{12}$ and $R_{13}$ together with the phosphorus atom to which they are attached form a 3-8 membered heterocycloalkyl ring;

$R_{14}$ and $R_{15}$ are each independently H, $C_{1-6}$ alkyl, $C_{2-6}$ alkenyl, $C_{2-6}$ alkynyl, $C_{1-6}$ haloalkyl, $C_{3-7}$ cycloalkyl, or 5- to 7-membered heterocycloalkyl; or $R_{14}$ and $R_{15}$ together with the nitrogen atom to which they are attached form a 3- to 8-membered heterocycloalkyl ring optionally substituted with one or more substituents independently selected from the group consisting of $C_{1-6}$ alkyl, $C_{1-6}$ haloalkyl, $C_{1-6}$ hydroxyalkyl, halogen, $NR_{16}R_{17}$, CN, $NO_2$, and OH;

$R_{16}$ and $R_{17}$ are each independently H or $C_{1-6}$ alkyl;

each $R_{18}$ is independently selected from the group consisting of halogen, OH, CN, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C(O)NR_{14}R_{15}$, $NR_{14}C(O)R_{12}$, and $NR_{14}R_{15}$;

each $R_{19}$ is independently selected from the group consisting of halogen, OH, CN, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C(O)NR_{14}R_{15}$, $NR_{14}C(O)R_{12}$, and $NR_{14}R_{15}$;

$R_{20}$ and $R_{21}$ are each independently H or $C_{1-6}$ alkyl; or $R_{20}$ and $R_9$, when on adjacent atoms, together with the atoms to which they are attached form a 5- to 7-membered heterocycloalkyl ring;

each m and n is independently 0, 1, or 2, wherein the sum of m and n is 0, 1, or 2; and q is 0, 1, or 2.

In some embodiments of the formulae above:

$X_1$ is N or CH;

$X_2$ is N or CH;

$X_3$ is $CR_7R_8$, NH, O, or $S(O)_q$;

$X_4$ is $NR_9$, O, $S(O)_q$ or $CR_{10}R_{11}$;

$R_1$ is $—P(O)R_{12}R_{13}$;

$R_2$ is H, halogen, OH, $C_{1-6}$ alkyl, $C_{2-6}$ alkenyl, $C_{2-6}$ alkynyl, $C_{1-6}$ alkoxy, $C_{6-10}$ aryl, 5- to 7-membered heteroaryl, $C_{3-7}$ cycloalkyl, 3- to 7-membered heterocycloalkyl, CN, $NO_2$, $NR_{14}R_{15}$, $C(O)NR_{14}R_{15}$, $C(O)OR_{14}$, or $NR_{14}C(O)R_{12}$, wherein the $C_{1-6}$ alkyl, $C_{2-6}$ alkenyl, $C_{2-6}$ alkynyl, $C_{1-6}$ alkoxy, $C_{6-10}$ aryl, and 5- to 7-membered heteroaryl are optionally substituted with one or more substituents independently selected from the group consisting of $C_{1-6}$ alkyl, $C_{1-6}$ haloalkyl, halogen, $NR_{14}R_{15}$, CN, $NO_2$, and OH;

$R_3$ is H, halogen, OH, CN, $NO_2$, $C_{1-6}$ alkyl, $C_{2-6}$ alkenyl, $C_{2-6}$ alkynyl, $C_{1-6}$ alkoxy, $C(O)NR_{14}R_{15}$, $NR_{14}C(O)R_{12}$, or $NR_{14}R_{15}$ wherein the $C_{1-6}$ alkyl, $C_{2-6}$ alkenyl, $C_{2-6}$ alkynyl, and $C_{1-6}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH;

$R_4$ is H, halogen, OH, CN, $NO_2$, $C_{1-6}$ alkyl, $C_{2-6}$ alkenyl, $C_{2-6}$ alkynyl, $C_{1-6}$ alkoxy, $C(O)NR_{14}R_{15}$, $NR_{14}C(O)R_{12}$, or $NR_{14}R_{15}$ wherein the $C_{1-6}$ alkyl, $C_{2-6}$ alkenyl, $C_{2-6}$ alkynyl, $C_{1-6}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_3$ and $R_4$, together with the carbon atoms to which they are attached, form a $C_{5-7}$ cycloalkyl optionally substituted with one or more $R_{18}$; or $R_3$ and $R_4$, together with the carbon atoms to which they are attached, form a 5- to 7-membered heterocycloalkyl ring optionally substituted with one or more $R_{18}$; or $R_3$ and $R_4$, together with the carbon atoms to which they are attached, form a $C_{6-10}$ aryl ring optionally substituted with one or more $R_{18}$; or $R_3$ and $R_4$, together with the carbon atoms to which they are attached, form a 5- to 7-membered heteroaryl ring optionally substituted with one or more $R_{18}$;

$R_5$ and $R_6$ are each independently H, D, $C_{1-6}$ alkyl, $C_{2-6}$ alkenyl, $C_{2-6}$ alkynyl, $C_{3-7}$ cycloalkyl, 3- to 7-membered heterocycloalkyl, $NH_2$, $C_{1-6}$ alkylamino, or $C_{1-6}$ dialkylamino, wherein the $C_{1-6}$ alkyl, $C_{2-6}$ alkenyl, $C_{2-6}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_5$ and $R_6$ together with the carbon atom to which they are attached form an oxo group; or $R_5$ and $R_6$ together with the carbon atom to which they are attached form a $C_{3-7}$ cycloalkyl; or $R_5$ and $R_6$ together with the carbon atom to which they are attached form a 3- to 7-membered heterocycloalkyl ring;

$R_7$ and $R_8$ are each independently H, D, $C_{1-6}$ alkyl, $C_{2-6}$ alkenyl, $C_{2-6}$ alkynyl, $C_{3-7}$ cycloalkyl, 3- to 7-membered heterocycloalkyl, or $NH_2$, wherein the $C_{1-6}$ alkyl, $C_{2-6}$ alkenyl, $C_{2-6}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_7$ and $R_8$, together with the carbon atom to which they are attached, form a $C_{5-7}$ cycloalkyl ring optionally substituted with one or more $R_{19}$; or $R_7$ and $R_8$, together with the carbon atom to which they are attached, form a 5- to 7-membered heterocycloalkyl ring optionally substituted with one or more $R_{19}$; or $R_7$ and $R_8$, together with the carbon atom to which they are attached, form a $C_{6-10}$ aryl ring optionally substituted with one or more $R_{19}$; or $R_7$ and $R_8$, together with the carbon atom to which they are attached, form a 5- to 7-membered heteroaryl ring optionally substituted with one or more $R_{19}$;

$R_9$ is H, $C_{1-6}$ alkyl, $C_{2-6}$ alkenyl, $C_{2-6}$ alkynyl, $—C(O)R_{12}$, $C_{3-7}$ cycloalkyl, or 3- to 7-membered heterocycloalkyl, wherein the $C_{1-6}$ alkyl, $C_{2-6}$ alkenyl, $C_{2-6}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH;

$R_{10}$ and $R_{11}$ are each independently H, $C_{1-6}$ alkyl, $C_{2-6}$ alkenyl, $C_{2-6}$ alkynyl, $NR_{14}R_{15}$,$C_{3-7}$ cycloalkyl, or 3- to 7-membered heterocycloalkyl, wherein $C_{1-6}$ alkyl, $C_{2-6}$ alkenyl, $C_{2-6}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH;

$R_{12}$ and $R_{13}$ are each independently $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-7}$ cycloalkyl, or 3- to 7-membered heterocycloalkyl; or $R_{12}$ and $R_{13}$ together with the phosphorus atom to which they are attached form a 3-8 membered heterocycloalkyl ring;

$R_{14}$ and $R_{15}$ are each independently H, $C_{1-6}$ alkyl, $C_{2-6}$ alkenyl, $C_{2-6}$ alkynyl, $C_{1-6}$ haloalkyl, $C_{3-7}$ cycloalkyl, or 5- to 7-membered heterocycloalkyl; or $R_{14}$ and $R_{15}$ together with the nitrogen atom to which they are attached form a 3- to 8-membered heterocycloalkyl ring optionally substituted with one or more substituents independently selected from the group consisting of $C_{1-6}$ alkyl, $C_{1-6}$ haloalkyl, $C_{1-6}$ hydroxyalkyl, halogen, $NR_{16}R_{17}$, CN, $NO_2$, and OH;

$R_{16}$ and $R_{17}$ are each independently H or $C_{1-6}$ alkyl;

each $R_{18}$ is independently selected from the group consisting of halogen, OH, CN, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, C(O)$NR_{14}R_{15}$, $NR_{14}C(O)R_{12}$, and $NR_{14}R_{15}$;

each $R_{19}$ is independently selected from the group consisting of halogen, OH, CN, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, C(O)$NR_{14}R_{15}$, $NR_{14}C(O)R_{12}$, and $NR_{14}R_{15}$;

each m and n is independently 0, 1, or 2, wherein the sum of m and n is 0, 1, or 2; and q is 0, 1, or 2.

In some embodiments of the Formulae above, A is $C_{6-10}$ aryl. In another embodiment, A is 5- or 6-membered heteroaryl. In yet another embodiment, A is 5-membered heteroaryl. In another embodiment, A is 6-membered heteroaryl. In yet another embodiment, A is phenyl.

In some embodiments of the Formulae above, $X_1$ is N. In another embodiment, $X_1$ is CH.

In some embodiments of the Formulae above, $X_2$ is N. In another embodiment, $X_2$ is CH.

In some embodiments of the Formulae above, $X_3$ is $CR_7R_8$, NH, or O. In another embodiment, $X_3$ is NH, O, or $S(O)_q$. In yet another embodiment, $X_3$ is $CR_7R_8$, O, or $S(O)_q$. In another embodiment, $X_3$ is $CR_7R_8$, NH, or $S(O)_q$. In yet another embodiment, $X_3$ is $CR_7R_8$ or NH. In another embodiment, $X_3$ is $CR_7R_8$ or O. In yet another embodiment, $X_3$ is $CR_7R_8$ or $S(O)_q$. In another embodiment, $X_3$ is NH or O. In yet another embodiment, $X_3$ is NH or $S(O)_q$. In another embodiment, $X_3$ is O or $S(O)_q$. In yet another embodiment, $X_3$ is $CR_7R_8$.

In some embodiments of the Formulae above, $X_4$ is $NR_9$, O, or $S(O)_q$. In another embodiment, $X_4$ is O, $S(O)_q$ or $CR_{10}R_{11}$. In yet another embodiment, $X_4$ is $NR_9$, $S(O)_q$ or $CR_{10}R_{11}$. In another embodiment, $X_4$ is $NR_9$, O, or $CR_{10}R_{11}$. In yet another embodiment, $X_4$ is $NR_9$ or O. In another embodiment, $X_4$ is O or $S(O)_q$. In yet another embodiment, $X_4$ is $S(O)_q$ or $CR_{10}R_{11}$. In another embodiment, $X_4$ is $NR_9$ or $S(O)_q$. In yet another embodiment, $X_4$ is $NR_9$ or $CR_{10}R_{11}$. In another embodiment, $X_4$ is O or $CR_{10}R_{11}$. In yet another embodiment, $X_4$ is $NR_9$. In another embodiment, $X_4$ is $CR_{10}R_{11}$.

In some embodiments of the Formulae above, $R_2$ is H, halogen, OH, $C_{1-4}$ alkyl, $C_{2-4}$ alkenyl, $C_{2-4}$ alkynyl, $C_{1-4}$ alkoxy, $C_{6-10}$ aryl, 5- to 7-membered heteroaryl, $C_{3-7}$ cycloalkyl, 3- to 7-membered heterocycloalkyl, CN, $NO_2$, $NR_{14}R_{15}$, C(O)$NR_{14}R_{15}$, C(O)$OR_{14}$,or $NR_{14}C(O)R_{12}$, wherein the $C_{1-4}$ alkyl, $C_{2-4}$ alkenyl, $C_{2-4}$ alkynyl, $C_{1-4}$ alkoxy, $C_{6-10}$ aryl, and 5- to 7-membered heteroaryl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_2$ is halogen, OH, $C_{1-4}$ alkyl, $C_{2-4}$ alkenyl, $C_{2-4}$ alkynyl, $C_{1-4}$ alkoxy, $C_{6-10}$ aryl, 5- to 7-membered heteroaryl, $C_{3-7}$ cycloalkyl, 3- to 7-membered heterocycloalkyl, CN, $NO_2$, $NR_{14}R_{15}$, C(O)$NR_{14}R_{15}$, C(O)$OR_{14}$, or $NR_{14}C(O)R_{12}$, wherein the $C_{1-4}$ alkyl, $C_{2-4}$ alkenyl, $C_{2-4}$ alkynyl, $C_{1-4}$ alkoxy, $C_{6-10}$ aryl, and 5- to 7-membered heteroaryl are optionally substituted with one or more substituents independently selected from the group consisting of $C_{1-6}$ alkyl, $C_{1-6}$ haloalkyl, halogen, $NR_{14}R_{15}$, CN, $NO_2$, and OH.

In another embodiment, $R_2$ is H, halogen, $C_{1-4}$ alkyl, $C_{2-4}$ alkenyl, $C_{1-4}$ alkoxy, $C_{6-10}$ aryl, or 5- to 7-membered heteroaryl, wherein the $C_{1-4}$ alkyl, $C_{2-4}$ alkenyl, $C_{1-4}$ alkoxy, $C_{6-10}$ aryl, and 5- to 7-membered heteroaryl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_2$ is halogen, $C_{1-4}$ alkyl, $C_{2-4}$ alkenyl, $C_{1-4}$ alkoxy, $C_{6-10}$ aryl, or 5- to 7-membered heteroaryl, wherein the $C_{1-4}$ alkyl, $C_{2-4}$ alkenyl, $C_{1-4}$ alkoxy, $C_{6-10}$ aryl, and 5- to 7-membered heteroaryl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_2$ is H, halogen, $C_{1-4}$ alkyl, $C_{2-4}$ alkenyl, $C_{1-4}$ alkoxy, or 5- to 7-membered heteroaryl, wherein the $C_{1-4}$alkyl, $C_{2-4}$ alkenyl, $C_{1-4}$ alkoxy, and 5- to 7-membered heteroaryl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_2$ is H, halogen, $C_{1-4}$ alkyl, $C_{2-4}$ alkenyl, $C_{1-4}$ alkoxy, or 5- to 7-membered heteroaryl, wherein the $C_{1-4}$ alkyl, is optionally substituted with one or more halogen. In another embodiment, $R_2$ is halogen. In another embodiment, $R_2$ is F, Cl or Br. In another embodiment, $R_2$ is Cl.

In some embodiments of the Formulae above, $R_3$ is H, halogen, OH, CN, $NO_2$, $C_{1-4}$ alkyl, $C_{2-4}$ alkenyl, $C_{2-4}$ alkynyl, $C_{1-4}$ alkoxy, C(O)$NR_{14}R_{15}$, $NR_{14}C(O)R_{12}$, or $NR_{14}R_{15}$ wherein the $C_{1-4}$ alkyl, $C_{2-4}$ alkenyl, $C_{2-4}$ alkynyl, and $C_{1-4}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_3$ is halogen, OH, CN, $NO_2$, $C_{1-4}$ alkyl, $C_{2-4}$ alkenyl, $C_{2-4}$ alkynyl, $C_{1-4}$ alkoxy, C(O)$NR_{14}R_{15}$, $NR_{14}C(O)R_{12}$, or $NR_{14}R_{15}$ wherein the $C_{1-4}$ alkyl, $C_{2-4}$ alkenyl, $C_{2-4}$ alkynyl, and $C_{1-4}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_3$ is H, halogen, $C_{1-4}$ alkyl, $C_{2-4}$ alkenyl, or $C_{1-4}$ alkoxy, wherein the $C_{1-4}$ alkyl, $C_{2-4}$ alkenyl, and $C_{1-4}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_3$ is H, halogen, $C_{1-4}$ alkyl, $C_{2-4}$ alkenyl, or $C_{1-4}$ alkoxy. In another embodiment, $R_3$ is H, halogen, $C_{1-3}$ alkyl, $C_{2-3}$ alkenyl, or $C_{1-3}$ alkoxy.

In some embodiments of the Formulae above, $R_4$ is H, halogen, OH, CN, $NO_2$, $C_{1-4}$ alkyl, $C_{2-4}$ alkenyl, $C_{2-4}$ alkynyl, $C_{1-4}$ alkoxy, C(O)$NR_{14}R_{15}$, $NR_{14}C(O)R_{12}$, or $NR_{14}R_{15}$, wherein the $C_{1-4}$ alkyl, $C_{2-4}$ alkenyl, $C_{2-4}$ alkynyl, $C_{1-4}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_4$ is halogen, OH, CN, $NO_2$, $C_{1-4}$ alkyl, $C_{2-4}$ alkenyl, $C_{2-4}$ alkynyl, $C_{1-4}$ alkoxy, C(O)

$NR_{14}R_{15}$, $NR_{14}C(O)R_{12}$, or $NR_{14}R_{15}$, wherein the $C_{1-4}$ alkyl, $C_{2-4}$ alkenyl, $C_{2-4}$ alkynyl, $C_{1-4}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_4$ is H, halogen, $C_{1-4}$ alkyl, $C_{2-4}$ alkenyl, $C_{1-4}$ alkoxy, $C(O)NR_{14}R_{15}$, $NR_{14}C(O)R_{12}$, or $NR_{14}R_{15}$, wherein the $C_{1-4}$ alkyl, $C_{2-4}$ alkenyl, $C_{1-4}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_4$ is H, halogen, $C_{1-4}$ alkyl, $C_{1-4}$ alkoxy, $C(O)NR_{14}R_{15}$, $NR_{14}C(O)R_{12}$, or $NR_{14}R_{15}$, wherein the $C_{1-4}$ alkyl, $C_{1-4}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_4$ is H, halogen, $C_{1-4}$ alkyl, or $NR_{14}R_{15}$, wherein the $C_{1-4}$ alkyl is optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_4$ is H, halogen, or $NR_{14}R_{15}$.

In some embodiments of the Formulae above, $R_3$ and $R_4$, together with the carbon atoms to which they are attached, form a $C_{5-7}$ cycloalkyl optionally substituted with one or more $R_{18}$. In another embodiment, $R_3$ and $R_4$, together with the carbon atoms to which they are attached, form a 5- to 7-membered heterocycloalkyl ring optionally substituted with one or more $R_{18}$. In another embodiment, $R_3$ and $R_4$, together with the carbon atoms to which they are attached, form a $C_{6-10}$ aryl ring optionally substituted with one or more $R_{18}$. In another embodiment, $R_3$ and $R_4$, together with the carbon atoms to which they are attached, form a 5- to 7-membered heteroaryl ring optionally substituted with one or more $R_{18}$.

In some embodiments of the Formulae above, $R_5$ is H, D, $C_{1-4}$ alkyl, $C_{2-4}$ alkenyl, $C_{2-4}$ alkynyl, $C_{3-7}$ cycloalkyl, 3- to 7-membered heterocycloalkyl, $NH_2$, $C_{1-4}$ alkylamino, or $C_{1-4}$ dialkylamino, wherein the $C_{1-4}$ alkyl, $C_{2-4}$ alkenyl, $C_{2-4}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_5$ is H, D, $C_{1-4}$ alkyl, $C_{3-7}$ cycloalkyl,3- to 7-membered heterocycloalkyl, $NH_2$, $C_{1-4}$ alkylamino, or $C_{1-4}$ dialkylamino, wherein the $C_{1-4}$ alkyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_5$ is H, D, $C_{1-4}$ alkyl, $NH_2$, $C_{1-4}$ alkylamino, or $C_{1-4}$ dialkylamino, wherein the $C_{1-4}$ alkyl is optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_5$ is H, D, $C_{1-4}$ alkyl, $NH_2$, $C_{1-4}$ alkylamino, or $C_{1-4}$ dialkylamino. In another embodiment, $R_5$ is H, D, $C_{1-4}$ alkyl, or $C_{1-4}$ dialkylamino. In another embodiment, $R_5$ is H, $C_{1-4}$ alkyl, or $C_{1-4}$ dialkylamino.

In some embodiments of the Formulae above, $R_6$ is H, D, $C_{1-4}$ alkyl, $C_{2-4}$ alkenyl, $C_{2-4}$ alkynyl, $C_{3-7}$ cycloalkyl, 3- to 7-membered heterocycloalkyl, $NH_2$, $C_{1-4}$ alkylamino, or $C_{1-4}$ dialkylamino, wherein the $C_{1-4}$ alkyl, $C_{2-4}$ alkenyl, $C_{2-4}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_6$ is H, D, $C_{1-4}$ alkyl, $C_{3-7}$ cycloalkyl, 3- to 7-membered heterocycloalkyl, $NH_2$, $C_{1-4}$ alkylamino, or $C_{1-4}$ dialkylamino, wherein the $C_{1-4}$ alkyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_6$ is H, D, $C_{1-4}$ alkyl, $NH_2$, $C_{1-4}$ alkylamino, or $C_{1-4}$ dialkylamino, wherein the $C_{1-4}$ alkyl is optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_6$ is H, D, $C_{1-4}$ alkyl, $NH_2$, $C_{1-4}$ alkylamino, or $C_{1-4}$ dialkylamino. In another embodiment, $R_6$ is H, D, $C_{1-4}$ alkyl, or $C_{1-4}$ dialkylamino. In another embodiment, $R_6$ is H, D, or $C_{1-4}$ alkyl. In another embodiment, $R_6$ is H, or $C_{1-4}$ alkyl.

In some embodiments of the Formulae above, $R_5$ and $R_6$ together with the carbon atom to which they are attached form an oxo group. In another embodiment, $R_5$ and $R_6$ together with the carbon atom to which they are attached form a $C_{3-7}$ cycloalkyl. In yet another embodiment, $R_5$ and $R_6$ together with the carbon atom to which they are attached form a 3- to 7-membered heterocycloalkyl ring.

In some embodiments of the Formulae above, $R_7$ is H, D, $C_{1-4}$ alkyl, $C_{2-4}$ alkenyl, $C_{2-4}$ alkynyl, $C_{3-7}$ cycloalkyl, 3- to 7-membered heterocycloalkyl, or $NH_2$, wherein the $C_{1-4}$ alkyl, $C_{2-4}$ alkenyl, $C_{2-4}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_7$ is H, D, $C_{1-4}$ alkyl, $C_{2-4}$ alkenyl, $C_{3-7}$ cycloalkyl, 3- to 7-membered heterocycloalkyl, or $NH_2$, wherein the $C_{1-4}$ alkyl, $C_{2-4}$ alkenyl, $C_{3-7}$ cycloalkyl, and heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_7$ is H, D, $C_{1-4}$ alkyl, $C_{2-4}$ alkenyl, or $NH_2$, wherein the $C_{1-4}$ alkyl and $C_{2-4}$ alkenyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_7$ is H, D, $C_{1-4}$ alkyl, or $NH_2$, wherein the $C_{1-4}$ alkyl is optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_7$ is H, D, $C_{1-4}$ alkyl, or $NH_2$. In another embodiment, $R_7$ is H, D, or $C_{1-4}$ alkyl. In another embodiment, $R_7$ is H or $C_{1-4}$ alkyl.

In some embodiments of the Formulae above, $R_8$ is H, D, $C_{1-4}$ alkyl, $C_{2-4}$ alkenyl, $C_{2-4}$ alkynyl, $C_{3-7}$ cycloalkyl, 3- to 7-membered heterocycloalkyl, or $NH_2$, wherein the $C_{1-4}$ alkyl, $C_{2-4}$ alkenyl, $C_{2-4}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_8$ is H, D, $C_{1-4}$ alkyl, $C_{2-4}$ alkenyl, $C_{3-7}$ cycloalkyl, 3- to 7-membered heterocycloalkyl, or $NH_2$, wherein the $C_{1-4}$ alkyl, $C_{2-4}$ alkenyl, $C_{3-7}$ cycloalkyl, and heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_8$ is H, D, $C_{1-4}$ alkyl, $C_{2-4}$ alkenyl, or $NH_2$, wherein the $C_{1-4}$ alkyl and $C_{2-4}$ alkenyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_8$ is H, D, $C_{1-4}$ alkyl, or $NH_2$, wherein the $C_{1-4}$ alkyl is optionally substituted with one or more substituents independently selected from the group consisting of $C_{1-6}$ alkyl, $C_{1-6}$ haloalkyl, halogen, $NR_{14}R_{15}$, CN, $NO_2$, and OH. In another embodiment, $R_8$ is H, D, $C_{1-4}$ alkyl, or $NH_2$. In another embodiment, $R_8$ is H, D, or $C_{1-4}$ alkyl. In another embodiment, $R_8$ is H or $C_{1-4}$ alkyl.

In some embodiments of the Formulae above, $R_7$ and $R_8$, together with the carbon atom to which they are attached, form a $C_{5-7}$ cycloalkyl ring optionally substituted with one or more $R_{19}$. In another embodiment, $R_7$ and $R_8$, together with the carbon atom to which they are attached, form a 5- to 7-membered heterocycloalkyl ring optionally substituted with one or more $R_{19}$. In another embodiment, $R_7$ and $R_8$, together with the carbon atom to which they are attached, form a $C_{6-10}$ aryl ring optionally substituted with one or more $R_{19}$. In another embodiment, $R_7$ and $R_8$, together with the carbon atom to which they are attached, form a 5- to 7-membered heteroaryl ring optionally substituted with one or more $R_{19}$.

In some embodiments of the Formulae above, $R_9$ is H, $C_{1-4}$ alkyl, $C_{2-4}$ alkenyl, $C_{2-4}$ alkynyl, —C(O)$R_{12}$, $C_{3-7}$ cycloalkyl, or 3- to 7-membered heterocycloalkyl, wherein the $C_{1-4}$ alkyl, $C_{2-4}$ alkenyl, $C_{2-4}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH. In another embodiment, $R_9$ is H, $C_{1-4}$ alkyl, —C(O)$R_{12}$, $C_{3-7}$ cycloalkyl, or 3- to 7-membered heterocycloalkyl, wherein the $C_{1-4}$ alkyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH. In another embodiment, $R_9$ is H, $C_{1-4}$ alkyl, $C_{3-7}$ cycloalkyl, or 3- to 7-membered heterocycloalkyl, wherein the $C_{1-4}$ alkyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH. In another embodiment, $R_9$ is H, $C_{1-4}$ alkyl, $C_{3-7}$ cycloalkyl, or 3- to 7-membered heterocycloalkyl. In another embodiment, $R_9$ is $C_{1-4}$ alkyl, or 3- to 7-membered heterocycloalkyl. In another embodiment, $R_9$ is H, $C_{1-4}$ alkyl, or 3- to 7-membered heterocycloalkyl.

In some embodiments of the Formulae above, $R_{10}$ is H, $C_{1-4}$ alkyl, $C_{2-4}$ alkenyl, $C_{2-4}$ alkynyl, $NR_{14}R_{15}$, $C_{3-7}$ cycloalkyl, or 3- to 7-membered heterocycloalkyl, wherein $C_{1-4}$ alkyl, $C_{2-4}$ alkenyl, $C_{2-4}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH. In another embodiment, $R_{10}$ is H, $C_{1-4}$ alkyl, $C_{2-4}$ alkenyl, or $NR_{14}R_{15}$, wherein $C_{1-4}$ alkyl and $C_{2-4}$ alkenyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH. In another embodiment, $R_{10}$ is H, $C_{1-4}$ alkyl, or $NR_{14}R_{15}$, wherein $C_{1-4}$ alkyl is optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH. In another embodiment, $R_{10}$ is H, $C_{1-4}$ alkyl, or $NR_{14}R_{15}$. In another embodiment, $R_{10}$ is H, $C_{1-3}$ alkyl, or $NR_{14}R_{15}$.

In some embodiments of the Formulae above, $R_{11}$ is H, $C_{1-4}$ alkyl, $C_{2-4}$ alkenyl, $C_{2-4}$ alkynyl, $NR_{14}R_{15}$, $C_{3-7}$ cycloalkyl, or 3- to 7-membered heterocycloalkyl, wherein $C_{1-4}$ alkyl, $C_{2-4}$ alkenyl, $C_{2-4}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH. In another embodiment, $R_{11}$ is H, $C_{1-4}$ alkyl, $C_{2-4}$ alkenyl, or $NR_{14}R_{15}$, wherein $C_{1-4}$ alkyl and $C_{2-4}$ alkenyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH. In another embodiment, $R_{11}$ is H, $C_{1-4}$ alkyl, or $NR_{14}R_{15}$, wherein $C_{1-4}$ alkyl is optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH. In another embodiment, $R_{11}$ is H, $C_{1-4}$ alkyl, or $NR_{14}R_{15}$. In another embodiment, $R_{11}$ is H, $C_{1-3}$ alkyl, or $NR_{14}R_{15}$.

In some embodiments of the Formulae above, $R_{12}$ is $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{3-7}$ cycloalkyl, or 3- to 7-membered heterocycloalkyl. In another embodiment, $R_{12}$ is $C_{1-4}$ alkyl, $C_{2-4}$ alkenyl, $C_{2-4}$ alkynyl, $C_{1-4}$ alkoxy, $C_{3-7}$ cycloalkyl, or 3- to 7-membered heterocycloalkyl. In another embodiment, $R_{12}$ is $C_{1-4}$ alkyl, $C_{2-4}$ alkenyl, $C_{2-4}$ alkynyl, or $C_{1-4}$ alkoxy. In another embodiment, $R_{12}$ is $C_{1-4}$ alkyl, $C_{2-4}$ alkenyl, or $C_{1-4}$ alkoxy. In another embodiment, $R_{12}$ is $C_{1-4}$ alkyl or $C_{1-4}$ alkoxy. In another embodiment, $R_{12}$ is $C_{1-4}$ alkyl.

In some embodiments of the Formulae above, $R_{13}$ is $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{3-7}$ cycloalkyl, or 3- to 7-membered heterocycloalkyl. In another embodiment, $R_{13}$ is $C_{1-4}$ alkyl, $C_{2-4}$ alkenyl, $C_{2-4}$ alkynyl, $C_{1-4}$ alkoxy, $C_{3-7}$ cycloalkyl, or 3- to 7-membered heterocycloalkyl. In another embodiment, $R_{13}$ is $C_{1-4}$ alkyl, $C_{2-4}$ alkenyl, $C_{2-4}$ alkynyl, or $C_{1-4}$ alkoxy. In another embodiment, $R_{13}$ is $C_{1-4}$ alkyl, $C_{2-4}$ alkenyl, or $C_{1-4}$ alkoxy. In another embodiment, $R_{13}$ is $C_{1-4}$ alkyl or $C_{1-4}$ alkoxy. In another embodiment, $R_{13}$ is $C_{1-4}$ alkyl.

In some embodiments of the Formulae above, $R_{12}$ and $R_{13}$ together with the phosphorus atom to which they are attached form a 3-8 membered heterocycloalkyl ring.

In some embodiments of the Formulae above, $R_{14}$ is H, $C_{1-4}$ alkyl, $C_{2-4}$ alkenyl, $C_{2-4}$ alkynyl, $C_{1-4}$ haloalkyl, $C_{3-7}$ cycloalkyl, or 5- to 7-membered heterocycloalkyl. In another embodiment, $R_{14}$ is H, $C_{1-4}$ alkyl, $C_{2-4}$ alkenyl, $C_{2-4}$ alkynyl, or $C_{1-4}$ haloalkyl. In another embodiment, $R_{14}$ is $C_{3-7}$ cycloalkyl, or 5- to 7-membered heterocycloalkyl. In another embodiment, $R_{14}$ is H, $C_{1-4}$ alkyl, or $C_{1-4}$ haloalkyl. In another embodiment, $R_{14}$ is H or $C_{1-4}$ alkyl. In another embodiment, $R_{14}$ is H. In another embodiment, $R_{14}$ is $C_{1-4}$ alkyl.

In some embodiments of the Formulae above, $R_{15}$ is H, $C_{1-4}$ alkyl, $C_{2-4}$ alkenyl, $C_{2-4}$ alkynyl, $C_{1-4}$ haloalkyl, $C_{3-7}$ cycloalkyl, or 5- to 7-membered heterocycloalkyl. In another embodiment, $R_{15}$ is H, $C_{1-4}$ alkyl, $C_{2-4}$ alkenyl, $C_{2-4}$ alkynyl, or $C_{1-4}$ haloalkyl. In another embodiment, $R_{15}$ is $C_{3-7}$ cycloalkyl, or 5- to 7-membered heterocycloalkyl. In another embodiment, $R_{15}$ is H, $C_{1-4}$ alkyl, or $C_{1-4}$ haloalkyl. In another embodiment, $R_{15}$ is H or $C_{1-4}$ alkyl. In another embodiment, $R_{15}$ is H. In another embodiment, $R_{15}$ is $C_{1-4}$ alkyl.

In some embodiments of the Formulae above, $R_{14}$ and $R_{15}$ together with the nitrogen atom to which they are attached form a 3- to 8-membered heterocycloalkyl ring optionally substituted with one or more substituents independently selected from the group consisting of $C_{1-6}$ alkyl, $C_{1-6}$ haloalkyl, $C_{1-6}$ hydroxyalkyl, halogen, $NR_{16}R_{17}$, CN, $NO_2$, and OH.

In some embodiments of the Formulae above, $R_{16}$ is H or $C_{1-4}$ alkyl. In another embodiment, $R_{16}$ is H or $C_{1-3}$ alkyl. In another embodiment, $R_{16}$ is $C_{1-3}$ alkyl. In another embodiment, $R_{16}$ is H or methyl. In another embodiment, $R_{16}$ is methyl. In another embodiment, $R_{16}$ is H.

In some embodiments of the Formulae above, $R_{17}$ is H or $C_{1-4}$ alkyl. In another embodiment, $R_{17}$ is H or $C_{1-3}$ alkyl. In another embodiment, $R_{17}$ is $C_{1-3}$ alkyl. In another embodiment, $R_{17}$ is H or methyl. In another embodiment, $R_{17}$ is methyl. In another embodiment, $R_{17}$ is H.

In some embodiments of the Formulae above, each $R_{18}$ is independently selected from the group consisting of halogen, OH, CN, $C_{1-4}$ alkyl, $C_{1-4}$ haloalkyl, $C_{2-4}$ alkenyl, $C_{2-4}$ alkynyl, $C_{1-4}$ alkoxy, $C_{1-4}$ haloalkoxy, $C(O)NR_{14}R_{15}$, $NR_{14}C(O)R_{12}$, and $NR_{14}R_{15}$. In another embodiment, each $R_{18}$ is independently selected from the group consisting of halogen, OH, CN, $C(O)NR_{14}R_{15}$, $NR_{14}C(O)R_{12}$, and $NR_{14}R_{15}$. In another embodiment, each $R_{18}$ is independently selected from the group consisting of $C_{1-4}$ alkyl, $C_{1-4}$ haloalkyl, $C_{2-4}$ alkenyl, $C_{2-4}$ alkynyl, $C_{1-4}$ alkoxy, and $C_{1-4}$ haloalkoxy. In another embodiment, each $R_{18}$ is independently selected from the group consisting of halogen, $C_{1-4}$ alkyl, $C_{1-4}$ haloalkyl, $C_{2-4}$ alkenyl, $C_{2-4}$ alkynyl, $C_{1-4}$ alkoxy, and $C_{1-4}$ haloalkoxy.

In some embodiments of the Formulae above, each $R_{19}$ is independently selected from the group consisting of halogen, OH, CN, $C_{1-4}$ alkyl, $C_{1-4}$ haloalkyl, $C_{2-4}$ alkenyl, $C_{2-4}$ alkynyl, $C_{1-4}$ alkoxy, $C_{1-4}$ haloalkoxy, $C(O)NR_{14}R_{15}$, $NR_{14}C(O)R_{12}$, and $NR_{14}R_{15}$. In another embodiment, each $R_{19}$ is independently selected from the group consisting of halogen, OH, CN, $C(O)NR_{14}R_{15}$, $NR_{14}C(O)R_{12}$, and $NR_{14}R_{15}$. In another embodiment, each $R_{19}$ is independently selected from the group consisting of $C_{1-4}$ alkyl, $C_{1-4}$ haloalkyl, $C_{2-4}$ alkenyl, $C_{2-4}$ alkynyl, $C_{1-4}$ alkoxy, and $C_{1-4}$ haloalkoxy. In another embodiment, each $R_{19}$ is independently selected from the group consisting of halogen, $C_{1-4}$ alkyl, $C_{1-4}$ haloalkyl, $C_{2-4}$ alkenyl, $C_{2-4}$ alkynyl, $C_{1-4}$ alkoxy, and $C_{1-4}$ haloalkoxy.

In some embodiments of the Formulae above, $R_{20}$ is H or $C_{1-4}$ alkyl. In another embodiment, $R_{20}$ is $C_{1-4}$ alkyl. In another embodiment, $R_{20}$ is H.

In some embodiments of the Formulae above, $R_{21}$ is H or $C_{1-4}$ alkyl. In another embodiment, $R_{21}$ is $C_{1-4}$ alkyl. In another embodiment, $R_{21}$ is H.

In another embodiment, $R_{20}$ and $R_9$, when on adjacent atoms, together with the atoms to which they are attached form a 5- to 7-membered heterocycloalkyl ring. In another embodiment, $R_{20}$ and $R_9$, when on adjacent atoms, together with the atoms to which they are attached form a 5- or 6-membered heterocycloalkyl ring. In another embodiment, $R_{20}$ and $R_9$, when on adjacent atoms, together with the atoms to which they are attached form a 6-membered heterocycloalkyl ring.

In some embodiments of the Formulae above, $R_{12}$ and $R_{13}$ are $C_{1-6}$ alkyl. In another embodiment, $R_{12}$ and $R_{13}$ are each $—CH_3$. In yet another embodiment, $R_{12}$ and $R_{13}$ are each $—CH_2CH_3$.

In some embodiments of the Formulae above, m is 0 or 1. In another embodiment, m is 1 or 2. In another embodiment, m is 0. In another embodiment, m is 1. In another embodiment, m is 2.

In some embodiments of the Formulae above, n is 0 or 1. In another embodiment, n is 1 or 2. In another embodiment, n is 0. In another embodiment, n is 1. In another embodiment, n is 2.

In some embodiments of the Formulae above, the sum of m and n is 0, 1, or 2.

In some embodiments of the Formulae above, q is 0. In another embodiment, q is 1. In another embodiment, q is 2. In another embodiment, q is 0 or 1. In another embodiment, q is 1 or 2.

In some embodiments of the Formulae above, $R_{16}$ and $R_{17}$ are each H.

In some embodiments of the Formulae above, $R_4$ is H.

In some embodiments of the Formulae above, $X_3$ is $CH_2$ or $C(CH_3)_2$.

In some embodiments of the Formulae above, $R_2$ is H, halogen, $C_{1-6}$ alkyl, $C_{1-6}$ haloalkyl, or $C_{2-6}$ alkenyl. In another embodiment, $R_2$ is fluoro, chloro, $CF_3$, ethyl or ethenyl.

In some embodiments of the Formulae above, $R_2$ is halogen. In another embodiment, $R_2$ is fluoro or chloro. In yet another embodiment, $R_2$ is fluoro. In a further embodiment, $R_2$ is chloro.

In some embodiments of the Formulae above, $R_1$ is $—P(O)(CH_3)_2$, $—P(O)(CH_2CH_3)_2$, or $—C(O)(CH_3)_2$. In another embodiment, $R_1$ is $—P(O)(CH_3)_2$ or $—P(O)(CH_2CH_3)_2$.

In some embodiments of the Formulae above, $R_3$ is halogen, $C_{1-6}$ alkyl, or $C_{1-6}$ alkoxy. In another embodiment, $R_3$ is methoxy, ethoxy, ethyl, fluoro, or chloro. In yet another embodiment, $R_3$ is methoxy. In another embodiment, $R_3$ is ethyl. In yet another embodiment, $R_3$ is fluoro. In a further embodiment, $R_3$ is chloro.

In another embodiment, $R_5$ is H, $C_{1-4}$ alkyl, or $C_{1-4}$ dialkylamino; or $R_5$ and $R_6$ together with the carbon atom to which they are attached form an oxo group.

In some embodiments of the Formulae above, $R_3$ is $C_{1-6}$ alkoxy. In another embodiment, $R_3$ is methoxy. In yet another embodiment, $R_3$ is ethoxy.

In some embodiments of the Formulae above, $R_2$ is chloro and $R_3$ is $C_{1-6}$ alkyl, halogen, or $C_{1-6}$ alkoxy. In another embodiment, $R_2$ is chloro and $R_3$ is methoxy.

In some embodiments of the Formulae above, $R_3$ is methoxy and $R_2$ is H, $C_{1-6}$ alkyl, $C_{1-6}$ haloalkyl, or $C_{2-6}$ alkenyl. In another embodiment, $R_3$ is methoxy and $R_2$ is H. In another embodiment, $R_3$ is methoxy and $R_2$ is ethyl. In yet another embodiment, $R_3$ is methoxy and $R_2$ is $CH{=}CH_2$. In a further embodiment, $R_3$ is methoxy and $R_2$ is $CF_3$ In some embodiments of the Formulae above, m+n=0. In another embodiment, m+n=1. In yet another embodiment, m+n=2.

In some embodiments of the Formulae above, m is 0 and n is 1. In another embodiment, m is 1 and n is 0. In yet another embodiment, m is 0 and n is 2. In another embodiment, m is 0 and n is 0. In yet another embodiment, m is 1 and n is 1.

In some embodiments of the Formulae above, $R_9$ is H, $C_{1-6}$ alkyl, or heterocycloalkyl. In another embodiment, $R_9$ is H or $C_{1-6}$ alkyl. In yet another embodiment, $R_9$ is H, methyl, ethyl, or isopropyl. In another embodiment, $R_9$ is H. In yet another embodiment, $R_9$ is methyl.

In some embodiments of the Formulae above, $R_5$ and $R_6$ together with the carbon atom to which they are attached form an oxo group. In another embodiment, $R_5$ is H and $R_6$ is H. In yet another embodiment, $R_5$ is D and $R_6$ is D.

In some embodiments of the Formulae above, $R_5$ is H, $R_6$ is H, and $R_9$ is H or $C_{1-6}$ alkyl. In another embodiment, $R_5$ is H, $R_6$ is H, and $R_9$ is H. In yet another embodiment, $R_5$ is H, $R_6$ is H, and $R_9$ is methyl. In another embodiment, $R_5$ is H, $R_6$ is H, and $R_9$ is ethyl. In a further embodiment, $R_5$ is H, $R_6$ is H, and $R_9$ is isopropyl.

In some embodiments of the Formulae above, $R_5$ is H, $R_6$ is H, and $R_9$ is methyl. In another embodiment, $R_5$ is H, $R_6$ is H, and $R_9$ is heterocycloalkyl. In yet another embodiment, $R_5$ is H, $R_6$ is H, and $R_9$ is oxetanyl. In yet another embodiment, $R_5$ is H, $R_6$ is H, and $R_9$ is piperazinyl. In a further embodiment, $R_5$ is H, $R_6$ is H, and $R_9$ is piperazinyl substituted with $—CH_2CH_2OH$.

In some embodiments of the Formulae above, $R_5$ and $R_6$ together with the carbon atom to which they are attached form an oxo group and $R_9$ is H or $C_{1-6}$ alkyl. In another embodiment, $R_5$ and $R_6$ together with the carbon atom to which they are attached form an oxo group and $R_9$ is H. In yet another embodiment, $R_5$ and $R_6$ together with the carbon atom to which they are attached form an oxo group and $R_9$ is methyl.

In some embodiments of the Formulae above, $R_5$ is H, $R_6$ is D, and $R_9$ is methyl. In another embodiment, $R_5$ is H, $R_6$ is methyl, and $R_9$ is methyl.

In some embodiments of the Formulae above, $R_5$ is H and $R_6$ is $C_{1-6}$ dialkylamino. In another embodiment, $R_5$ is H and $R_6$ is dimethylamino.

In some embodiments of the Formulae above, $R_2$ is chloro, $R_3$ is methoxy, and $R_{12}$ and $R_{13}$ are $C_{1-6}$ alkyl. In another embodiment, $R_2$ is chloro, $R_3$ is methoxy, and $R_{12}$ and $R_{13}$ are methyl. In yet another embodiment, $R_2$ is chloro, $R_3$ is methoxy, and $R_{12}$ and $R_{13}$ are ethyl. In another embodiment, $R_2$ is chloro, $R_3$ is methoxy, $R_{12}$ and $R_{13}$ are $C_{1-6}$ alkyl, m is 0, and n is 1.

In some embodiments of the Formulae above, $R_2$ is chloro, $R_3$ is methoxy, $R_{12}$ and $R_{13}$ are $C_{1-6}$ alkyl, m is 0, n is 1, and $X_4$ is $NR_9$. In another embodiment, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ are each independently H. In yet another embodiment, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ are each independently H, wherein $R_9$ is H, $C_{1-6}$ alkyl, or 3-8 membered heterocycloalkyl.

In another embodiment, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ are each independently H, wherein $R_9$ is oxetanyl. In yet another embodiment, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ are each independently H, wherein $R_9$ is H, methyl, ethyl, or isopropyl.

In another embodiment, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ are each independently H, wherein $R_9$ is H. In yet another embodiment, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ are each independently H, wherein $R_9$ is methyl. In yet another embodiment, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ are each independently H, wherein $R_9$ is ethyl. In another embodiment, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ are each independently H, wherein $R_9$ is isopropyl.

In some embodiments of the Formulae above, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ together with the carbon atom to which they are attached form an oxo group. In another embodiment, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ together with the carbon atom to which they are attached form an oxo group, wherein $R_9$ is H.

In some embodiments of the Formulae above, $R_2$ is chloro, $R_3$ is methoxy, $R_{12}$ and $R_{13}$ are $C_{1-6}$ alkyl, m is 0, n is 1, $X_4$ is $NR_9$, $R_5$ is H, and $R_6$ is methyl. In another embodiment, $R_2$ is chloro, $R_3$ is methoxy, $R_{12}$ and $R_{13}$ are $C_{1-6}$ alkyl, m is 0, n is 1, $X_4$ is $NR_9$, $R_5$ is H, and $R_6$ is methyl, wherein $R_9$ is methyl.

In some embodiments of the Formulae above, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ are each independently D. In another embodiment, $R_2$ is chloro, $R_3$ is methoxy, $R_{12}$ and $R_{13}$ are $C_{1-6}$ alkyl, m is 0, n is 1, $X_4$ is $NR_9$, and $R_5$ and $R_6$ are each independently D, wherein $R_9$ is H.

In some embodiments of the Formulae above, $R_2$ is chloro, $R_3$ is methoxy, $R_{12}$ and $R_{13}$ are $C_{1-6}$ alkyl, m is 0, n is 1, and $X_4$ is $CR_{10}R_{11}$. In another embodiment, $R_2$ is chloro, $R_3$ is methoxy, $R_{12}$ and $R_{13}$ are $C_{1-6}$ alkyl, m is 0, n is 1, and $X_4$ is $CH_2$. In yet another embodiment, $R_2$ is chloro, $R_3$ is methoxy, $R_{12}$ and $R_{13}$ are $C_{1-6}$ alkyl, m is 0, n is 1, $X_4$ is $CH_2$, $R_5$ is H, and $R_6$ is $C_{1-6}$ dialkylamino. In yet another embodiment, $R_2$ is chloro, $R_3$ is methoxy, $R_{12}$ and $R_{13}$ are $C_{1-6}$ alkyl, m is 0, n is 1, $X_4$ is $CH_2$, $R_5$ is H, and $R_6$ is $C_{1-6}$ dimethylamino.

In some embodiments of the Formulae above, $R_2$ is chloro, $R_3$ is methoxy, $R_{12}$ and $R_{13}$ are $C_{1-6}$ alkyl, m is 1, and n is 0. In another embodiment, $R_2$ is chloro, $R_3$ is methoxy, $R_{12}$ and $R_{13}$ are $C_{1-6}$ alkyl, m is 1, n is 0, and $R_5$ and $R_6$ are each independently H. In yet another embodiment, $R_2$ is chloro, $R_3$ is methoxy, $R_{12}$ and $R_{13}$ are $C_{1-6}$ alkyl, m is 1, n is 0, $R_5$ and $R_6$ are each independently H, and $X_4$ is $NR_9$.

In a further embodiment, $R_2$ is chloro, $R_3$ is methoxy, $R_{12}$ and $R_{13}$ are $C_{1-6}$ alkyl, m is 1, n is 0, $R_5$ and $R_6$ are each independently H, and $X_4$ is $NR_9$, wherein $R_9$ is H, $C_{1-6}$ alkyl, or 3-8 membered heterocycloalkyl. In another embodiment, $R_2$ is chloro, $R_3$ is methoxy, $R_{12}$ and $R_{13}$ are $C_{1-6}$ alkyl, m is 1, n is 0, $R_5$ and $R_6$ are each independently H, and $X_4$ is $NR_9$, wherein $R_9$ is H or methyl. In another embodiment, $R_2$ is chloro, $R_3$ is methoxy, $R_{12}$ and $R_{13}$ are $C_{1-6}$ alkyl, m is 1, n is 0, $R_5$ and $R_6$ are each independently H, and $X_4$ is $NR_9$, wherein $R_9$ is H. In another embodiment, $R_2$ is chloro, $R_3$ is methoxy, $R_{12}$ and $R_{13}$ are $C_{1-6}$ alkyl, m is 1, n is 0, $R_5$ and $R_6$ are each independently H, and $X_4$ is $NR_9$, wherein $R_9$ is methyl.

In some embodiments of the Formulae above, $R_2$ is chloro, $R_3$ is methoxy, $R_{12}$ and $R_{13}$ are $C_{1-6}$ alkyl, m is 0, and n is 2. In another embodiment, $R_2$ is chloro, $R_3$ is methoxy, $R_{12}$ and $R_{13}$ are $C_{1-6}$ alkyl, m is 0, n is 2, and $X_4$ is $NR_9$. In yet another embodiment, $R_2$ is chloro, $R_3$ is methoxy, $R_{12}$ and $R_{13}$ are $C_{1-6}$ alkyl, m is 0, n is 2, and $X_4$ is $NR_9$, wherein $R_9$ is methyl. In another embodiment, $R_2$ is chloro, $R_3$ is methoxy, $R_{12}$ and $R_{13}$ are $C_{1-6}$ alkyl, m is 0, n is 2, $X_4$ is $NR_9$, wherein $R_9$ is methyl, and $R_5$ and $R_6$ are each independently H. In a further embodiment, $R_2$ is chloro, $R_3$ is methoxy, $R_{12}$ and $R_{13}$ are $C_{1-6}$ alkyl, m is 0, n is 2, $X_4$ is $NR_9$, wherein $R_9$ is methyl, and $R_5$ and $R_6$ together with the carbon atom to which they are attached form an oxo group.

In some embodiments of the Formulae above, $R_2$ is chloro, $R_3$ is methoxy, $R_{12}$ and $R_{13}$ are $C_{1-6}$ alkyl, m is 0, and n is 0. In another embodiment, $R_2$ is chloro, $R_3$ is methoxy, $R_{12}$ and $R_{13}$ are $C_{1-6}$ alkyl, m is 0, n is 0, and $X_4$ is $CR_{10}R_{11}$. In yet another embodiment, $R_2$ is chloro, $R_3$ is methoxy, $R_{12}$ and $R_{13}$ are $C_{1-6}$ alkyl, m is 0, n is 0, and $X_4$ is $CH_2$. In another embodiment, $R_2$ is chloro, $R_3$ is methoxy, $R_{12}$ and $R_{13}$ are $C_{1-6}$ alkyl, m is 0, n is 0, $X_4$ is $CH_2$, $R_5$ is H, and $R_6$ is $C_{1-6}$ dialkylamino. In yet another embodiment, $R_2$ is chloro, $R_3$ is methoxy, $R_{12}$ and $R_{13}$ are $C_{1-6}$ alkyl, m is 0, n is 0, $X_4$ is $CH_2$, $R_5$ is H, and $R_6$ is $C_{1-6}$ dimethylamino.

In some embodiments of the Formulae above, $R_3$ is $C_{1-6}$ alkoxy, and $R_{12}$ and $R_{13}$ are $C_{1-6}$ alkyl. In another embodiment, $R_3$ is methoxy, and $R_{12}$ and $R_{13}$ are $C_{1-6}$ alkyl. In yet another embodiment, $R_3$ is methoxy, and $R_{12}$ and $R_{13}$ are each independently methyl.

In some embodiments of the Formulae above, $R_3$ is methoxy, $R_{12}$ and $R_{13}$ are each independently methyl, m is 0, and n is 1. In another embodiment, $R_3$ is methoxy, $R_{12}$ and $R_{13}$ are each independently methyl, m is 0, n is 1, and $X_4$ is $NR_9$. In yet another embodiment, $R_3$ is methoxy, $R_{12}$ and $R_{13}$ are each independently methyl, m is 0, n is 1, and $X_4$ is $NR_9$, wherein $R_9$ is methyl. In another embodiment, $R_3$ is methoxy, $R_{12}$ and $R_{13}$ are each independently methyl, m is 0, n is 1, and $X_4$ is $NR_9$, wherein $R_9$ is methyl and $R_5$ and $R_6$ are each independently H.

In a further embodiment, $R_3$ is methoxy, $R_{12}$ and $R_{13}$ are each independently methyl, m is 0, n is 1, and $X_4$ is $NR_9$, wherein $R_9$ is methyl, $R_5$ and $R_6$ are each independently H, and $R_2$ is H, halogen, $C_{1-6}$ alkyl, $C_{2-6}$ alkenyl, or $C_{1-6}$ haloalkyl. In another embodiment, $R_3$ is methoxy, $R_{12}$ and $R_{13}$ are each independently methyl, m is 0, n is 1, and $X_4$ is $NR_9$, wherein $R_9$ is methyl, $R_5$ and $R_6$ are each independently H, and $R_2$ is H. In yet another embodiment, $R_3$ is methoxy, $R_{12}$ and $R_{13}$ are each independently methyl, m is 0, n is 1, and $X_4$ is $NR_9$, wherein $R_9$ is methyl, $R_5$ and $R_6$ are each independently H, and $R_2$ is halogen. In another embodiment, $R_3$ is methoxy, $R_{12}$ and $R_{13}$ are each independently methyl, m is 0, n is 1, and $X_4$ is $NR_9$, wherein $R_9$ is methyl, $R_5$ and $R_6$ are each independently H, and $R_2$ is fluoro. In a further embodiment, $R_3$ is methoxy, $R_{12}$ and $R_{13}$ are each independently methyl, m is 0, n is 1, and $X_4$ is $NR_9$, wherein $R_9$ is methyl, $R_5$ and $R_6$ are each independently H, and $R_2$ is $CF_3$. In another embodiment, $R_3$ is methoxy, $R_{12}$ and $R_{13}$ are each independently methyl, m is 0, n is 1, and $X_4$ is $NR_9$, wherein $R_9$ is methyl, $R_5$ and $R_6$ are each independently H, and $R_2$ is ethyl. In yet another embodiment, $R_3$ is methoxy, $R_{12}$ and $R_{13}$ are each independently methyl, m is 0, n is 1, and $X_4$ is $NR_9$, wherein $R_9$ is methyl, $R_5$ and $R_6$ are each independently H, and $R_2$ is $CH{=}CH_2$.

In some embodiments of the Formulae above, $R_2$ is halogen, and $R_{12}$ and $R_{13}$ are $C_{1-6}$ alkyl. In another embodiment, $R_2$ is chloro, and $R_{12}$ and $R_{13}$ are $C_{1-6}$ alkyl. In yet another embodiment, $R_2$ is chloro, and $R_{12}$ and $R_{13}$ are each independently methyl. In another embodiment, $R_2$ is chloro, and $R_{12}$ and $R_{13}$ are each independently ethyl.

In some embodiments of the Formulae above, $R_2$ is chloro, $R_{12}$ and $R_{13}$ are $C_{1-6}$ alkyl, m is 0, and n is 1. In another embodiment, $R_2$ is chloro, $R_{12}$ and $R_{13}$ are $C_{1-6}$ alkyl, m is 0, n is 1, and $X_4$ is $NR_9$. In yet another embodiment, $R_2$ is chloro, $R_{12}$ and $R_{13}$ are $C_{1-6}$ alkyl, m is 0, n is 1, and $X_4$ is $NR_9$, wherein $R_9$ is methyl. In another embodiment, $R_2$ is chloro, $R_{12}$ and $R_{13}$ are $C_{1-6}$ alkyl, m is 0, n is 1, and $X_4$ is $NR_9$, wherein $R_9$ is methyl, and $R_5$ and $R_6$ are each independently H.

In a further embodiment, $R_2$ is chloro, $R_{12}$ and $R_{13}$ are $C_{1-6}$ alkyl, m is 0, n is 1, and $X_4$ is $NR_9$, wherein $R_9$ is methyl, $R_5$ and $R_6$ are each independently H, and $R_3$ is halogen, $C_{1-6}$ alkyl, or $C_{1-6}$ alkoxy. In another embodiment, $R_2$ is chloro, $R_{12}$ and $R_{13}$ are $C_{1-6}$ alkyl, m is 0, n is 1, and $X_4$ is $NR_9$, wherein $R_9$ is methyl, $R_5$ and $R_6$ are each independently H, and $R_3$ is halogen. In yet another embodiment, $R_2$ is chloro, $R_{12}$ and $R_{13}$ are $C_{1-6}$ alkyl, m is 0, n is 1, and $X_4$ is $NR_9$, wherein $R_9$ is methyl, $R_5$ and $R_6$ are each independently H, and $R_3$ is fluoro. In another embodiment, $R_2$ is chloro, $R_{12}$ and $R_{13}$ are $C_{1-6}$ alkyl, m is 0, n is 1, and $X_4$ is $NR_9$, wherein $R_9$ is methyl, $R_5$ and $R_6$ are each independently H, and $R_3$ is chloro. In a further embodiment, $R_2$ is chloro, $R_{12}$ and $R_{13}$ are $C_{1-6}$ alkyl, m is 0, n is 1, and $X_4$ is $NR_9$, wherein $R_9$ is methyl, $R_5$ and $R_6$ are each independently H, and $R_3$ is ethoxy. In another embodiment, $R_2$ is chloro, $R_{12}$ and $R_{13}$ are $C_{1-6}$ alkyl, m is 0, n is 1, and $X_4$ is $NR_9$, wherein $R_9$ is methyl, $R_5$ and $R_6$ are each independently H, and $R_3$ is ethyl.

In some embodiments of the Formulae above, A is $C_{6-10}$ aryl and $X_1$ is N. In another embodiment, A is $C_{6-10}$ aryl, $X_1$ is N, and $X_2$ is CH. In another embodiment, A is $C_{6-10}$ aryl, $X_1$ is N, $X_2$ is CH, and $R_1$ is $—P(O)R_{12}R_{13}$. In another embodiment, A is $C_{6-10}$ aryl, $X_1$ is N, $X_2$ is CH, and $R_1$ is $—P(O)R_{12}R_{13}$. In another embodiment, A is $C_{6-10}$ aryl, $X_1$ is N, $X_2$ is CH, $R_1$ is $—P(O)R_{12}R_{13}$, and $R_{16}$ is H. In another embodiment, A is $C_{6-10}$ aryl, $X_1$ is N, $X_2$ is CH, $R_1$ is $—P(O)R_{12}R_{13}$, $R_{16}$ is H, and $R_{17}$ is H. In another embodiment, A is $C_{6-10}$ aryl, $X_1$ is N, $X_2$ is CH, $R_1$ is $—P(O)R_{12}R_{13}$, $R_{16}$ is H, $R_{17}$ is H, and $R_4$ is H, halogen, or $NR_{14}R_{15}$. In another embodiment, A is $C_{6-10}$ aryl, $X_1$ is N, $X_2$ is CH, $R_1$ is $—P(O)R_{12}R_{13}$, $R_{16}$ is H, $R_{17}$ is H, $R_4$ is H, halogen, or $NR_{14}R_{15}$ and $R_2$ is H, halogen, $C_{1-6}$ alkyl, $C_{2-6}$ alkenyl, $C_{1-6}$ alkoxy, 5- to 7-membered heteroaryl, wherein the $C_{1-6}$ alkyl is optionally substituted with one or more halogen. In another embodiment, A is $C_{6-10}$ aryl, $X_1$ is N, $X_2$ is CH, $R_1$ is $—P(O)R_{12}R_{13}$, $R_{16}$ is H, $R_{17}$ is H, $R_4$ is H, halogen, or $NR_{14}R_{15}$, and $R_2$ is halogen.

A second aspect of the invention relates to compounds of Formula (II):

(II)

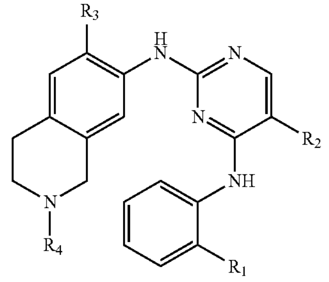

or a pharmaceutically acceptable salt, hydrate, solvate, prodrug, stereoisomer, and tautomer thereof, wherein:

$R_1$ is $C_{1-6}$ alkoxy, CN, $NO_2$, $C(O)NR_{14}R_{15}$, $SO_2R_{14}$, $SO_2NR_{14}R_{15}$, $C(O)R_{14}$, or $NR_{16}C(O)R_{14}$;

$R_2$ is halogen;

$R_3$ is $C_{1-6}$ alkoxy;

$R_4$ is H or $C_{1-6}$ alkyl;

$R_{14}$ and $R_{15}$ are each independently H, $C_{1-6}$ alkyl, $C_{2-6}$ alkenyl, $C_{2-6}$ alkynyl, $C_{1-6}$ haloalkyl, $C_{3-7}$ cycloalkyl, or 3- to 7-membered heterocycloalkyl; or $R_{14}$ and $R_{15}$ together with the nitrogen atom to which they are attached form a 3- to 8-membered heterocycloalkyl ring optionally substituted with one or more substituents each independently selected from the group consisting of $C_{1-6}$ alkyl, $C_{1-6}$ haloalkyl, $C_{1-6}$ hydroxyalkyl, halogen, $NR_{16}R_{17}$, CN, $NO_2$, and OH; and $R_{16}$ and $R_{17}$ are each independently H or $C_{1-6}$ alkyl.

In some embodiments of the Formula (II), $R_1$ is C(O)NHMe, $SO_2$-(i-Pr), or $SO_2—N(i-Pr)_2$.

In some embodiments of the Formula (II), $R_2$ is Cl.

In some embodiments of the Formula (II), $R_3$ is methoxy.

In some embodiments of the Formula (II), $R_1$ is C(O)NHMe, $SO_2$-(i-Pr), or $SO_2$—N(i-Pr)$_2$ and $R_2$ is Cl.

In some embodiments of the Formula (II), $R_2$ is Cl and $R_3$ is methoxy.

In some embodiments of the Formula (II), $R_1$ is C(O)NHMe, $SO_2$-(i-Pr), or $SO_2$—N(i-Pr)$_2$, $R_2$ is Cl, and $R_3$ is methoxy.

Non-limiting illustrative compounds of the invention include:

(2-((5-Chloro-2-((6-methoxy-2-methylisoindolin-5-yl)amino)pyrimidin-4-yl)amino)phenyl)dimethylphosphine oxide (I-1);

(2-((5-chloro-2-((6-methoxy-2-methyl-1,2,3,4-tetrahydroisoquinolin-7-yl)amino)pyrimidin-4-yl)amino)phenyl)dimethylphosphine oxide (I-2);

(2-((5-chloro-2-((8-methoxy-3-methyl-2,3,4,5-tetrahydro-1H-benzo[d]azepin-7-yl)amino)pyrimidin-4-yl)amino)phenyl)dimethylphosphine oxide (I-3);

(2-((5-chloro-2-((8-methoxy-2-methyl-2,3,4,5-tetrahydro-1H-benzo[c]azepin-7-yl)amino)pyrimidin-4-yl)amino)phenyl)dimethylphosphine oxide (I-4);

(2-((5-chloro-2-((6-fluoro-2-methyl-1,2,3,4-tetrahydroisoquinolin-7-yl)amino)pyrimidin-4-yl)amino)phenyl)dimethylphosphine oxide (I-5);

5-chloro-$N^2$-(6-chloro-2-methyl-3,4-dihydro-1H-isoquinolin-7-yl)-$N^4$-(2-dimethylphosphorylphenyl)pyrimidine-2,4-diamine (I-6);

5-chloro-$N^4$-(2-dimethylphosphorylphenyl)-$N^2$-(6-ethyl-2-methyl-3,4-dihydro-1H-isoquinolin-7-yl)pyrimidine-2,4-diamine (I-7);

5-chloro-$N^4$-(2-dimethylphosphorylphenyl)-$N^2$-(2-methyl-6-vinyl-3,4-dihydro-1H-isoquinolin-7-yl)pyrimidine-2,4-diamine (I-8);

$N^8$-[5-chloro-4-(2-dimethylphosphorylanilino)pyrimidin-2-yl]-9-methoxy-2,3,4,6,11,11a-hexahydro-1H-benzo[b]quinolizine-8,10-diamine (I-9);

5-chloro-$N^4$-(2-dimethylphosphorylphenyl)$N^2$-(9-methoxy-2,3,4,6,11,11a-hexahydro-1H-benzo[b]quinolizin-8-yl)pyrimidine-2,4-diamine (I- 10);

(2-((5-chloro-2-((2-isopropyl-6-methoxy-1,2,3,4-tetrahydroisoquinolin-7-yl)amino)pyrimidin-4-yl)amino)phenyl)dimethylphosphine oxide (I-11);

(2-((5-chloro-2-((2-ethyl-6-methoxy-1,2,3,4-tetrahydroisoquinolin-7-yl)amino)pyrimidin-4-yl)amino)phenyl)dimethylphoshine oxide (I-12);

(R)-(2-((5-chloro-2-((8-(dimethylamino)-3-methoxy-5,6,7,8-tetrahydronaphthalen-2-yl)amino)pyrimidin-4-yl)amino)phenyl)dimethylphosphine oxide (I-13);

(R)-(2-((5-chloro-2-((3-(dimethylamino)-6-methoxy-2,3-dihydro-1H-inden-5-yl)amino)pyrimidin-4-yl)amino)phenyl)dimethylphosphine oxide (I-14);

(S)-(2-((5-chloro-2-((8-(dimethylamino)-3-methoxy-5,6,7,8-tetrahydronaphthalen-2-yl)amino)pyrimidin-4-yl)amino)phenyl)dimethylphosphine oxide (I-15);

(S)-(2-((5-chloro-2-((3-(dimethylamino)-6-methoxy-2,3-dihydro-1H-inden-5-yl)amino)pyrimidin-4-yl)amino)phenyl)dimethylphosphine oxide (I- 16);

(2-((5-chloro-2-((2-(dimethylamino)-6-methoxy-2,3-dihydro-1H-inden-5-yl)amino)pyrimidin-4-yl)amino)phenyl)dimethylphosphine oxide (I-17);

(2-((5-chloro-2-((7-methoxy-2-methyl-1,2,3,4-tetrahydroisoquinolin-6-yl)amino)pyrimidin-4-yl)amino)phenyl)dimethylphosphine oxide (I-18);

(2-((5-chloro-2-((6-methoxy-2-methyl-1,2,3,4-tetrahydroisoquinolin-7-yl)amino)pyrimidin-4-yl)amino)phenyl)diethylphosphine oxide (I-19);

(2-((5-chloro-2-((6-chloro-2-methyl-1,2,3,4-tetrahydroisoquinolin-7-yl)amino)pyrimidin-4-yl)amino)phenyl)diethylphosphine oxide (I-20);

(2-((5-chloro-2-((7-chloro-2-methyl-1,2,3,4-tetrahydroisoquinolin-6-yl)amino)pyrimidin-4-yl)amino)phenyl)dimethylphosphine oxide (I-21);

(2-((5-bromo-2-((6-methoxy-2-methyl-1,2,3,4-tetrahydroisoquinolin-7-yl)amino)pyrimidin-4-yl)amino)phenyl)dimethylphosphine oxide (I-22);

(2-((5-methoxy-2-((6-methoxy-2-methyl-1,2,3,4-tetrahydroisoquinolin-7-yl)amino)pyrimidin-4-yl)amino)phenyl)dimethylphosphine oxide (I-23);

(2-((2-((5-bromo-2-methyl-1,2,3,4-tetrahydroisoquinolin-7-yl)amino)-5-chloropyrimidin-4-yl)amino)phenyl)dimethylphosphine oxide (I-24);

(2-((2-((6-methoxy-2-methyl-1,2,3,4-tetrahydroisoquinolin-7-yl)amino)pyrimidin-4-yl)amino)phenyl)dimethylphosphine oxide (I-25);

(2-((5-fluoro-2-((6-methoxy-2-methyl-1,2,3,4-tetrahydroisoquinolin-7-yl)amino)pyrimidin-4-yl)amino)phenyl)dimethylphosphine oxide (I-26);

(2-((2-((6-methoxy-2-methyl-1,2,3,4-tetrahydroisoquinolin-7-yl)amino)-5-(trifluoromethyl)pyrimidin-4-yl)amino)phenyl)dimethylphosphine oxide (I-27);

(2-((5-chloro-2-((6-methoxy-1,1,2-trimethyl-1,2,3,4-tetrahydroisoquinolin-7-yl)amino)pyrimidin-4-yl)amino)phenyl)dimethylphosphine oxide (I-28);

(2-((5-chloro-2-((6-methoxy-1,2-dimethyl-1,2,3,4-tetrahydroisoquinolin-7-yl)amino)pyrimidin-4-yl)amino)phenyl)dimethylphosphine oxide (I-29);

5-chloro-$N^4$-(2-(isopropylsulfonyl)phenyl)-$N^2$-(6-methoxy-2-methyl-1,2,3,4-tetrahydroisoquinolin-7-yl)pyrimidine-2,4-diamine (II-1);

2-((5-chloro-2-((6-methoxy-2-methyl-1,2,3,4-tetrahydroisoquinolin-7-yl)amino)pyrimidin-4-yl)amino) N,N-dimethylbenzenesulfonamide (II-2);

2-((5-chloro-2-((6-methoxy-2-methyl-1,2,3,4-tetrahydroisoquinolin-7-yl)amino)pyrimidin-4-yl)amino)-N-methylbenzamide (II-3);

7-((5-chloro-4-((2-(dimethylphosphoryl)phenyl)amino)pyrimidin-2-yl)amino)-6-methoxy-3,4-dihydroisoquinolin-1(2H)-one (I-33);

8-((5-chloro-4-((2-(dimethylphosphoryl)phenyl)amino)pyrimidin-2-yl)amino)-7-methoxy-2-methyl-2,3,4,5-tetrahydro-1H-benzo[c]azepin-1-one (I-34);

(2-((5-chloro-2-((7-methoxy-2-methyl-2,3,4,5-tetrahydro-1H-benzo[c]azepin-8-yl)amino)pyrimidin-4-yl)amino)phenyl)dimethylphosphine oxide (I-35);

(2-((5-chloro-2-((6-ethoxy-2-methyl-1,2,3,4-tetrahydroisoquinolin-7-yl)amino)pyrimidin-4-yl)amino)phenyl)dimethylphosphine oxide (I-36);

(2-((5-Chloro-2-((6-(trifluoromethyl)-1,2,3,4-tetrahydroisoquinolin-7-yl)amino)pyrimidin-4-yl)amino)phenyl)dimethylphosphine oxide (I-37);

(2-((5-chloro-2-((7-methoxy-1,2,3,4-tetrahydroisoquinolin-6-yl)amino)pyrimidin-4-yl)amino)phenyl)dimethylphosphine oxide (I-38);

(2-((5-chloro-2-((6-methoxy-1,2,3,4-tetrahydroisoquinolin-7-yl-1,1-d2)amino)pyrimidin-4-yl)amino)phenyl)dimethyl-phosphine oxide (I-39);

(2-((5-chloro-2-((6-methoxy-4,4-dimethyl-1,2,3,4-tetrahydroisoquinolin-7-yl)amino)pyrimidin-4-yl)amino)phenyl)dimethylphosphine oxide (I-40);

(2-((5-chloro-2-((6-methoxy-1,2,3,4-tetrahydroisoquinolin-7-yl)amino)pyrimidin-4-yl)amino)phenyl)dimethylphosphine oxide (I-41);

(2-((5-Chloro-2-((6-methoxy-2-(oxetan-3-yl)-1,2,3,4-tetrahydroisoquinolin-7-yl)amino)pyrimidin-4-yl)amino)phenyl)dimethylphosphine oxide (I-42);

(2-((5-chloro-2-((2-isopropyl-6-methoxy-1,2,3,4-tetrahydroiso-quinolin-7-yl-1,1-d2)amino)pyrimidin-4-yl) amino)phenyl)-dimethylphosphine oxide (I-43);

(2-((5-chloro-2-((6-methoxy-2,4,4-trimethyl-1,2,3,4-tetrahydroisoquinolin-7-yl)amino)pyrimidin-4-yl)amino)phenyl)-dimethylphosphine oxide (I-44);

(2-((5-chloro-2-((2-methyl-6-(trifluoromethyl)-1,2,3,4-tetrahydroiso-quinolin-7-yl)amino)-pyrimidin-4-yl)-amino) phenyl)dimethylphosphine oxide (I-45);

(2-((2-((6-Methoxy-2-methyl-1,2,3,4-tetrahydroisoquinolin-7-yl)amino)-5-vinylpyrimidin-4-yl)amino)phenyl)dimethylphosphine oxide (I-46);

(2-((2-((6-methoxy-2-methyl-1,2,3,4-tetrahydroisoquinolin-7-yl)amino)-5-(1-methyl-1H-pyrazol-4-yl)pyrimidin-4-yl)amino)phenyl)dimethylphosphine oxide (I-47); and (2-((5-Ethyl-2-((6-methoxy-2-methyl-1,2,3,4-tetrahydroisoquinolin-7-yl)amino)pyrimidin-4-yl)amino)phenyl)dimethylphosphine oxide (I-48).

In another embodiment of the invention, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of HPK1. In one embodiment, the compounds of the present invention are inhibitors of HPK1.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, “Stereochemistry of Organic Compounds” by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Starting materials are either commercially available or made by known procedures in the reported literature or as illustrated. Compounds of the present invention can be synthesized by following the steps outlined in General Scheme 1 which comprise the assembling of intermediates 2a and 2b. Starting materials are either commercially available or made by known procedures in the reported literature or as illustrated.

General Scheme 1

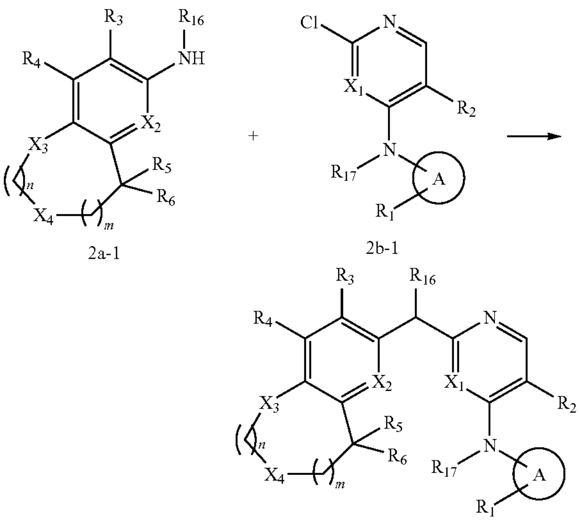

2a-1

2b-1

(I)

wherein $R_1$-$R_6$, $R_{16}$, $R_{17}$, A, $X_1$, $X_2$, $X_3$, m, and n are defined as in Formula (I).

The general manner of preparing target compounds of Formula (I) by using intermediates 2a-1 and 2b-1, is outlined above in General Scheme 1. Nucleophilic addition of 2a-1 to 2b-1 and an acid, e.g., hydrochloric acid (HCl), in a solvent (e.g. ethanol (EtOH) and/or 2-methoxyethanol, etc.) optionally at elevated temperature provides the desired product of Formula (I).

Compounds of Formula (I) and Formula (II) can exist as enantiomeric or diastereomeric stereoisomers. Enantiomerically pure compounds of Formula (I) and Formula (II) can be prepared using enantiomerically pure chiral building blocks. Alternatively, racemic mixtures of the final compounds or a racemic mixture of an advanced intermediate can be subjected to chiral purification as described herein below to deliver the desired enantiomerically pure intermediates or final compounds. In the instances where an advanced intermediate is purified into its individual enantiomers, each individual enantiomer can be carried on separately to deliver the final enantiomerically pure compounds of Formula (I) and Formula (II).

It should be understood that in the description and formula shown above, the various groups $R_1$-$R_6$, $R_{16}$, $R_{17}$, A, $X_1$, $X_2$, $X_3$, m, n, and other variables are as defined above, except where otherwise indicated. Furthermore, for synthetic purposes, the compounds of General Scheme 1 are merely representative with elected radicals to illustrate the general synthetic methodology of the compounds of Formula (I) as defined herein.

Methods of Using the Disclosed Compounds

Another aspect of the invention relates to a method of treating a disease or disorder associated with modulation of HPK1. The method comprises administering to a patient in need of a treatment for a disease or disorder associated with modulation of HPK1 an effective amount the compositions and compounds of Formula (I).

Another aspect of the invention relates to a method of preventing a disease or disorder associated with modulation of HPK1. The method comprises administering to a patient in need of a treatment for a disease or disorder associated with modulation of HPK1 an effective amount the compositions and compounds of Formula (I).

Another aspect of the invention relates to a method of treating a disease or disorder associated with modulation of HPK1. The method comprises administering to a patient in need of a treatment for a disease or disorder associated with modulation of HPK1 an effective amount the compositions and compounds of Formula (II).

Another aspect of the invention relates to a method of preventing a disease or disorder associated with modulation of HPK1. The method comprises administering to a patient in need of a treatment a disease or disorder associated with modulation of HPK1 an effective amount the compositions and compounds of Formula (II).

Another aspect of the invention relates to a method of treating a HPK1-mediated disease or disorder. The method comprises administering to a patient in need of a treatment of a disease or disorder associated with modulation of HPK1 an effective amount the compositions and compounds of Formula (I).

Another aspect of the invention relates to a method of preventing a HPK1-mediated disease or disorder. The method comprises administering to a patient in need of a treatment for diseases or disorders associated with modulation of HPK1 an effective amount the compositions and compounds of Formula (I).

Another aspect of the invention relates to a method of treating a HPK1-mediated disease or disorder. The method comprises administering to a patient in need of a treatment for diseases or disorders associated with modulation of HPK1 an effective amount the compositions and compounds of Formula (II).

Another aspect of the invention relates to a method of preventing a HPK1-mediated disease or disorder. The method comprises administering to a patient in need of a treatment for diseases or disorders associated with modulation of HPK1 an effective amount the compositions and compounds of Formula (II).

In another aspect, the present invention is directed to a method of inhibiting HPK1. The method involves administering to a patient in need thereof an effective amount of a compound of Formula (I).

In another aspect, the present invention is directed to a method of inhibiting HPK1. The method involves administering to a patient in need thereof an effective amount of a compound of Formula (II).

Another aspect of the present invention relates to a method of treating a disease or disorder in a patient associated with the inhibition of HPK1, the method comprising administering to a patient in need thereof an effective amount of a compound of Formula (I). In one embodiment, the disease or disorder is selected from the group consisting of cancer, metastasis, inflammation and auto-immune pathogenesis.

Another aspect of the present invention relates to a method of preventing a disease or disorder in a patient associated with the inhibition of HPK1, the method comprising administering to a patient in need thereof an effective amount of a compound of Formula (I).

Another aspect of the present invention relates to a method of treating a disease or disorder in a patient associated with the inhibition of HPK1, the method comprising administering to a patient in need thereof an effective amount of a compound of Formula (II).

Another aspect of the present invention relates to a method of preventing a disease or disorder in a patient associated with the inhibition of HPK1, the method comprising administering to a patient in need thereof an effective amount of a compound of Formula (II).

The present invention also relates to the use of an inhibitor of HPK1 for the preparation of a medicament used in the treatment, prevention, inhibition or elimination of a disease or disorder mediated by HPK1, wherein the medicament comprises a compound of Formula (I).

The present invention also relates to the use of an inhibitor of HPK1 for the preparation of a medicament used in the treatment, prevention, inhibition or elimination of a disease or disorder mediated by HPK1, wherein the medicament comprises a compound of Formula (II).

In another aspect, the present invention relates to a method for the manufacture of a medicament for treating, preventing, inhibiting, or eliminating a disease or disorder mediated by HPK1, wherein the medicament comprises a compound of Formula (I).

In another aspect, the present invention relates to a method for the manufacture of a medicament for treating, preventing, inhibiting, or eliminating a disease or disorder mediated by HPK1, wherein the medicament comprises a compound of Formula (II).

Another aspect of the present invention relates to a compound of Formula (I) for use in the manufacture of a medicament for treating a disease or disorder associated with inhibiting HPK1.

Another aspect of the present invention relates to a compound of Formula (II) for use in the manufacture of a medicament for treating a disease or disorder associated with inhibiting HPK1.

In another aspect, the present invention relates to the use of a compound of Formula (I) in the treatment of a disease or disorder associated with inhibiting HPK1.

In another aspect, the present invention relates to the use of a compound of Formula (II) in the treatment of a disease or disorder associated with inhibiting HPK1.

In another aspect, the present invention relates to the use of a compound of Formula (I) in the prevention of a disease or disorder associated with inhibiting HPK1.

In another aspect, the present invention relates to the use of a compound of Formula (II) in the prevention of a disease or disorder associated with inhibiting HPK1.

In some embodiments of the methods above, the disease or disorder is selected from the group consisting of cancer, metastasis, inflammation and auto-immune pathogenesis.

Another aspect of the invention relates to a method of treating cancer. The method comprises administering to a patient in need thereof an effective amount of a compound of Formula (I).

Another aspect of the invention relates to a method of treating cancer. The method comprises administering to a patient in need thereof an effective amount of a compound of Formula (II).

In some embodiments, the cancer is selected from liposarcoma, neuroblastoma, glioblastoma, bladder cancer, adrenocortical cancer, multiple myeloma, colorectal cancer, non-small cell lung cancer, oropharyngeal cancer, penis cancer, anal cancer, thyroid cancer, vaginal cancer, gastric cancer, rectal cancer, thyroid cancer, Hodgkin lymphoma and diffuse large B-cell lymphoma.

Another aspect of the invention relates to a method of inducing cell cycle arrest, apoptosis in tumor cells, and/or enhanced tumor-specific T cell immunity. The method comprises contacting the cells with an effective amount of a compound of Formula (I).

Another aspect of the invention relates to a method of inducing cell cycle arrest, apoptosis in tumor cells, and/or enhanced tumor-specific T cell immunity. The method comprises contacting the cells with an effective amount of a compound of Formula (II).

In one embodiment, the present invention relates to the use of an inhibitor of HPK1 for the preparation of a medicament used in treatment, prevention, inhibition or elimination of a disease or disorder associated with associated with cancer and metastasis.

In another embodiment, the present invention relates to a compound of Formula (I) or Formula (II) or a pharmaceutical composition comprising a compound of the present invention and a pharmaceutically acceptable carrier used for the treatment of cancers including, but not limited to, liposarcoma, neuroblastoma, glioblastoma, bladder cancer, adrenocortical cancer, multiple myeloma, colorectal cancer, non-small cell lung cancer, oropharyngeal cancer, penis cancer, anal cancer, thyroid cancer, vaginal cancer, gastric cancer, rectal cancer, thyroid cancer, Hodgkin lymphoma and diffuse large B-cell lymphoma.

In some embodiments, administration of a compound of Formula (I) or a pharmaceutical composition comprising a compound of the present invention and a pharmaceutically acceptable carrier induces a change in the cell cycle or cell viability.

In some embodiments, administration of a compound of Formula (II) or a pharmaceutical composition comprising a compound of the present invention and a pharmaceutically acceptable carrier induces a change in the cell cycle or cell viability.

Another aspect of the invention relates to a method of treating inflammation. The method comprises administering to a patient in need thereof an effective amount of a compound of Formula (I).

Another aspect of the invention relates to a method of treating inflammation. The method comprises administering to a patient in need thereof an effective amount of a compound of Formula (II).

Another aspect of the invention relates to a method of treating auto-immune pathogenesis. The method comprises administering to a patient in need thereof an effective amount of a compound of Formula (I).

Another aspect of the invention relates to a method of treating auto-immune pathogenesis. The method comprises administering to a patient in need thereof an effective amount of a compound of Formula (II).

Another aspect of the invention is directed to pharmaceutical compositions comprising a compound of Formula (I) and a pharmaceutically acceptable carrier. The pharmaceutical acceptable carrier may further include an excipient, diluent, or surfactant.

Another aspect of the invention is directed to pharmaceutical compositions comprising a compound of Formula (II) and a pharmaceutically acceptable carrier. The pharmaceutical acceptable carrier may further include an excipient, diluent, or surfactant.

In one embodiment, are provided methods of treating a disease or disorder associated with modulation of HPK1 including, cancer, metastasis, inflammation and auto-immune pathogenesis, comprising administering to a patient suffering from at least one of said diseases or disorder a compound of Formula (I).

In one embodiment, are provided methods of treating a disease or disorder associated with modulation of HPK1 including, cancer, metastasis, inflammation and auto-immune pathogenesis, comprising administering to a patient suffering from at least one of said diseases or disorder a compound of Formula (II).

In one embodiment, are provided methods of treating a disease or disorder associated with modulation of HPK1 including, cancer and metastasis, comprising administering to a patient suffering from at least one of said diseases or disorder a compound of Formula (I).

In one embodiment, are provided methods of treating a disease or disorder associated with modulation of HPK1 including, cancer and metastasis, comprising administering to a patient suffering from at least one of said diseases or disorder a compound of Formula (II).

One therapeutic use of the compounds or compositions of the present invention which inhibit HPK1 is to provide treatment to patients or subjects suffering from cancer, metastasis, inflammation and auto-immune pathogenesis.

Another therapeutic use of the compounds or compositions of the present invention which inhibit HPK1 is to provide treatment to patients or subjects suffering from cancer and metastasis.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Another aspect of the invention is directed to pharmaceutical compositions comprising a compound of Formula (II) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained on Bruker spectrometers at 400 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI). (Column: Acquity UPLC BEH C18 1.7 m 2.1×50 mm; Flow rate 0.6 mL/min; Solvent A (95/5/0.1%: 10 mM Ammonium Formate/Acetonitrile/Formic Acid), Solvent B (95/5/0.09%: Acetonitrile/Water/Formic Acid); gradient: 5-100% B from 0 to 2 mins, hold 100% B to 2.2 mins and 5% B at 2.21 mins. Abbreviations used in the following examples and elsewhere herein are:

ACN acetonitrile
atm atmosphere
br broad
BBN 9-borabicyclo[3.3.1]nonane
BINAP (2,2'-bis(diphenylphosphino)-1,1'-binaphthyl)
DABCO 1,4-diazabicyclo[2.2.2]octane
DAST diethylaminosulfur trifluoride
DBU 2,3,4,6,7,8,9,10-octahydropyrimido[1,2-a]azepine
DCM dichloromethane
DIPEA N,N-diisopropylethylamine
DMA N,N-dimethylacetamide
DMF N,N-dimethylformamide
DMSO dimethyl sulfoxide
dppf 1,1'-bis(diphenylphosphino)ferrocene
EDC N-(3-Dimethylaminopropyl)-N'-ethylcarbodiimide hydrochloride
EI electron ionization
ESI electrospray ionization
Et ethyl
EtOAc ethyl acetate
EtOH ethanol
GCMS gas chromatography-mass spectrometry
h hour(s)
HATU 2-(7-Aza-1H-benzotriazole-1-yl)-1,1,3,3-tetramethyluronium hexafluorophosphate
HPLC high-performance liquid chromatography
LCMS liquid chromatography-mass spectrometry
m multiplet
Me methyl
MeI methyl iodide
MeOH methanol
MHz megahertz
min minutes
MS molecular sieves
MTBE 2-methoxy-2-methylpropane
MW microwave
NMR nuclear magnetic resonance
ppm parts per million
PSI Pounds per square inch
SPhos 2-Dicyclohexylphosphino-2',6'-dimethoxybiphenyl
s singlet
SM starting material TFA trifluoroacetic acid TLC thin layer chromatography v volume wt weight Methods for the Synthesis of Compounds of Formula (I)

Method A

Example 1: (2-((5-Chloro-2-((6-methoxy-2-methylisoindolin-5-yl)amino)pyrimidin-4-yl)amino)phenyl) dimethylphosphine oxide (I-1)

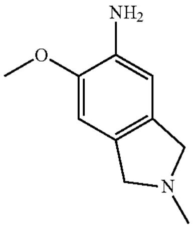

49

+

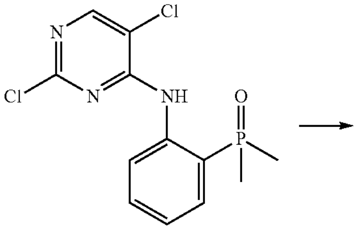

-continued

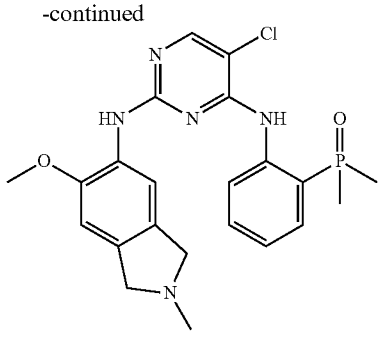

I-1

6-Methoxy-2-methylisoindolin-5-amine 49 (87 mg, 0.49 mmol) was combined with (2-((2,5-dichloropyrimidin-4-yl)amino)phenyl)dimethylphosphine oxide (154 mg, 0.49 mmol, prepared as described in *J. Med. Chem.* 2016, 59, 4948), 1 mL of 2-methoxyethanol and 0.70 mL HCl solution (1 M in EtOH). The reaction mixture was stirred at 85° C. for 14 h. The reaction mixture was cooled to rt. Volatiles were removed under reduced pressure. The residue was taken up in DCM and saturated sodium carbonate solution. The organic layer was separated and the aqueous phase was extracted with DCM (2×). The organic layers were combined, dried over sodium sulfate, filtered, and concentrated. The residue was purified by flash chromatography on silica gel column with 0 to 10% MeOH/DCM to afford the title compound as a light brown solid (32% yield). $^1$H NMR (400 MHz, $CDCl_3$): δ 10.74 (s, 1H), 8.55 (ddd, J=8.5, 4.4, 1.0 Hz, 1H), 8.17 (s, 1H), 8.10 (s, 1H), 7.60-7.48 (m, 2H), 7.36-7.27 (m, 1H), 7.15 (tdd, J=7.5, 2.4, 1.1 Hz, 1H), 6.74 (s, 1H), 3.88 (d, J=10.1 Hz, 5H), 3.83 (q, J=1.5 Hz, 2H), 2.59 (s, 3H), 1.83 (d, J=13.2 Hz, 6H). ESI-MS m/z: 458.1 [M+H]+.

The compounds in Table 1 were synthesized as described in Method A above using the corresponding aniline intermediates and 4,5-disubstituted 2-chloropyrimidines. The preparation of the aniline intermediates is described herein in Examples 49-76. The 2-chloropyrimidine precursors were synthesized according to literature procedures (*J. Med. Chem.* 2016, 59, 4948). Compounds I-9 and I-10 were additionally purified by preparative HPLC, (Waters Sunfire C18 column) eluting with a gradient of 5 to 55% ACN in water with a 0.1% TFA modifier.

TABLE 1

| Example | Structure | Aniline intermediate | $^1$H NMR (400 MHz) | ESI-MS m/z |
|---|---|---|---|---|
| 2 | 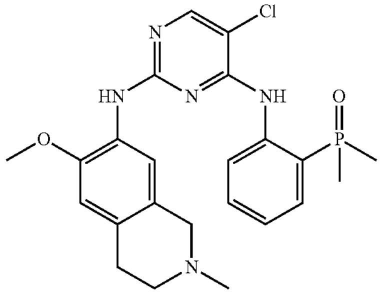 I-2 | 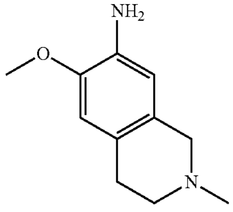 50 | ($CDCl_3$) δ 10.76 (s, 1H), 8.56 (dd, J = 4.39, 7.91 Hz, 1H), 8.10 (s, 1H), 7.96 (s, 1H), 7.50-7.57 (m, 1H), 7.47 (s, 1H), 7.27-7.33 (m, 1H), 7.13 (ddt, J = 1.00, 2.32, 7.50 Hz, 1H), 6.60 (s, 1H), 3.85 (s, 3H), 3.43 (s, 2H), 2.87 (t, J = 5.77 Hz, 2H), 2.64-2.72 (m, 2H), 2.44 (s, 3H), 1.83 (d, J = 13.05 Hz, 6H) | 472.2 [M + H]$^+$ |

TABLE 1-continued

| Example Structure | | Aniline intermediate | $^{1}$H NMR (400 MHz) | ESI-MS m/z |
|---|---|---|---|---|
| 3 | 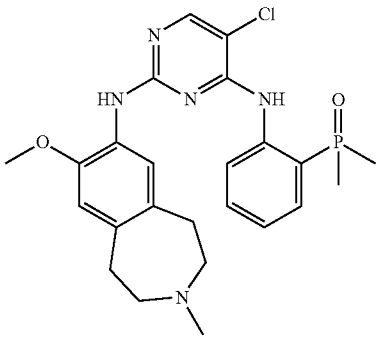 I-3 | 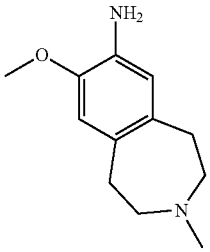 51 | ($CDCl_3$) δ10.80 (s, 1H), 8.60 (ddd, J = 8.6, 4.4, 1.1 Hz, 1H), 8.10 (s, 1H), 8.06 (s, 1H), 7.55-7.42 (m, 2H), 7.33-7.26 (m, 1H), 7.11 (tdd, J = 7.5, 2.4, 1.1 Hz, 1H), 6.65 (s, 1H), 3.86 (s, 3H), 2.84 (ddd, J = 38.2, 6.1, 3.7 Hz, 4H), 2.56 (t, J = 9.4 Hz, 4H), 2.37 (s, 3H), 1.83 (d, J = 13.1 Hz, 6H) | 486.1 $[M + H]^+$ |
| 4 | 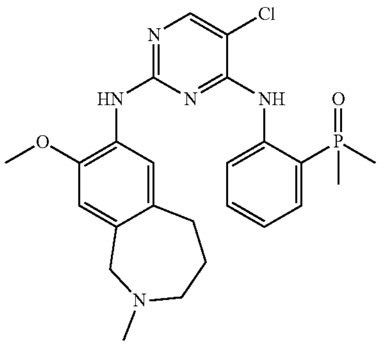 I-4 | 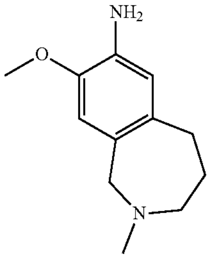 52 | ($CDCl_3$) δ 10.75 (s, 1H), 8.55 (ddd, J = 8.5, 4.4, 1.0 Hz, 1H), 8.05 (d, J = 3.3 Hz, 2H), 7.43 (tdd, J = 5.4, 4.4, 1.4 Hz, 2H), 7.27-7.20 (m, 1H), 7.04 (tdd, J = 7.4, 2.4, 1.1 Hz, 1H), 6.61 (s, 1H), 3.80 (s, 3H), 3.68 (s, 2H), 2.98-2.86 (m, 2H), 2.75-2.61 (m, 2H), 2.27 (s, 3H), 1.77 (d, J = 13.1 Hz, 6H), 1.67 (p, J = 5.4 Hz, 2H) | 486.1 $[M + H]^+$ |
| 5 | 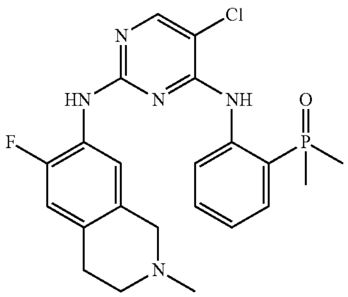 I-5 | 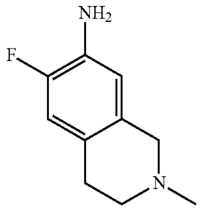 53 | ($CDCl_3$) δ 10.88 (s, 1H), 8.53 (dd, J = 4.4, 8.2 Hz, 1H), 8.10 (s, 1H), 7.87 (d, J = 8.3 Hz, 1H), 7.58-7.39 (m, 1H), 7.34-7.23 (m, 1H), 7.18 (d, J = 2.3 Hz, 1H), 7.11 (ddt, J = 1.0, 2.3, 7.5 Hz, 1H), 6.83 (d, J = 11.7 Hz, 1H), 3.44 (s, 2H), 2.85 (t, J = 5.9 Hz, 2H), 2.69-2.62 (m, 2H), 2.43 (s, 3H), 1.83 (d, J = 13.2 Hz, 6H) | 460.1 $[M + H]^+$ |
| 6 | 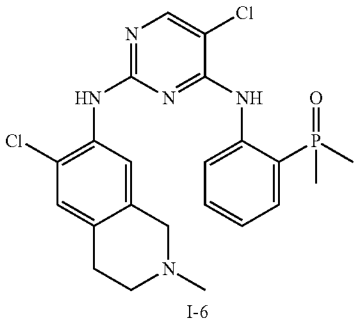 I-6 | 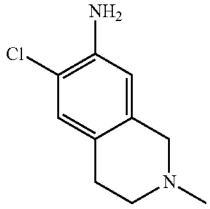 54 | ($CDCl_3$) = 10.90 (s, 1H), 8.55 (dd, J = 4.8, 8.8 Hz, 1H), 8.12 (s, 1H), 8.00 (s, 1H), 7.53-7.47 (m, 1H), 7.35-7.30 (m, 2H), 7.21-7.08 (m, 2H), 3.45 (s, 2H), 2.91-2.80 (m, 2H), 2.67 (t , J = 5.9 Hz, 2H), 2.43 (s, 3H), 1.86 (s, 3H), 1.83 (s, 3H) | 476.4 $[M + H]^+$ |

TABLE 1-continued

| Example | Structure | Aniline intermediate | $^1$H NMR (400 MHz) | ESI-MS m/z |
|---|---|---|---|---|
| 7 | 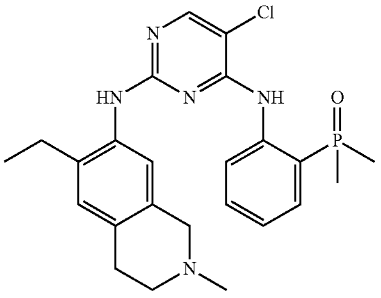 I-7 | 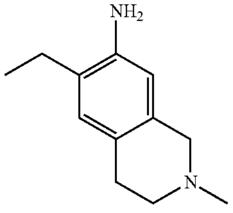 75 | (CDCl$_3$) δ 10.95 (s, 1H), 8.67-8.45 (m, 1H), 8.05 (s, 1H), 7.42 (s, 1H), 7.37 (t, J = 8.0 Hz, 1H), 7.27-7.18 (m, 1H), 7.11-7.01 (m, 1H), 6.98 (s, 1H), 6.57 (s, 1H), 3.51 (s, 1H), 2.92 (t, J = 6.0 Hz, 2H), 2.72 (t, J = 5.9 Hz, 2H), 2.61 (q, J = 7.6 Hz, 2H), 2.45 (s, 3H), 1.84 (s, 3H), 1.81 (s, 3H) | 470.4 [M + H]$^+$ |
| 8 | 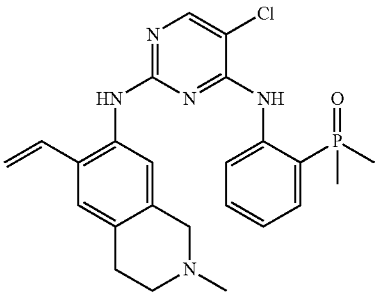 I-8 | 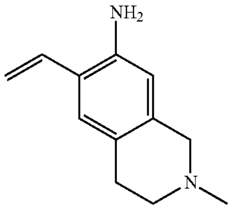 74 | (CDCl$_3$) δ 10.96 (s, 1H), 8.56 (dd, J = 8.5, 4.6 Hz, 1H), 8.06 (s, 1H), 7.42 (s, 1H), 7.36 (dd, J = 8.7, 7.2 Hz, 1H), 7.06 (d, J = 2.0 Hz, 1H), 6.86 (dd, J = 17.5, 11.0 Hz, 1H), 6.66 (s, 1H), 5.64 (dd, J = 17.5, 1.4 Hz, 1H), 5.34-5.23 (m, 1H), 3.52 (s, 3H). 2.93 (t, J = 6.0 Hz, 2H), 2.71 (t, J = 6.0 Hz, 2H), 2.44 (s, 3H), 1.84 (s, 3H), 1.81 (s, 3H) | 468.4 [M + H]$^+$ |
| 9 | 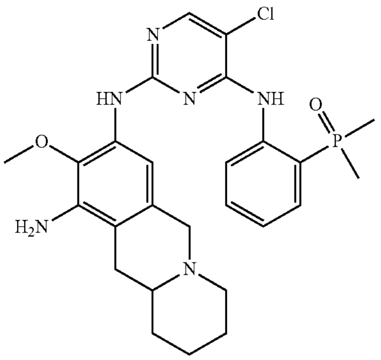 I-9 | 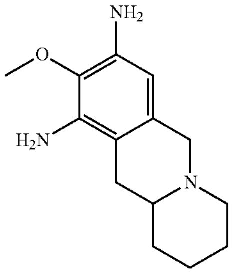 66 | (CDC1$_3$) δ 10.77 (s, 1H), 8.59 (dd, J = 8.5, 4.4 Hz, 1H), 8.10 (s, 1H), 7.62-7.49 (m, 1H), 7.43 (s, 1H), 7.31 (d, J = 3.1 Hz, 1H), 7.17-7.08 (m, 1H), 3.76 (s, 3H), 3.68 (s, 2H), 3.61 (d, J = 14.8 Hz, 1H), 3.26 (d, J = 15.2 Hz, 2H), 3.03 (d, J = 11.4 Hz, 2H), 2.52 (dd, J = 15.6, 4.2 Hz, 1H), 2.39-2.27 (m, 1H), 2.28-2.16 (m, OH), 2.14-2.03 (m, 1H), 1.93-1.85 (m, 2H), 1.85 (s, 3H), 1.82 (s, 3H), 1.76-1.66 (m, 2H), 1.45-1.34 (m, 2H) | 526.6 [M + H]$^+$ |
| 10 | 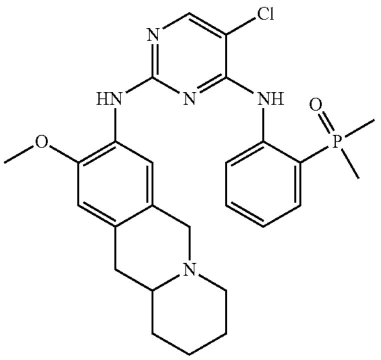 I-10 | 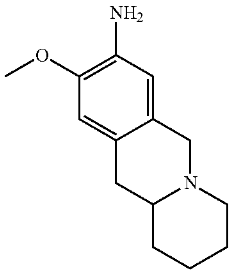 64 | (CDCl$_3$) δ 10.71 (s, 1H), 8.54 (dd, J = 8.5, 4.4 Hz, 1H), 7.98 (s, 1H), 7.60-7.46 (m, 2H), 7.30 (ddd, J = 14.1, 7.7, 1.7 Hz, 1H), 7.17-7.08 (m, 1H), 6.55 (s, 1H), 3.84 (s, 3H), 3.73-3.64 (m, 1H), 3.28 (d, J = 14.5 Hz, 1H), 3.05 (d, J = 11.3 Hz, 1H), 2.70 (d, J = 7.2 Hz, 2H), 2.24 (s, 1H), 2.12 (s, 1H), 1.85 (d, J = 2.6 Hz, 2H), 1.85-1.79 (m, 2H), 1.71 (d, J = 6.0 Hz, 3H), 1.61-1.56 (m, 14H), 1.38 (dd, J = 11.5, 6.8 Hz, 3H) | 511.7 [M + H]$^+$ |

TABLE 1-continued

| Example Structure | | Aniline intermediate | $^1$H NMR (400 MHz) | ESI-MS m/z |
|---|---|---|---|---|
| 11 | 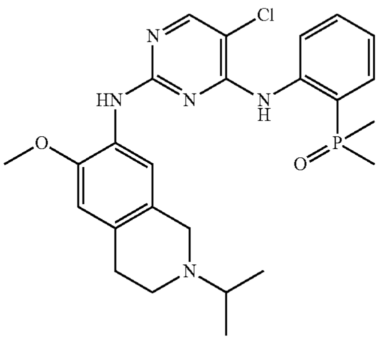 I-11 | 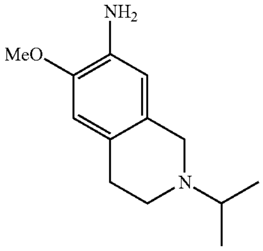 55 | (CDCl$_3$) δ 10.75 (s, 1H), 8.57 (dd, J = 8.4, 4.2 Hz, 1H), 8.11 (s, 1H), 7.99 (s, 1H), 7.59-7.46 (m, 2H), 7.30 (ddd, J = 14.1,7.7, 1.6 Hz, 1H), 7.16-7.07 (m, 1H), 6.59 (s, 1H), 3.84 (s, 3H), 3.57 (s, 2H), 2.92-2.80 (m, 3H), 2.76 (t, J = 5.8 Hz, 2H), 1.84 (d, J = 13.1 Hz, 6H), 1.14 (d, J = 6.6 Hz, 6H) | 500.1 $[M + H]^+$ |
| 12 | 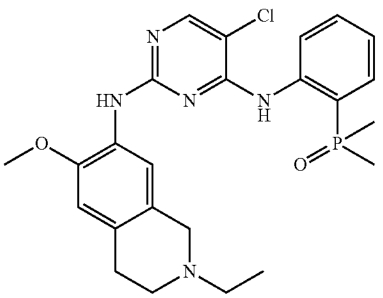 I-12 | 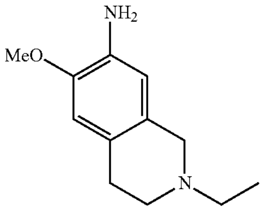 56 | (CDCl$_3$) δ 10.75 (s, 1H), 8.57 (ddd, J = 8.6, 4.4, 1.1 Hz, 1H), 8.11 (s, 1H), 7.99 (s, 1H), 7.54 (ddt, J = 8.6, 7.3, 1.4 Hz, 1H), 7.49 (s, 1H), 7.30 (ddd, J = 14.0, 7.6, 1.5 Hz, 1H), 7.12 (tdd, J = 7.6, 2.4, 1.1 Hz, 1H), 6.59 (s, 1H), 3.85 (s, 3H), 3.47 (s, 2H), 2.86 (t, J = 5.9 Hz, 2H), 2.72 (t, J = 5.9 Hz, 2H), 2.56 (q, J = 7.2 Hz, 2H), 1.84 (d, J = 13.2 Hz, 6H), 1.19 (t, J = 7.2 Hz, 3H) | 486.1 $[M + H]^+$ |
| 13 | 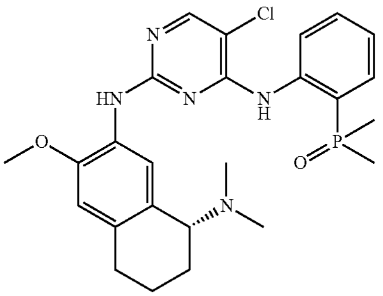 I-13 | 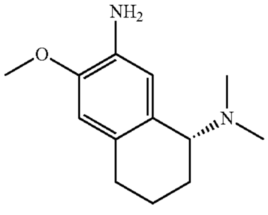 57 | (CDCl$_3$) δ 10.79 (s, 1H), 8.63 (ddd, J = 8.5, 4.4, 1.0 Hz, 1H), 8.21 (s, 1H), 8.11 (s, 1H), 7.45 (ddt, J = 8.6, 7.2, 1.4 Hz, 1H), 7.31-7.21 (m, 3H), 7.09 (tdd, J = 7.6, 2.4, 1.1 Hz, 1H), 6.57 (s, 1H), 3.84 (s, 3H), 3.64 (t, J = 6.5 Hz, 1H), 2.82-2.59 (m, 2H), 2.13 (s, 6H), 2.04-1.92 (m, 1H), 1.90-1.74 (m, 7H), 1.79-1.63 (m, 2H) | 500.2 $[M + H]^+$ |
| 14 | 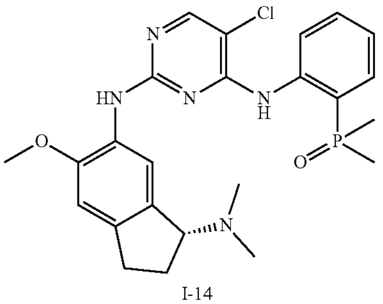 I-14 | 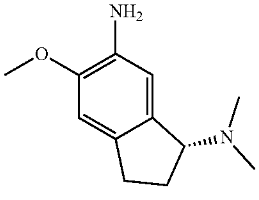 68 | (CDCl$_3$) δ 10.77 (s, 1H), 8.61 (ddd, J = 8.6, 4.5, 1.1 Hz, 1H), 8.23 (s, 1H), 8.11 (s, 1H), 7.53 (ddt, J = 8.7, 7.3, 1.4 Hz, 1H), 7.44 (s, 1H), 7.33-7.20 (m, 1H), 7.11 (tdd, J = 7.5, 2.4, 1.1 Hz, 1H), 6.75 (s, 1H), 4.21 (dd, J = 7.4, 4.6 Hz, 1H), 3.87 (s, 3H), 2.92 (dt, J = 15.6, 7.6 Hz, 1H), 2.78 (ddd, J = 16.1, 8.7, 5.3 Hz, 1H), 2.13 (s, 6H), 2.13-1.98 (m, 2H), 1.88-1.77 (m, 6H) | 486.1 $[M + H]^+$ |

TABLE 1-continued

| Example | Structure | Aniline intermediate | $^1H$ NMR (400 MHz) | ESI-MS m/z |
|---|---|---|---|---|
| 15 | 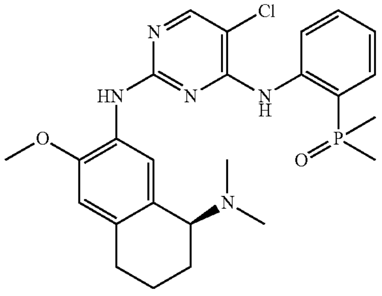<br>I-15 | 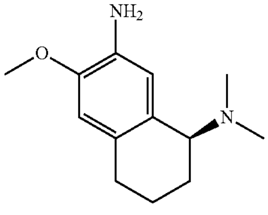<br>70 | ($CDCl_3$) δ 10.79 (s, 1H), 8.62 (ddd, J = 8.6, 4.4, 1.0 Hz, 1H), 8.21 (s, 1H), 8.11 (s, 1H), 7.45 (ddt, J = 8.6, 7.2, 1.4 Hz, 1H), 7.31-7.21 (m, 1H), 7.25 (s, 1H), 7.09 (tdd, J = 7.5, 2.4, 1.1 Hz, 1H), 6.57 (s, 1H), 3.84 (s, 3H), 3.64 (dd, J = 7.8, 5.3 Hz, 1H), 2.82-2.59 (m, 2H), 2.13 (s, 6H), 1.98 (tdd, J = 8.2, 6.3, 3.9 Hz, 1H), 1.90-1.69 (m, 7H), 1.73-1.59 (m, 2H) | 500.1 $[M + H]^+$ |
| 16 | 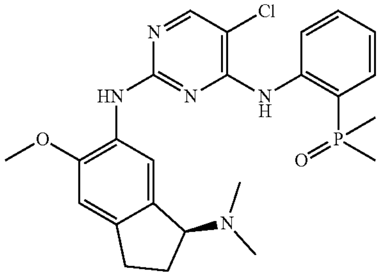<br>I-16 | 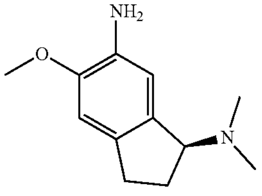<br>69 | ($CDCl_3$) δ 10.77 (s, 1H), 8.60 (ddd, J = 8.5, 4.4, 1.0 Hz, 1H), 8.23 (s, 1H), 8.11 (s, 1H), 7.53 (ddt, J = 8.7, 7.2, 1.5 Hz, 1H), 7.44 (s, 1H), 7.33-7.20 (m, 1H), 7.12 (tdd, J = 7.5, 2.4, 1.1 Hz, 1H), 6.75 (s, 1H), 4.21 (dd, J = 7.5, 4.5 Hz, 1H), 3.87 (s, 3H), 2.92 (dt, J = 15.6, 7.6 Hz, 1H), 2.78 (ddd, J = 16.0, 8.6, 5.2 Hz, 1H), 2.13 (s, 6H), 2.17-2.00 (m, 2H), 1.88-1.77 (m, 6H) | 486.1 $[M + H]^+$ |
| 17 | 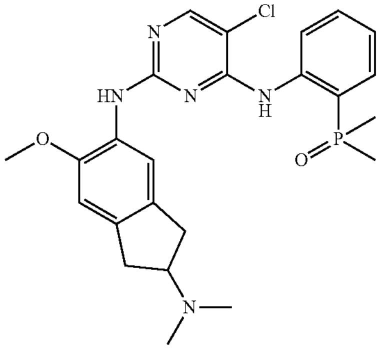<br>I-17 | 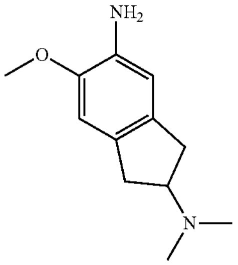<br>58 | ($CDCl_3$) δ 10.78 (s, 1H), 8.59 (ddd, J = 8.5, 4.4, 1.0 Hz, 1H), 8.12 (d, J = 10.2 Hz, 2H), 7.51 (ddt, J = 8.6, 7.3, 1.4 Hz, 1H), 7.48 (s, 1H), 7.34-7.24 (m, 1H), 7.12 (tdd, J = 7.5, 2.4, 1.1 Hz, 1H), 6.74 (s, 1H), 3.86 (s, 3H), 3.09-2.83 (m, 5H), 2.32 (s, 6H), 1.83 (d, J = 13.2 Hz, 6H) | 486.1 $[M + H]^+$ |
| 18 | 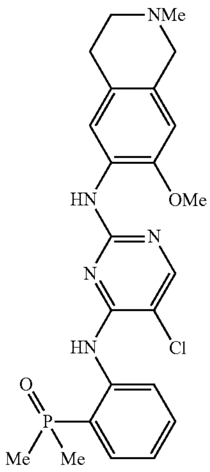<br>I-18 | 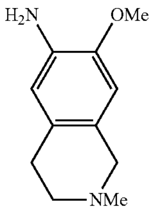<br>60 | ($CDCl_3$): δ 10.80 (s, 1H), 8.60 (dd, J = 4.3, 8.1 Hz, 1H), 8.11 (s, 1H), 8.04 (s, 1H), 7.54-7.48 (m, 1H), 7.47 (s, 1H), 7.30 (dt, J = 1.4, 7.0 Hz, 1H), 7.12 (ddt, J = 1.0, 2.4, 7.5 Hz, 1H), 6.52 (s, 1H), 3.84 (s, 3H), 3.54 (s, 2H), 2.78 (t, J = 5.8 Hz, 2H), 2.66 (t, J = 5.8 Hz, 2H), 2.46 (s, 3H), 1.85 (s, 3H), 1.82 (s, 3H) | 472.5 $[M + H]^+$ |

TABLE 1-continued

| Example | Structure | Aniline intermediate | $^1H$ NMR (400 MHz) | ESI-MS m/z |
|---|---|---|---|---|
| 19 | 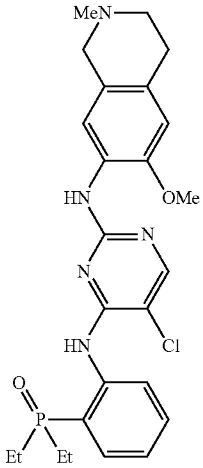<br>I-19 | 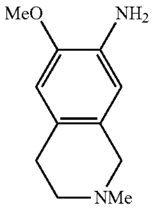<br>50 | ($CDCl_3$): δ 10.99 (s, 1H), 8.59 (dd, J = 4.0, 8.4 Hz, 1H), 8.10 (s, 1H), 7.97 (s, 1H), 7.57-7.47 (m, 1H), 7.45 (s, 1H), 7.22 (ddd, J = 1.5, 7.7, 12.4 Hz, 1H), 7.11 (ddt, J = 1.1, 2.3, 7.5 Hz, 1H), 6.60 (s, 1H), 3.85 (s, 3H), 3.44 (s, 2H), 2.87 (t, J = 5.8 Hz, 2H), 2.69 (t, J = 5.8 Hz, 2H), 2.45 (s, 3H), 2.13-1.92 (m, 4H), 1.22 (t, J = 7.7 Hz, 3H), 1.18 (t, J = 7.7 Hz, 3H) | 500.4 $[M + H]^+$ |
| 20 | 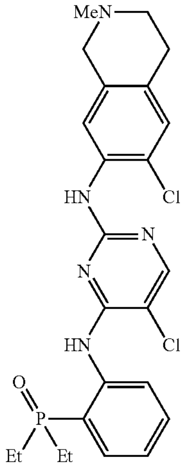<br>I-20 | 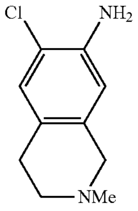<br>54 | ($CDCl_3$): δ 11.13 (s, 1H), 8.58 (dd, J = 3.8, 8.2 Hz, 1H), 8.11 (s, 1H), 8.00 (s, 1H), 7.49 (tdd, J = 1.3, 7.3, 8.5 Hz, 1H), 7.22 (ddd, J = 1.5, 7.8, 12.5 Hz, 1H), 7.14 (s, 1H), 7.11 (ddt, J = 1.0, 2.4, 7.5 Hz, 1H), 3.44 (s, 2H), 2.86 (t, J = 5.9 Hz, 2H), 2.66 (t, J = 5.9 Hz, 2H), 2.43 (s, 3H), 2.11-1.93 (m, 4H), 1.22 (t, J = 7.7 Hz, 3H), 1.18 (t, J = 7.7 Hz, 3H) | 504.4 $[M + H]^+$ |
| 21 | 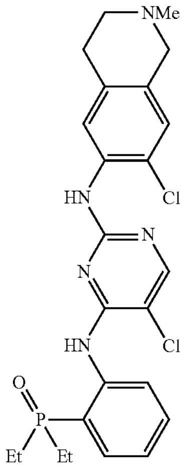<br>I-21 | 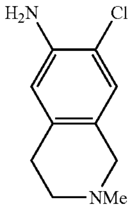<br>61 | (DMSO-$d_6$): δ 11.31 (s, 1H), 8.80 (s, 1H), 8.45 (dd, J = 4.6, 8.7 Hz, 1H), 8.15 (s, 1H), 7.60-7.51 (m, 2H), 7.42-7.35 (m, 2H), 7.16-7.07 (m, 1H), 4.21 (br s, 2H), 2.98 (br s, 2H), 2.83 (br s, 2H), 1.79 (s, 3H), 1.76 (s, 3H) | 476.3 $[M + H]^+$ |

TABLE 1-continued
| Example | Structure | Aniline intermediate | $^1$H NMR (400 MHz) | ESI-MS m/z |
|---|---|---|---|---|
| 22 | 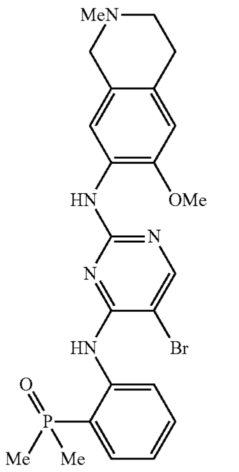 I-22 | 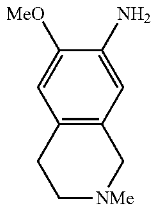 50 | (DMSO-$d_6$): δ 10.85 (s, 1H), 8.30 (dd, J = 8.6, 4.2 Hz, 1H), 8.23 (s, 1H), 8.07 (s, 1H), 7.59 (ddd, J = 13.7, 7.7, 1.6 Hz, 1H), 7.56 (s, 1H), 7.51 (t, J = 7.9 Hz, 1H), 7.22-7.16 (m, 1H), 6.88 (s, 1H), 3.91 (br. s, 3H), 3.80 (s, 3H), 3.22 (br. s, 2H), 2.99 (br. s, 2H), 2.74 (s, 3H), 1.76 (d, J = 13.5 Hz, 6H) | 516.1 $[M + H]^+$ |
| 23 | 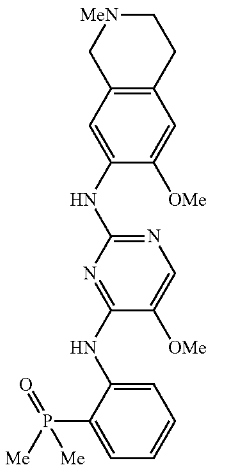 I-23 | 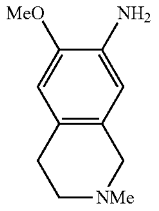 50 | ($CDCl_3$): δ 10.81 (s, 1H), 8.72 (dd, J = 8.5, 4.4 Hz, 1H), 8.41 (s, 1H), 8.15 (s, 1H), 7.75 (s, 1H), 7.57-7.49 (m, 2H), 7.27 (ddd, J = 14.3, 7.7, 1.5 Hz, 1H), 7.10 (tdd, J = 7.6, 2.4, 1.1 Hz, 1H), 6.61 (s, 1H), 3.93 (s, 3H), 3.87 (s, 5H), 3.11 (t, J = 6.1 Hz, 2H), 3.00 (t, J = 6.1 Hz, 2H), 2.68 (s, 3H), 1.84 (d, J = 13.1 Hz, 6H) | 468.0 $[M + H]^+$ |
| 24 | 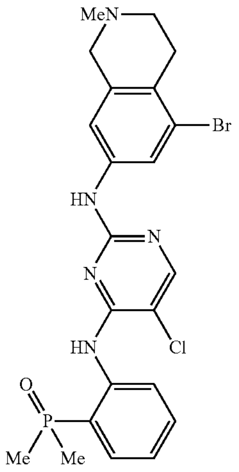 I-24 | 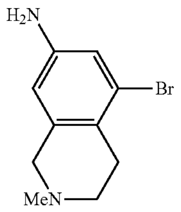 76 | ($CDCl_3$): δ 10.94 (s, 1H), 8.56 (dd, J = 8.3, 4.2 Hz, 1H), 8.10 (s, 1H), 7.72 (d, J = 2.2 Hz, 1H), 7.56 (td, J = 8.6, 1.5 Hz, 1H), 7.29 (ddd, J = 14.1, 7.8, 1.5 Hz, 1H), 7.13 (ddt, J = 7.6, 2.3, 1.0 Hz, 1H), 7.10 (s, 1H), 6.84 (s, 1H), 3.50 (s, 2H), 2.84 (t, J = 6.0 Hz, 2H), 2.71 (t, J = 6.0 Hz, 2H), 2.45 (s, 3H), 1.84 (d, J = 13.2 Hz, 6H). | 519.8 $[M + H]^+$ |

TABLE 1-continued

| Example Structure | | Aniline intermediate | $^1$H NMR (400 MHz) | ESI-MS m/z |
|---|---|---|---|---|
| 25 | 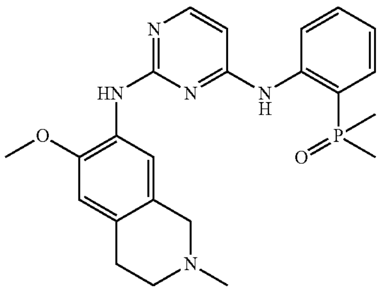 I-25 | 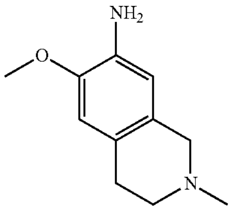 50 | ($CDCl_3$) δ 10.45 (s, 1H), 8.61 (ddd, J = 8.5, 4.4, 1.0 Hz, 1H), 8.11-8.03 (m, 2H), 7.51 (ddt, J = 8.7, 7.3, 1.4 Hz, 1H), 7.46 (s, 1H), 7.30-7.19 (m, 1H), 7.05 (tdd, J = 7.5, 2.4, 1.0 Hz, 1H), 6.60 (s, 1H), 6.15 (d, J = 5.7 Hz, 1H), 3.85 (s, 3H), 3.53-3.48 (m, 2H), 2.87 (t, J = 5.9 Hz, 2H), 2.68 (t, J = 6.0 Hz, 2H), 2.45 (s, 3H), 1.82 (d, J = 13.1 Hz, 6H) | 502.1 $[M + H]^+$ |
| 26 | 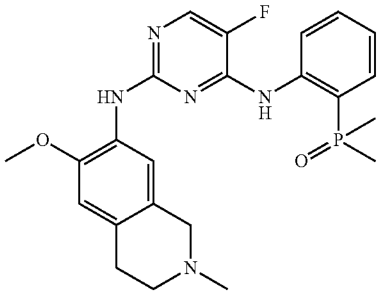 I-26 | 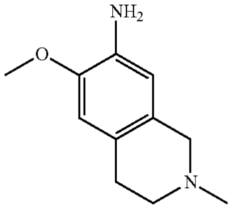 50 | ($CDCl_3$) δ 11.13 (s, 1H), 8.79-8.71 (m, 1H), 8.03-7.96 (m, 2H), 7.58-7.49 (m, 1H), 7.40 (s, 1H), 7.26 (ddd, J = 14.0, 7.8, 1.6 Hz, 1H), 7.10 (tdd, J = 7.6, 2.4, 1.1 Hz, 1H), 6.61 (s, 1H), 3.86 (s, 3H), 3.54-3.42 (m, 2H), 2.88 (t, J = 5.9 Hz, 2H), 2.73-2.60 (m, 2H), 2.45 (s, 3H), 1.84 (d, J = 13.2 Hz, 6H) | 456.1 $[M + H]^+$ |
| 27 | 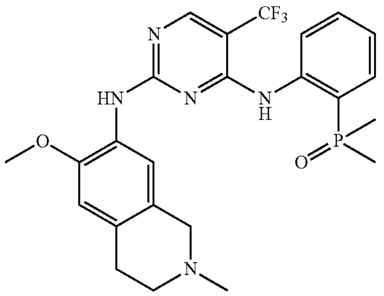 I-27 | 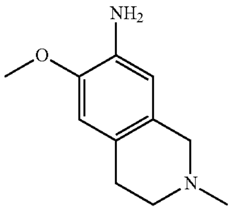 50 | ($CDCl_3$) δ 10.21 (s, 1H), 8.37 (d, J = 1.0 Hz, 1H), 8.27 (dd, 7 = 8.5, 4.3 Hz, 1H), 7.88 (s, 1H), 7.70 (s, 1H), 7.52 (ddt, J = 8.5, 7.3, 1.4 Hz, 1H), 7.35 (ddd, J = 13.7, 7.7, 1.6 Hz, 1H), 7.18 (tdd, J = 7.5, 2 4, 1.1 Hz, 1H), 6.60 (s, 1H), 3.85 (s, 3H), 3.29 (s, 2H), 2.86 (t, J = 5.9 Hz, 2H), 2.65 (t, J = 5.9 Hz, 2H), 2.42 (s, 3H), 1.81 (d, J = 13.2 Hz, 6H) | 506.2 $[M + H]^+$ |
| 28 | 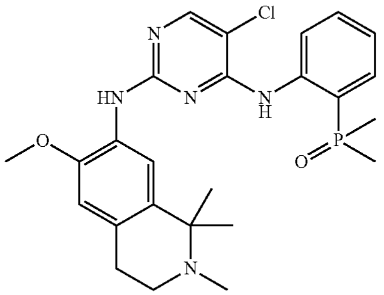 I-28 | 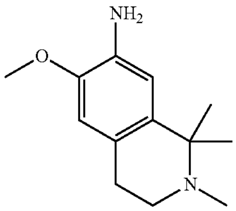 67 | ($CDCl_3$) δ 10.66 (s, 1H), 8.51 (dd, J = 8.4, 4.4 Hz, 1H), 8.16 (d, J = 17.8 Hz, 2H), 7.49 (dd, J = 8.7, 7.2 Hz, 1H), 7.35-7.22 (m, 2H), 7.10 (tdd, J = 7.6, 2.4, 1.1 Hz, 1H), 6.52 (s, 1H), 3.85 (s, 3H), 2.90-2.76 (m, 4H), 2.40 (s, 3H), 1.83 (d, J = 13.1 Hz, 6H), 1.27 (s, 6H) | 500.2 $[M + H]^+$ |

TABLE 1-continued

| Example | Structure | Aniline intermediate | $^1$H NMR (400 MHz) | ESI-MS m/z |
|---|---|---|---|---|
| 29 | 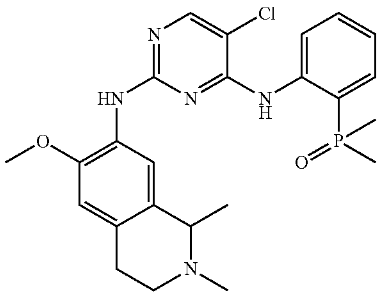 I-29 | 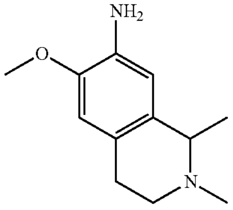 59 | ($CDCl_3$) δ 10.67 (s, 1H), 8.54-8.46 (m, 1H), 8.09 (d, J = 21.2 Hz, 2H), 7.52 (ddt, J = 8.5, 7.2, 1.5 Hz, 1H), 7.45 (s, 1H), 7.37-7.23 (m, 1H), 7.13 (tdd, J = 7.5, 2.4, 1.1 Hz, 1H), 6.56 (s, 1H), 3.85 (s, 3H), 3.47 (q, J = 6.6 Hz, 1H), 3.02 (ddd, J = 11.6, 6.4, 5.0 Hz, 1H), 2.89-2.68 (m, 2H), 2.69-2.52 (m, 1H), 2.47 (s, 3H), 1.89-1.77 (m, 6H), 1.28-1.13 (m, 3H) | 486.1 $[M + H]^+$ |
| 30 | 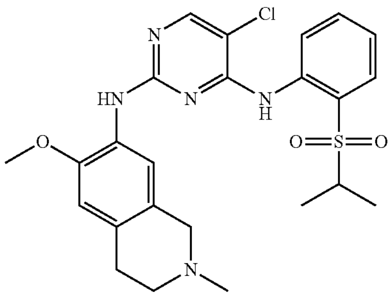 II-1 | 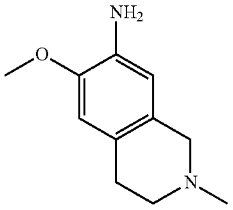 50 | ($CDCl_3$) δ 9.45 (s, 1H), 8.54-8.47 (m, 1H), 8.15 (s, 1H), 7.93 (dd, J = 8.0, 1.6 Hz, 1H), 7.88 (s, 1H), 7.66 (ddd, J = 8.6, 7.3, 1.7 Hz, 1H), 7.51 (s, 1H), 7.27 (ddd, J = 8.4, 6.6, 1.2 Hz, 1H), 6.61 (s, 1H), 3.86 (s, 3H), 3.37 (s, 2H), 3.24 (p, J = 6.8 Hz, 1H), 2.88 (dt, J = 11.7, 6.0 Hz, 2H), 2.66 (td, J = 5.9, 3.3 Hz, 2H), 2.44 (d, J = 3.3 Hz, 3H) | 502.1 $[M + H]^+$ |
| 31 | 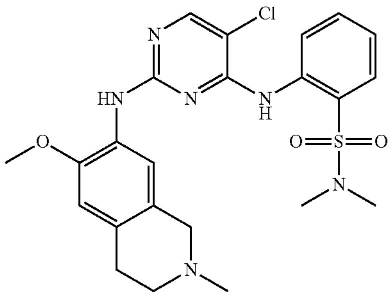 II-2 | 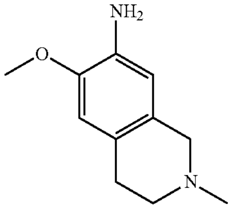 50 | ($CDCl_3$) δ 9.27 (s, 1H), 8.47 (dd, J = 8.4, 1.2 Hz, 1H), 8.13 (s, 1H), 7.89 (s, 1H), 7.89 (dd, J = 8.0, 1.6 Hz, 1H), 7.61 (ddd, J = 8.7, 7.3, 1.6 Hz, 1H), 7.51 (s, 1H), 7.26 (s, 1H), 6.60 (s, 1H), 3.86 (s, 3H), 3.37 (s, 2H), 2.87 (t, J = 5.9 Hz, 2H), 2.73 (s, 6H), 2.67 (t, J = 6.0 Hz, 2H), 2.44 (s, 3H) | 503.1 $[M + H]^+$ |
| 32 | 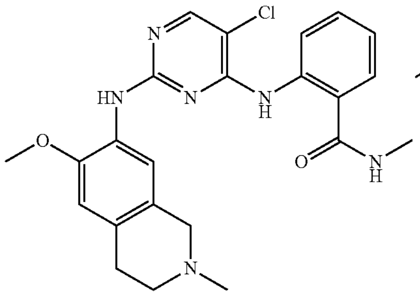 II-3 | 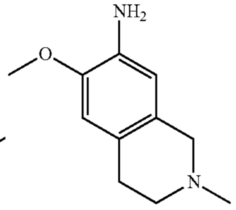 50 | ($CDCl_3$) δ 10.92 (s, 1H), 8.62 (dd, J = 8.8, 1.2 Hz, 1H), 8.10 (s, 1H), 7.98 (s, 1H), 7.49 (ddd, J = 7.9, 6.2, 4.9 Hz, 3H), 7.13-7.04 (m, 1H), 6.60 (s, 1H), 6.19 (s, 1H), 3.85 (s, 3H), 3.43 (s, 2H), 3.03 (d, J = 4.9 Hz, 3H), 2.87 (t, J = 5.9 Hz, 2H), 2.67 (t, J = 5.9 Hz, 2H), 2.43 (s, 3H) | 453.2 $[M + H]^+$ |

TABLE 1-continued

| Example | Structure | Aniline intermediate | $^1$H NMR (400 MHz) | ESI-MS m/z |
|---|---|---|---|---|
| 33 | 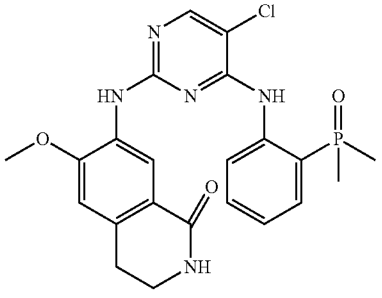 I-33 | 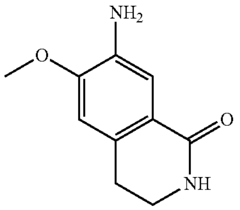 65 | ($CDCl_3$) δ 10.96-10.80 (m, 1H), 8.81 (s, 1H), 8.68 (dd, J = 4.5, 8.2 Hz, 1H), 8.13 (s, 1H), 7.65-7.47 (m, 1H), 7.37 (s, 1H), 1.24 (ddd, J = 1.5, 7.7, 14.2 Hz, 1H), 7.12-7.03 (m, 1H), 6.81 (br s, 1H), 6.68 (s, 1H), 3.91 (s, 3H), 3.53 (dt, J = 2.8, 6.6 Hz, 2H), 2.93 (t, J = 6.5 Hz, 2H), 1.86-1.74 (m, 6H) | 472.0 $[M + H]^+$ |
| 34 | 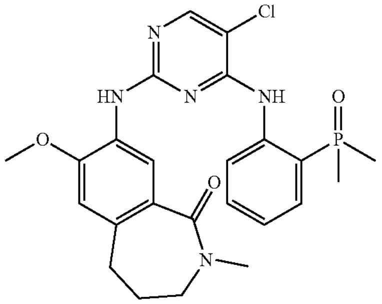 I-34 | 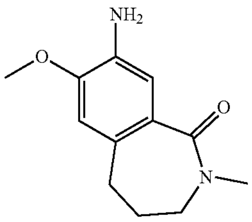 71 | ($CDCl_3$): δ10.74-10.98 (m, 1H), 8.60 (dd, J = 4.45, 8.22 Hz, 1H), 8.56 (s, 1H), 8.11 (s, 1H), 7.47-7.57 (m, 1H), 7.40 (s, 1H), 7.21-7.29 (m, 1H), 7.02-7.14 (m, 1H), 6.62 (s, 1H), 3.90 (s, 3H), 3.27 (t, J = 6.40 Hz, 2H), 3.19 (s, 3H), 2.74 (t, J = 7.09 Hz, 2H), 2.03 (t, J = 6.71 Hz, 2H), 1.81 (d, J = 13.18 Hz, 6H) | 500.1 $[M + H]^+$ |
| 35 | 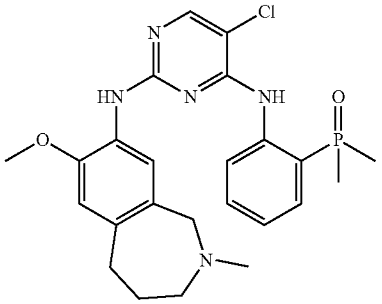 I-35 | 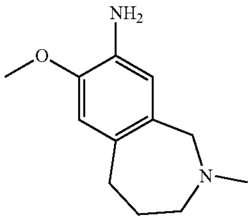 72 | ($CDCl_3$): δ 10.74-10.98 (m, 1H), 8.60 (dd, J = 4.45, 8.22 Hz, 1H), 8.56 (s, 1H), 8.11 (s, 1H), 7.47-7.57 (m, 1H), 7.40 (s, 1H), 7.21-7.29 (m, 1H), 7.02-7.14 (m, 1H), 6.62 (s, 1H), 3.90 (s, 3H), 3.27 (t, J = 6.40 Hz, 2H), 3.19 (s, 3H), 2.74 (t, J = 7.09 Hz, 2H), 2.03 (t, J = 6.71 Hz, 2H), 1.81 (d, J = 13.18 Hz, 6H) | 486.2 $[M + H]^+$ |
| 36 | 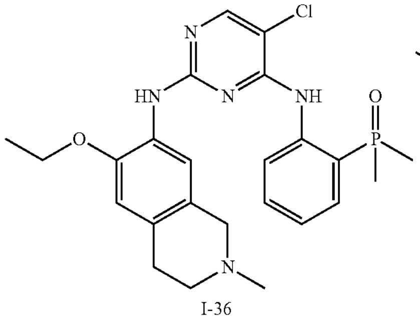 I-36 | 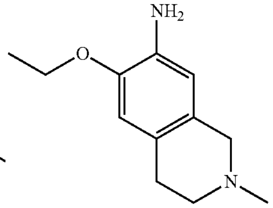 73 | ($CDCl_3$): δ 10.91-10.44 (m, 1H), 8.49 (dd, J = 4.4, 8.2 Hz, 1H), 8.03 (s, 1H), 7.89 (s, 1H), 7.51-7.40 (m, 2H), 7.24 (dt, J = 1.4, 7.0 Hz, 1H), 7.05 (ddt, J = 1.0, 2.3, 7.5 Hz, 1H), 6.52 (s, 1H), 4.00 (d, J = 7.0 Hz, 2H), 3.33 (s, 2H), 2.83-2.75 (m, 2H), 2.66-2.56 (m, 2H), 2.41-2.33 (m, 3H), 1.76 (d, J = 13.2 Hz, 6H), 1.37 (t, J = 7.0 Hz, 3H) | 486.2 $[M + H]^+$ |

Method B

Example 37: (2-((5-Chloro-2-((6-(trifluoromethyl)-1,2,3,4-tetrahydroisoquinolin-7-yl)amino)pyrimidin-4-yl)amino)phenyl)dimethylphosphine oxide (I-37)

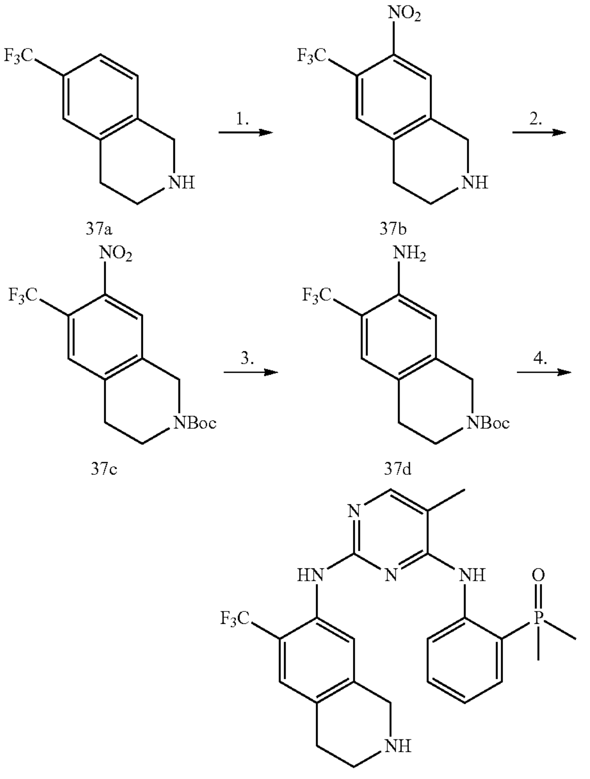

37a 37b 37c 37d I-37

Step 1. 7-Nitro-6-(trifluoromethyl)-1,2,3,4-tetrahydroisoquinoline (37b)

6-(Trifluoromethyl)-1,2,3,4-tetrahydroisoquinoline hydrochloride 37a (400 mg, 1.68 mmol, 1.0 eq) in 4 mL sulfuric acid was cooled to 0° C. Guanidine nitrate (205 mg, 1.68 mmol, 1.0 eq) was added while stirring, and the mixture was stirred from 0° C. to r.t. over 1 h. The reaction was then quenched with ice, basified with saturated aq. $K_2CO_3$ solution, and extracted with DCM. Organics were dried over anhydrous magnesium sulfate, filtered, and concentrated. The residue was purified by flash column chromatography on silica (0 to 10% MeOH:EtOAc) to afford 7-nitro-6-(trifluoromethyl)-1,2,3,4-tetrahydroisoquinoline 37b as a colorless solid.

Step 2. tert-Butyl 7-nitro-6-(trifluoromethyl)-3,4-dihydroisoquinoline-2(1H)-carboxylate (37c)

7-Nitro-6-(trifluoromethyl)-1,2,3,4-tetrahydroisoquinoline 37b (220 mg, 0.894 mmol, 1.0 eq), di-tert-butyl dicarbonate (254 mg, 1.16 mmol, 1.3 eq), and $Et_3N$ (0.16 mL, 1.16 mmol, 1.3 eq) were combined in 20 mL DCM and stirred at r.t. for 5 h. The solution was then washed with brine and organics were dried over anhydrous magnesium sulfate, filtered, and concentrated to afford tert-butyl 7-nitro-6-(trifluoromethyl)-3,4-dihydroisoquinoline-2(1H)-carboxylate 37c as a colorless oil.

Step 3. tert-Butyl 7-amino-6-(trifluoromethyl)-3,4-dihydroisoquinoline-2(1H)-carboxylate (37d)

tert-Butyl 7-nitro-6-(trifluoromethyl)-3,4-dihydroisoquinoline-2(1H)-carboxylate 37c (312 mg, 0.901 mmol, 1.0 eq) was dissolved in 5 mL EtOH. 10% Pd/C (19 mg, 0.180 mmol, 0.2 eq) was added and the mixture was stirred under balloon pressure of $H_2$ for 2 h. The reaction was then filtered through Celite and the filtrate was concentrated to afford tert-butyl 7-amino-6-(trifluoromethyl)-3,4-dihydroisoquinoline-2(1H)-carboxylate 37d as an off-white solid.

Step 4. (2-((5-Chloro-2-((6-(trifluoromethyl)-1,2,3,4-tetrahydroisoquinolin-7-yl)amino)pyrimidin-4-yl)amino)phenyl)dimethylphosphine oxide (I-37)

A flask was charged with tert-butyl 7-amino-6-(trifluoromethyl)-3,4-dihydroisoquinoline-2(1H)-carboxylate 37d (150 mg, 0.474 mmol, 1.0 eq), 2,5-dichloro-N-(2-dimethylphosphorylphenyl)pyrimidin-4-amine (165 mg, 0.522 mmol, 1.1 eq), $Pd(OAc)_2$ (11 mg, 0.047 mmol, 0.1 eq), Xantphos (55 mg, 0.095 mmol, 0.2 eq), and $Cs_2CO_3$ (232 mg, 0.711 mmol, 1.5 eq). The flask was evacuated and backfilled with $N_2$ three times, then 3 mL DMF was added. The reaction vessel was sealed and the reaction was stirred under $N_2$ for 24 h at 110° C. The reaction was then cooled to r.t., filtered through Celite, and the filtrate was concentrated. The residue was purified by flash column chromatography on silica (0 to 10% MeOH:EtOAc) to afford tert-butyl 7-((5-chloro-4-((2-(dimethylphosphoryl)phenyl)amino)pyrimidin-2-yl)amino)-6-(trifluoromethyl)-3,4-dihydroisoquinoline-2(1H)-carboxylate as a white foam.

This material was dissolved in 5 mL DCM and 2 mL TFA was then added while stirring. The reaction was stirred at r.t. for 2 h and then concentrated. The residue was partitioned between DCM and saturated aq. $NaHCO_3$. Organics were dried over anhydrous magnesium sulfate, filtered, and concentrated. The residue was purified by flash column chromatography on silica (0 to 20% MeOH:DCM) to afford the title compound 1-37 as a white solid. 96% yield. $^1H$ NMR (400 MHz, $CDCl_3$) δ 11.01 (s, 1H), 8.53 (ddd, J=8.6, 4.5, 1.0 Hz, 1H), 8.10 (s, 1H), 7.81 (s, 1H), 7.42 (ddt, J=8.6, 7.3, 1.4 Hz, 1H), 7.34 (s, 1H), 7.32-7.21 (m, 1H), 7.10 (tdd, J=7.5, 2.3, 1.0 Hz, 1H), 7.03 (s, 1H), 3.96 (s, 2H), 3.16 (t, J=5.9 Hz, 2H), 2.80 (t, J=5.9 Hz, 2H), 1.84 (d, J=13.1 Hz, 6H). ESI-MS m/z: 496.1 [M+H]+.

The compounds in Table 2 were synthesized according to Method B above using the corresponding starting secondary amines shown herein below.

TABLE 2
| Example | Structure | Starting secondary amine | $^1$H NMR (400 MHz, $CDCl_3$) | ESI-MS m/z |
|---|---|---|---|---|
| 38 | 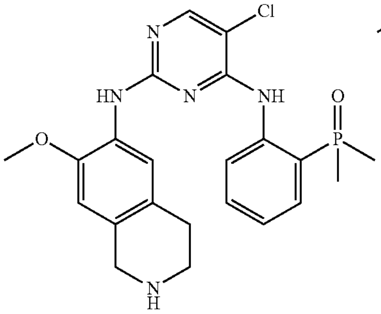 I-38 | 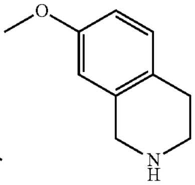 60a | δ 11.05-10.34 (m, 1H), 8.60 (s, 1H), 8.11 (s, 1H), 8.06-7.88 (m, 1H), 7.60-7.43 (m, 2H), 7.30 (dt, J = 1.5, 7.0 Hz, 1H), 7.19-7.02 (m, 1H), 6.51 (s, 1H), 3.97 (s, 2H), 3.85 (s, 3H), 3.11 (t, J = 6.0 Hz, 2H), 2.65 (t, J = 5.8 Hz, 2H), 1.84 (d, J = 13.2 Hz, 6H) | 457.1 $[M + H]^+$ |
| 39 | 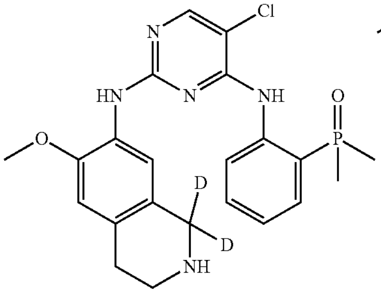 I-39 | 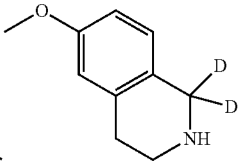 77 | δ 10.76 (s, 1H), 8.55 (dd, J = 4.3, 8.2 Hz, 1H), 8.11 (s, 1H), 7.97 (s, 1H), 7.61-7.44 (m, 2H), 7.30 (dt, J = 1.4, 7.0 Hz, 1H), 7.18-7.08 (m, 1H), 6.59 (s, 1H), 3.91-3.82 (m, 3H), 3.15 (t, J = 6.0 Hz, 2H), 2.76 (t, J = 5.9 Hz, 2H), 1.87-1.79 (m, 6H) | 460.1 $[M + H]^+$ |
| 40 | 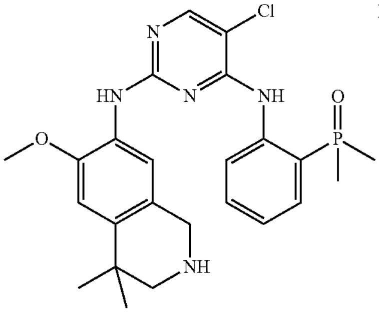 I-40 | 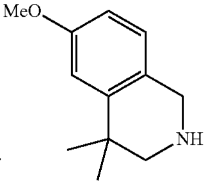 78 | δ 10.66 (s, 1H), 8.44 (ddd, J = 8.5, 4.4, 1.0 Hz, 1H), 8.01 (d, J = 3.5 Hz, 1H), 7.89 (d, J = 2.0 Hz, 1H), 7.53-7.34 (m, 2H), 7.28-7.19 (m, 1H), 7.10-7.02 (m, 1H), 6.71 (d, J = 2.4 Hz, 1H), 4.43 (br s, 1H), 3.85 (s, 2H), 3.81 (s, 3H), 2.85 (s, 2H), 1.75 (d, J = 13.2 Hz, 6H), 1.24 (s, 6H) | 486.1 $[M + H]^+$ |
| 41 | 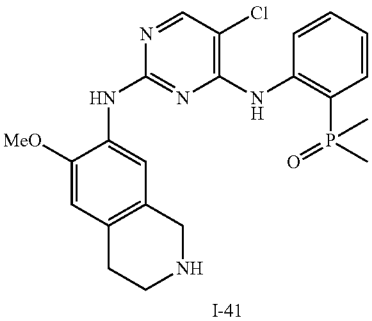 I-41 | 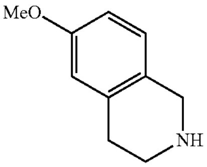 50a | δ 10.76 (s, 1H), 8.55 (dd, J = 4.3, 8.3 Hz, 1H), 8.11 (s, 1H), 7.96 (s, 1H), 7.60-7.46 (m, 2H), 7.36-7.27 (m, 1H), 7.20-7.08 (m, 1H), 6.58 (s, 1H), 3.90-3.77 (m, 5H), 3.13 (t, J = 6.0 Hz, 2H), 2.75 (t, J = 5.9 Hz, 2H), 1.83 (d, J = 13.2 Hz, 6H), 1.7 (br s, NH) | 457.0 $[M + H]^+$ |

Method C

Example 42: (2-((5-Chloro-2-((6-methoxy-2-(oxetan-3-yl)-1,2,3,4-tetrahydroisoquinolin-7-yl)amino)pyrimidin-4-yl)amino)phenyl)dimethylphosphine oxide (I-42)

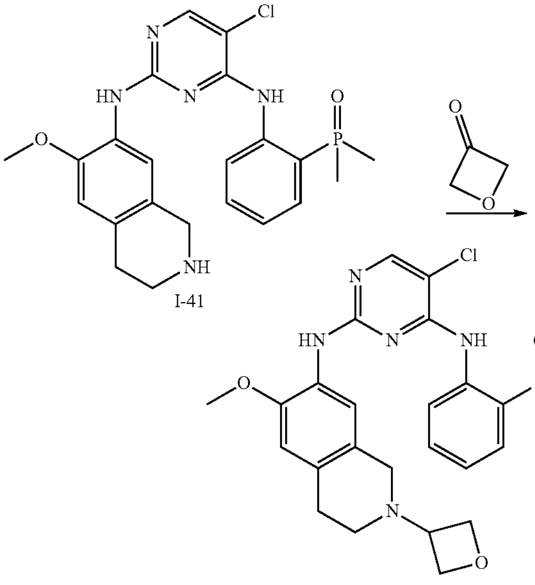

I-41

I-42

To (2-((5-Chloro-2-((6-methoxy-1,2,3,4-tetrahydroisoquinolin-7-yl)amino)pyrimidin-4-yl)amino)phenyl)dimethylphosphine oxide 1-41 (50 mg, 0.11 mmol) was added oxetan-3-one (36 mg, 0.5 mmol), 2 mL of MeOH and acetic acid (33 mg, 0.55 mmol) followed by careful addition of $NaBH_3CN$ (21 mg, 0.33 mmol) at about 0° C. After bubbling ceased, the reaction mixture was stirred at rt for 14 h. The resulting mixture was quenched with water and concentrated. The resulting residue was taken up in DCM and saturated aqueous sodium carbonate solution. The organic layer was separated, dried over anhydrous sodium sulfate, filtered, and concentrated in vacuo to afford the title compound I-42 as yellow solid. (71% yield). $^1H$ NMR (400 MHz, $CDCl_3$) δ 10.92-10.67 (m, 1H), 8.55 (dd, J=4.2, 8.2 Hz, 1H), 8.10 (s, 1H), 8.00 (s, 1H), 7.55-7.44 (m, 2H), 7.31 (dt, J=1.4, 7.0 Hz, 1H), 7.11 (ddt, J=0.9, 2.3, 7.5 Hz, 1H), 6.60 (s, 1H), 5.39 (s, 1H), 4.72 (d, J=6.5 Hz, 4H), 3.85 (s, 3H), 3.66 (t, J=6.5 Hz, 1H), 3.36 (s, 2H), 2.86 (t, J=5.8 Hz, 2H), 2.58 (t, J=5.9 Hz, 2H), 1.83 (d, J=13.2 Hz, 6H). ESI-MS m/z: 514.2 $[M+H]^+$.

The compounds in Table 3 were synthesized according to Method C above using the corresponding secondary amine intermediates and carbonyl reagents shown in Table 3 herein below.

TABLE 3

| Example | Structure | Amine intermediates | Carbonyl reagents | $^1H$ NMR (400 MHz, $CDCl_3$) | ESI-MS m/z |
|---|---|---|---|---|---|
| 43 | 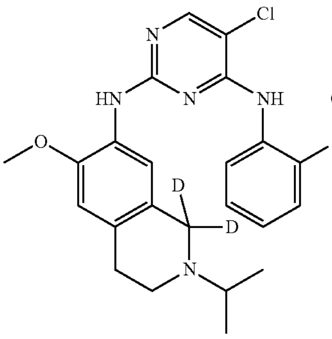 I-43 | 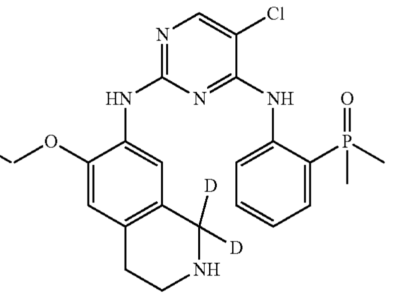 I-39 | acetone | δ 10.47-11.10 (m, 1H), 8.64 (dd, J = 4.45, 7.97 Hz, 1H), 8.11 (s, 1H), 7.68 (s, 1H), 7.45-7.57 (m, 1H), 7.34 (s, 1H), 7.22-7.31 (m, 1H), 7.09 (ddt, J = 1.00, 2.38, 7.47 Hz, 1H), 6.64-6.71 (m, 1H), 3.71-3.90 (m, 7H), 3.21-3.41 (m, 1H), 2.80-2.93 (m, 4H), 1.83 (d, J = 13.18 Hz, 6H), 1.07 (d, J = 6.27 Hz, 6H) | 502.2 $[M + H]^+$ |
| 44 | 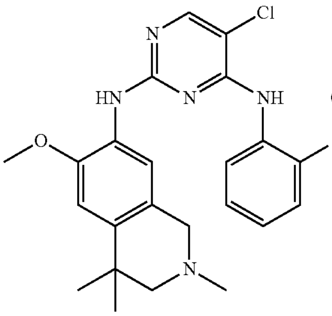 I-44 | 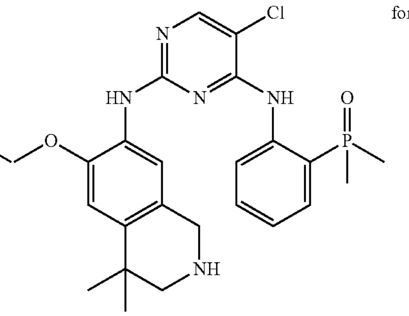 I-40 | formaldehyde | δ 10.75 (s, 1H), 8.55 (ddd, J = 8.5, 4.4, 1.0 Hz, 1H), 8.10 (s, 1H), 7.92 (s, 1H), 7.54 (ddt, J = 8.6, 7.2, 1.4 Hz, 1H), 7.47 (s, 1H), 7.35-7.27 (m, 1H), 7.14 (ddd, J = 7.5, 2.4, 1.1 Hz, 1H), 6.77 (s, 1H), 3.87 (s, 3H), 3.37 (s, 2H), 2.37 (d, J = 8.3 Hz, 5H), 1.83 (d, J = 13.2 Hz, 6H), 1.30 (s, 6H) | 500.2 $[M + H]^+$ |

TABLE 3-continued

| Example | Structure | Amine intermediates | Carbonyl reagents | $^1H$ NMR (400 MHz, $CDCl_3$) | ESI-MS m/z |
|---|---|---|---|---|---|
| 45 | 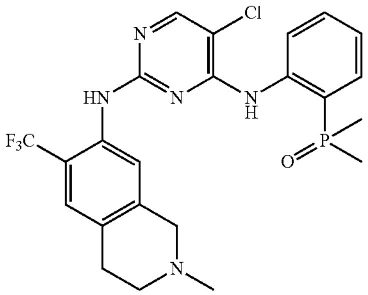 I-45 | 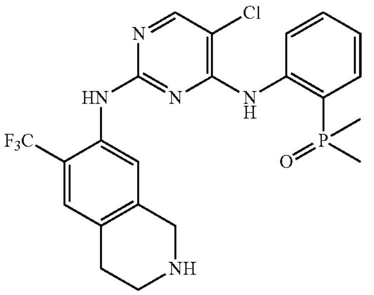 I-37 | formaldehyde | δ 11.02 (s, 1H), 8.54 (ddd, J = 8.6, 4.5, 1.0 Hz, 1H), 8.10 (s, 1H), 7.82 (s, 1H), 7.43 (ddt, J = 8.6, 7.3, 1.4 Hz, 1H), 7.36 (s, 1H), 7.32-7.21 (m, 1H), 7.10 (tdd, J = 7.5, 2.3, 1.1 Hz, 1H), 7.01 (s, 1H), 3.52 (s, 2H), 2.92 (t, J = 5.9 Hz, 2H), 2.71 (t, J = 5.9 Hz, 2H), 2.44 (s, 3H), 1.84 (d, J = 13.2 Hz, 6H) | 510.1 $[M + H]^+$ |

Method D

Example 46: (2-((2-((6-Methoxy-2-methyl-1,2,3,4-tetrahydroisoquinolin-7-yl)amino)-5-vinylpyrimidin-4-yl)amino)phenyl)dimethylphosphine oxide (I-46)

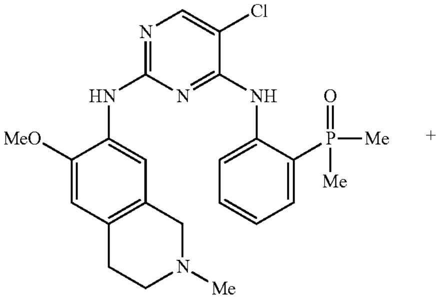

I-2

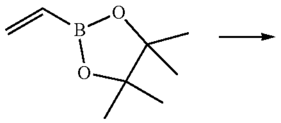

-continued

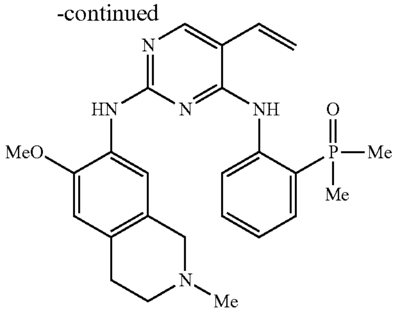

I-46

To (2-((5-Chloro-2-((6-methoxy-2-methyl-1,2,3,4-tetrahydroisoquinolin-7-yl)amino) pyrimidin-4-yl)amino)phenyl)dimethylphosphine oxide I-2 (136 mg, 0.288 mmol) was added potassium phosphate tribasic (61.2 mg, 0.288 mmol), palladium (II) acetate (6.47 mg, 0.0288 mmol), and SPhos (23.7 mg, 0.0576 mmol). The reaction flask was evacuated and purged with nitrogen three times before 1,4-dioxane (2.9 ml) and water (0.29 ml) were added. The reaction mixture was sparged briefly with nitrogen, and 4,4,5,5-tetramethyl-2-vinyl-1,3,2-dioxaborolane (58.7 μl, 0.346 mmol) was then added. The reaction mixture was stirred at 100° C. for 15 h. After cooling, the resulting mixture was diluted with dichloromethane (10 ml) and washed with water (5 ml). The aqueous wash was extracted with dichloromethane (3×3 ml) and the combined organic layers were dried over sodium sulfate, filtered, and concentrated in vacuo. This material was purified by column chromatography on silica gel (0 to 20% methanol in dichloromethane) to afford the title compound I-46 as a yellow solid. $^1H$ NMR (400 MHz, $CDCl_3$): δ 10.53 (s, 1H), 8.60 (dd, J=4.4, 8.3 Hz, 1H), 8.26 (s, 1H), 8.06 (s, 1H), 7.56-7.48 (m, 2H), 7.26 (ddd, J=1.6, 7.7, 14.1 Hz, 1H), 7.07 (ddt, J=1.0, 2.6, 7.6 Hz, 1H), 6.86 (dd, J=11.0, 17.3 Hz, 1H), 6.60 (s, 1H), 5.62 (dd, J=1.3, 17.2 Hz, 1H), 5.33 (dd, J=1.2, 11.0 Hz, 1H), 3.88-3.82 (m, 3H), 3.46 (s, 2H), 2.88 (t, J=5.9 Hz, 2H), 2.70 (t, J=5.9 Hz, 2H), 2.45 (s, 3H), 1.84 (s, 3H), 1.80 (s, 3H). ESI-MS m/z: 464.5 $[M+H]^+$.

Compound I-47 in Table 4 was synthesized as described in Method D above.

TABLE 4

| Example | Structure | Boronic acid | Aryl halide | $^1$H NMR (400 MHz) | ESI-MS m/z [M + H]$^+$ |
|---|---|---|---|---|---|
| 47 | 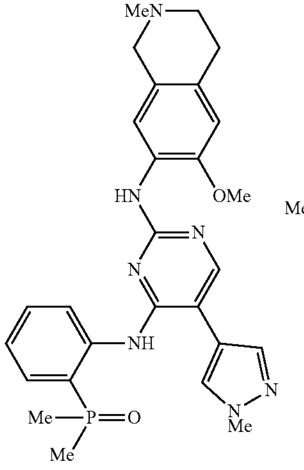 I-47 | 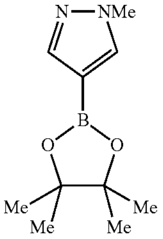 [SMILES: Cn1cc(B2OC(C)(C)C(C)(C)O2)cn1] | 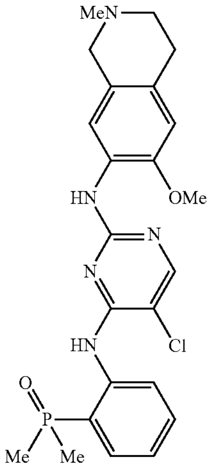 I-2 | ($CDCl_3$): δ 9.53 (s, 1H), 8.22 (dd, J = 8.6, 4.1 Hz, 1H), 8.13 (s, 1H), 8.00 (s, 1H), 7.85 (d, J = 0.9 Hz, 1H), 7.65 (d, J = 0.9 Hz, 1H), 7.58-7.50 (m, 2H), 7.32 (ddd, J = 13.5, 7.7, 1.6 Hz, 1H), 7.13 (tdd, J = 7.6, 2.5, 1.1 Hz, 1H), 6.58 (s, 1H), 3.97 (s, 3H), 3.85 (s, 3H), 3.31 (s, 2H), 2.85 (t, J = 5.9 Hz, 2H), 2.65 (t, J = 5.9 Hz, 2H), 2.43 (s, 3H), 1.75 (d, J = 13.1 Hz, 6H) | 518.5 |

Example 48: (2-((5-Ethyl-2-((6-methoxy-2-methyl-1,2,3,4-tetrahydroisoquinolin-7-yl)amino)pyrimidin-4-yl)amino)phenyl)dimethylphosphine oxide (I-48)

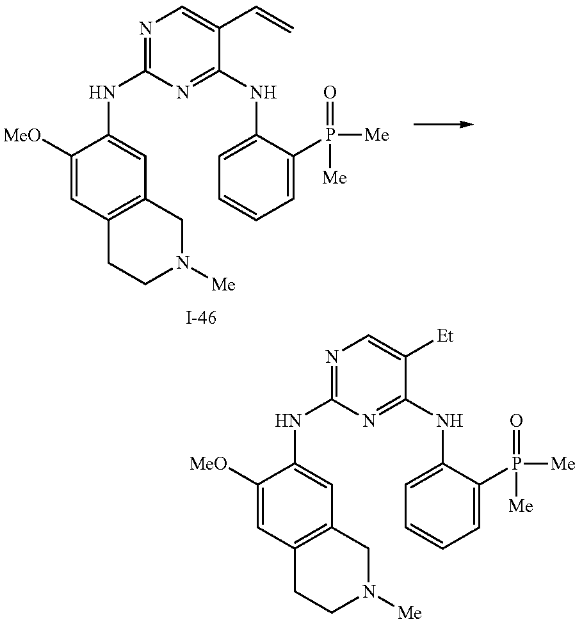

I-46

I-48

To a solution of (2-((2-((6-methoxy-2-methyl-1,2,3,4-tetrahydroisoquinolin-7-yl)amino)-5-vinylpyrimidin-4-yl) amino)phenyl)dimethylphosphine oxide 1-46 (33.0 mg, 0.0712 mmol) in methanol (1.0 ml) was added palladium on carbon (10.0 by wt %, 7.58 mg, 0.00712 mmol). The reaction flask was then purged with hydrogen, and stirred at rt for 2 h under a hydrogen atmosphere. The reaction was filtered through a Celite pad and the pad was washed with methanol. The filtrate was concentrated in vacuo and the obtained residue was purified by column chromatography on silica gel (eluting with 0 to 20% methanol in dichloromethane) to afford the title compound 1-48 as a yellow solid. $^1$H NMR (400 MHz, $CDCl_3$): δ 10.39 (br s, 1H), 8.57 (dd, J=4.3, 8.1 Hz, 1H), 8.21 (br s, 1H), 7.97 (s, 1H), 7.58-7.50 (m, 2H), 7.29 (ddd, J=1.4, 7.6, 14.0 Hz, 1H), 7.14 (ddt, J=0.9, 2.4, 7.5 Hz, 1H), 6.63 (s, 1H), 3.94 (br. s, 2H), 3.89 (s, 3H), 3.24 (br s, 2H), 3.12 (br s, 2H), 2.78 (br s, 3H), 2.62 (q, J=7.5 Hz, 2H), 1.85 (s, 3H), 1.82 (s, 3H), 1.29 (t, J=7.5 Hz, 3H). ESI-MS m/z: 466.4 [M+H]$^+$.

Method E

Example 49: 6-Methoxy-2-methylisoindolin-5-amine (49)

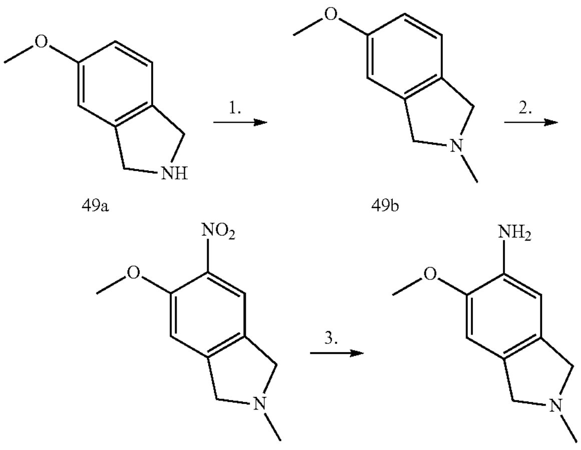

49a 49b 49c 49

Step 1. 5-Methoxy-2-methylisoindoline (49b)

To 5-Methoxyisoindoline 49a (500 mg, 3.15 mmol) was added MeOH (5 mL) and formaldehyde (1.5 mL, 37% in water). The reaction mixture was stirred at rt for 15 min and then cooled to 0° C. Sodium borohydride (400 mg, 10.05 mmol) was then lowly added and the resulting mixture was stirred at rt for 3 h. Upon reaction completion, the mixture was cooled to 0° C. and quenched by adding ice. The resulting mixture was stirred at rt for another 30 min and then concentrated concentrate. The resulting residue was taken up in DCM and water and the organic phase was separated. The aqueous phase was extracted with DCM (3×) and the combined organic phases were dried over anhydrous sodium sulfate, filtered, and concentrated under reduced pressure to afford 5-methoxy-2-methylisoindoline 49b. The product was taken on to the next step without further purification.

Step 2. 5-Methoxy-2-methyl-6-nitroisoindoline (49c)

To a stirred mixture of 5-methoxy-2-methylisoindoline 49b (550 mg g, 3.37 mmol) and concentrated sulfuric acid (10 mL) at 0° C. was added guanidine nitrate (350 mg, 2.87 mmol). The resulting mixture was stirred at 0° C. for 40 min and then quenched with ice and basified with a 4 N aqueous NaOH solution. The basified solution was extracted with DCM and the combined organic layers dried over magnesium sulfate, filtered, and concentrated in vacuo. The resulting residue was purified by flash chromatography on silica column eluting with 0 to 5% MeOH/DCM to afford 5-methoxy-2-methyl-6-nitroisoindoline 49c as a solid.

Step 3. 6-Methoxy-2-methylisoindolin-5-amine (49)

To a solution of 5-methoxy-2-methyl-6-nitroisoindoline (290 mg, 1.39 mmol) in acetone (5 mL) was added zinc powder (911 mg, 13.9 mmol) and 1 mL of saturated aqueous $NH_4Cl$ solution. The reaction mixture was vigorously stirred at rt for 1 h and the resulting solid was filtered off through a short pack of celite. The filtrate was collected, concentrated in vacuo, and then was taken up in DCM and diluted aqueous $NH_4OH$ solution. The organic layer was separated, dried over anhydrous sodium sulfate, filtered, concentrated in vacuo to give 6-methoxy-2-methylisoindolin-5-amine 49 as a solid.

The compounds in Table 5 were synthesized according to Method E described herein above. For the synthesis of Compounds 61 and 62, the nitration step (step 2) was not performed.

TABLE 5

| Example | Secondary or primary amine | Tertiary amine | Aniline intermediate |
|---|---|---|---|
| 50 | 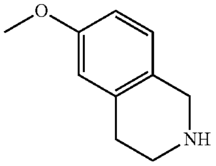 50a | 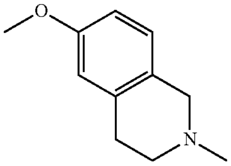 50b | 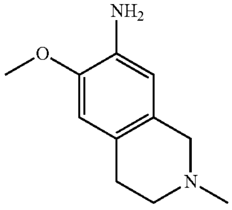 50 |
| 51 | 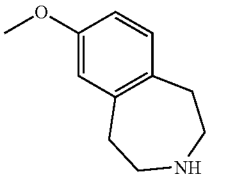 51a | 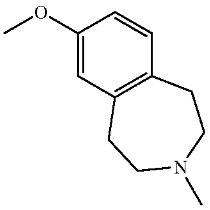 51b | 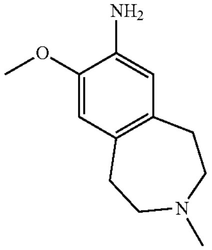 51 |
| 52 | 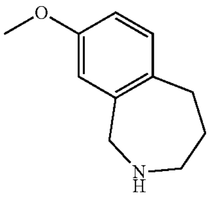 52a | 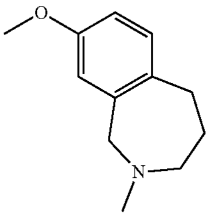 52b | 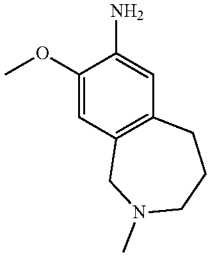 52 |

TABLE 5-continued
| Example | Secondary or primary amine | Tertiary amine | Aniline intermediate |
|---|---|---|---|
| 53 | 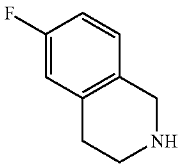 53a | 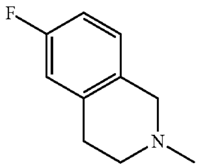 53b | 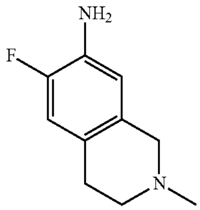 53 |
| 54 | 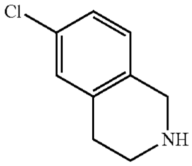 54a | 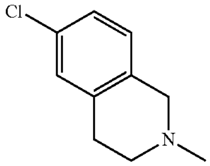 54b | 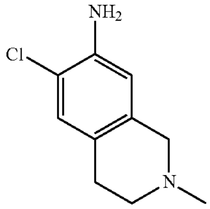 54 |
| 55 | 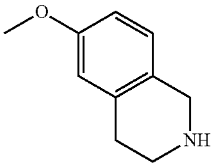 55a | 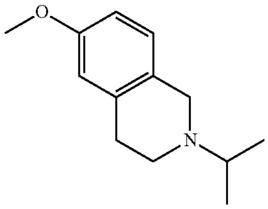 55b | 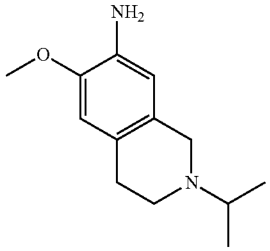 55 |
| 56 | 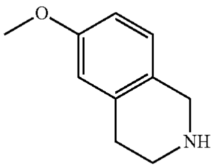 56a | 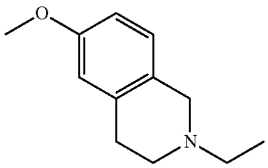 56b | 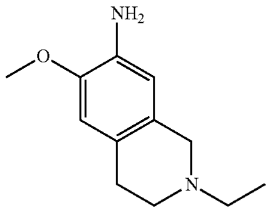 56 |
| 57 | 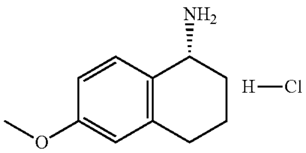 57a | 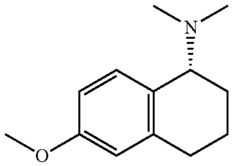 57b | 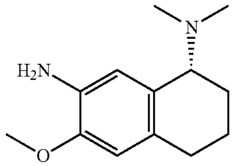 57 |
| 58 | 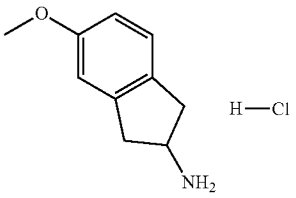 58a | 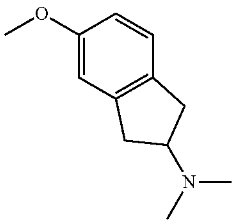 58b | 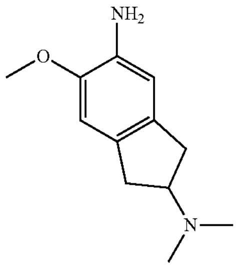 58 |

TABLE 5-continued

| Example | Secondary or primary amine | Tertiary amine | Aniline intermediate |
|---|---|---|---|
| 59 | 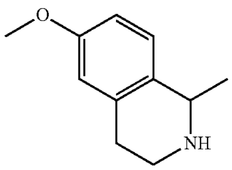 59a | 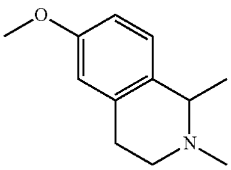 59b | 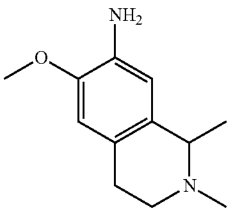 59 |
| 60 | 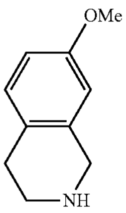 60a | 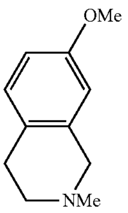 60b | 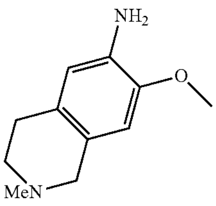 60 |
| 61 | 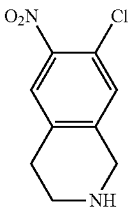 61a | 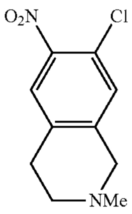 61b | 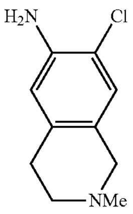 61 |
| 62 | 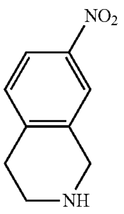 62a | 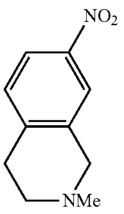 62b | 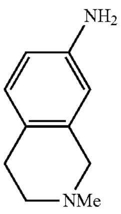 62 |

The compounds in Table 6 were synthesized in a 2-step sequence according to the procedures described in steps 2 and 3 of Example 49. In Example 66, two equivalents of guanidine nitrate were used in the nitration step.

TABLE 6

| Example | Starting Material | Aniline intermediate |
|---|---|---|
| 63 | 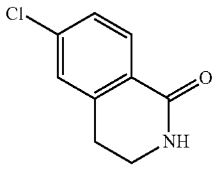 63a | 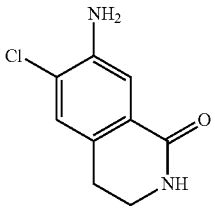 63 |

TABLE 6-continued
| Example | Starting Material | Aniline intermediate |
|---|---|---|
| 64 | 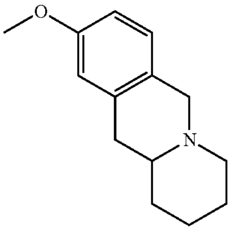<br>79 | 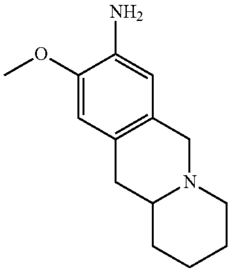<br>64 |
| 65 | 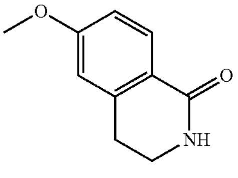<br>65a | 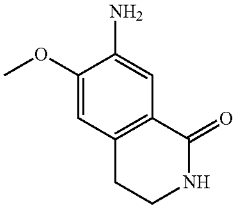<br>65 |
| 66 | 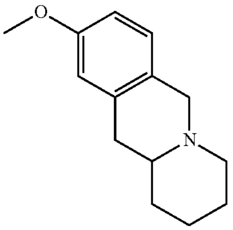<br>79 | 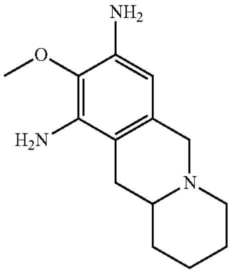<br>66 |
| 67 | 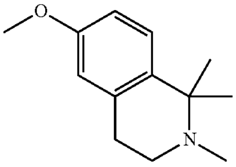<br>80 | 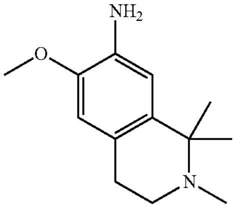<br>67 |
| 68 | 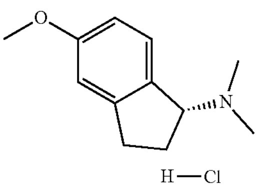<br>68a | 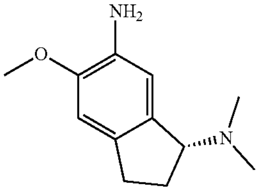<br>68 |

TABLE 6-continued

| Example | Starting Material | Aniline intermediate |
|---|---|---|
| 69 | 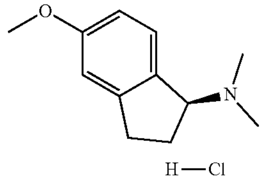 69a | 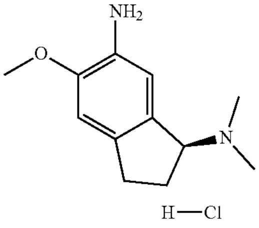 69 |
| 70 | 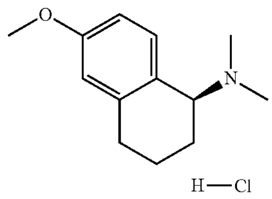 70a | 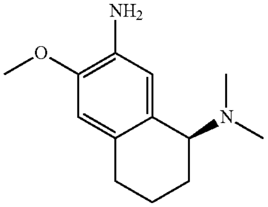 70 |

Examples 71 and 72: 8-amino-7-methoxy-2-methyl-2,3,4,5-tetrahydro-1H-benzo[c]azepin-1-one (71) and 7-methoxy-2-methyl-2,3,4,5-tetrahydro-1H-benzo[c]azepin-8-amine (72)

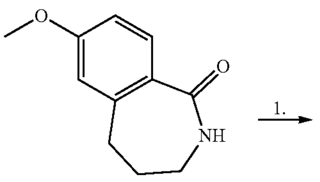

71a

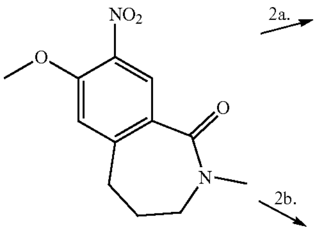

71b

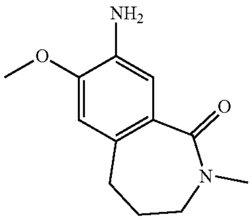

71

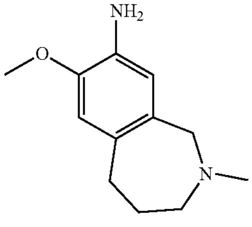

72

Step 1. 7-Methoxy-2-methyl-8-nitro-2,3,4,5-tetrahydro-1H-benzo[c]azepin-1-one (71b)

To a solution of 7-Methoxy-2,3,4,5-tetrahydro-1H-benzo[c]azepin-1-one 71a (2 g, 10.46 mmol) in THF (20 ml) cooled to 0° C. was added slowly NaH (5.44 g, 13.60 mmol). The resulting mixture was stirred at rt for 15 min and then again cooled to 0° C. MeI (2.23 g, 15.69 mmol) was then added dropwise and the mixture was stirred at rt for 1 h. The reaction mixture was cooled in an ice bath and quenched with ice water. Volatiles were removed under reduced pressure and the residue was partitioned between DCM and water. The organic layer was separated, dried over anhydrous sodium sulfate, filtered, and concentrated to afford 7-methoxy-2-methyl-2,3,4,5-tetrahydro-1H-benzo[c]azepin-1-one as a solid. The product was taken on to the next step without further purification.

7-Methoxy-2-methyl-2,3,4,5-tetrahydro-1H-benzo[c]azepin-1-one (2.10 g, 10.23 mmol) was dissolved in 10 mL of DCM. The mixture was cooled to 0° C. before concentrated $H_2SO_4$ (1.7 mL) and fuming nitric acid (1.8 mL) were added. The mixture was stirred at 0° C. for 1 h, and then warmed to rt and stirred at rt for another 2 h. The resulting mixture was then quenched with ice and concentrated under reduced pressure. The resulting residue was purified by flash chromatography on silica gel column eluting with 0 to 100% EtOAc to afford 7-methoxy-2-methyl-8-nitro-2,3,4,5-tetrahydro-1H-benzo[c]azepin-1-one 71b as a solid.

Step 2a. 8-Amino-7-methoxy-2-methyl-2,3,4,5-tetrahydro-1H-benzo[c]azepin-1-one (71)

7-Methoxy-2-methyl-8-nitro-2,3,4,5-tetrahydro-1H-benzo[c]azepin-1-one (100 mg, 0.4 mmol) 71b was combined with 2 mL of acetone followed by addition of zinc powder (226 mg, 4 mmol) and 0.5 mL of saturated aqueous $NH_4Cl$ solution. The mixture was vigorously stirred at rt for 1 h. Solid was filtered off through a short pack of celite. The filtrate was collected, concentrated and then was taken up in DCM and diluted aqueous $NH_4OH$ solution. The organic layer was separated, dried over anhydrous sodium sulfate, concentrated to give 8-amino-7-methoxy-2-methyl-2,3,4,5-tetrahydro-1H-benzo[c]azepin-1-one 71.

Step 2b. 7-Methoxy-2-methyl-2,3,4,5-tetrahydro-1H-benzo[c]azepin-8-amine (72)

To a solution of 7-methoxy-2-methyl-8-nitro-2,3,4,5-tetrahydro-1H-benzo[c]azepin-1-one (115 mg, 0.46 mmol) 71b in THF (5 mL) was added borane tetrahydrofuran complex (1.0 M, 3 mL). The resulting mixture was stirred under reflux for 14 h and then quenched with the slow addition of MeOH at rt and stirred under reflux for 2 h. Volatiles were removed under reduced pressure and the residue was purified by flash chromatography on silica gel eluting with 0 to 10% MeOH/DCM to afford 7-methoxy-2-methyl-8-nitro-2,3,4,5-tetrahydro-1H-benzo[c]azepine as oil. Reduction of nitro intermediate, 7-methoxy-2-methyl-8-nitro-2,3,4,5-tetrahydro-1H-benzo[c]azepine, under standard $Zn/NH_4Cl$ reduction conditions as described in step 2a afforded aniline 72.

Example 73: 6-Ethoxy-2-methyl-1,2,3,4-tetrahydroisoquinolin-7-amine (73)

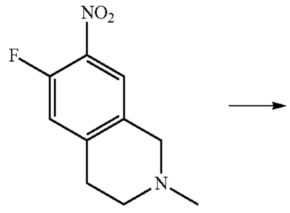

53c

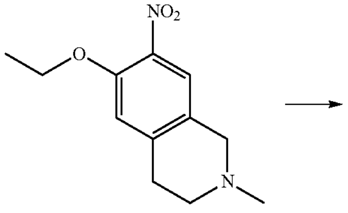

73a

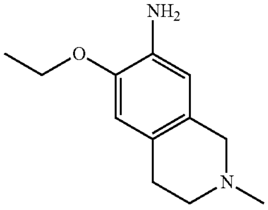

73

To a solution of 6-fluoro-2-methyl-7-nitro-1,2,3,4-tetrahydroisoquinoline (53c) (270 mg, 1.28 mmol) in EtOH (5 mL) was added potassium tert-butoxide (173 mg, 1.54 mmol). The mixture was stirred at 85° C. for 3 h and then cooled to rt and quenched with ice water. The resulting mixture was stirred at rt for another 15 min. The resulting solid was collected by filtration, washed with acetone, and then dried under vacuum to afford 6-ethoxy-2-methyl-7-nitro-1,2,3,4-tetrahydroisoquinoline 73a as a solid. Nitro intermediate 73a was directly reduced without purification under standard $Zn/NH_4Cl$ conditions to afford aniline 73.

Example 74: 2-Methyl-6-vinyl-1,2,3,4-tetrahydroisoquinolin-7-amine (74)

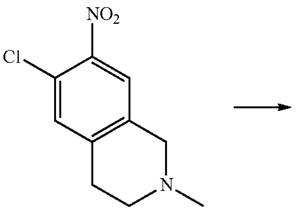

54c

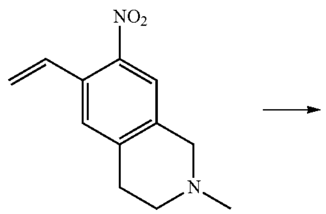

74a

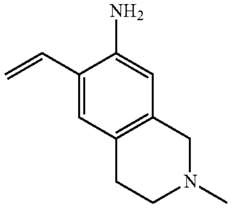

74

6-Chloro-2-methyl-7-nitro-3,4-dihydro-1H-isoquinoline (54c) (200 mg, 0.882 mmol), 4,4,5,5-tetramethyl-2-vinyl-1,3,2-dioxaborolane (204 mg, 1.32 mmol), palladium (II) acetate (9.9 mg, 0.0442 mmol), SPhos (36.2 mg, 0.0882 mmol) and potassium phosphate (562 mg, 2.65 mmol) were combined in a 5 mL microwave vial and then dioxane (2.0 mL) and water (0.2 mL) were added. The reaction mixture was flushed with argon, sealed, and heated under microwave irradiation at 125° C. for 30 minutes. The resulting mixture was cooled to room temperature and diluted with EtOAc and water. The organic layer was separated and concentrated directly onto celite for purification by silica gel eluting with a 0 to 5% MeOH in DCM gradient to afford 2-methyl-7-nitro-6-vinyl-3,4-dihydro-1H-isoquinoline 74a as a yellow solid in 72% yield. Nitro intermediate 74a was reduced under standard $Zn/NH_4Cl$ conditions to afford aniline 74.

Example 75: 6-Ethyl-2-methyl-3,4-dihydro-1H-isoquinolin-7-amine (75)

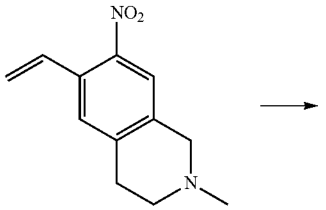

74a

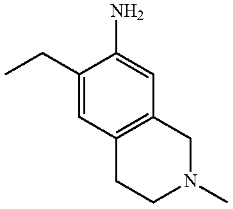

75

To a solution of 2-methyl-7-nitro-6-vinyl-3,4-dihydro-1H-isoquinoline 74a (70 mg, 0.321 mmol) in 2 mL EtOH and 0.1 mL 37% aqueous HCl was added 10% Pd/C, (wet basis, 8.24 mg, 2 mol %). The reaction was stirred at room temperature under 100 PSI of hydrogen overnight. The reaction mixture was brought to normal pressure, flushed with nitrogen, and then filtered over a pad of celite which was washed with EtOH. The filtrate was concentrated in vacuo to afford the product (75) as an off white foam in quantitative yield.

Example 76: 8-Bromo-2-methyl-1,2,3,4-tetrahydroisoquinolin-6-amine (76)

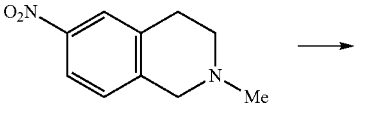

76a

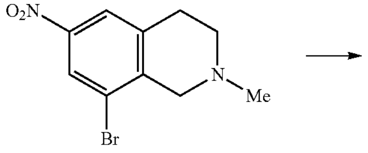

76b

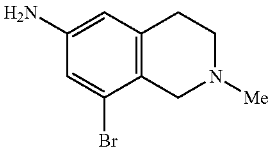

76

A solution of 2-methyl-7-nitro-3,4-dihydro-1H-isoquinoline 76a (500.0 mg, 2.60 mmol) in neat trifluoromethanesulfonic acid (6 mL) was cooled to 0° C. and N-bromosuccinimide (926 mg, 5.20 mmol) was added. The reaction was heated to 60° C. and stirred for 19 h. More N-bromosuccinimide (926 mg) was then added and the reaction mixture was stirred an additional 5 h at 60° C. The resulting mixture was poured into ice (~50 mL) and stirred until homogeneous. The mixture was diluted with 10% (v/v) aqueous sodium thiosulfate (20 mL), stirred at rt for 5 min and then treated with 4 M aq. NaOH until the pH of the solution was >10. The resulting mixture was extracted with dichloromethane (4×20 mL) and the combined organic layers were washed with 10% aq. $Na_2S_2O_3$ (20 mL), saturated aq. $NaHCO_3$ (2×20 mL), and brine (2×20 mL), dried over sodium sulfate, filtered, and concentrated in vacuo. The product was purified by preparative HPLC (5 μm XSelect CSH C18 column, 19 mm×100 mm, eluting with 5% to 30% $ACN/H_2O$ buffered with 0.1% formic acid) to afford 8-bromo-2-methyl-6-nitro-1,2,3,4-tetrahydroisoquinoline 76b as a yellow solid. Nitro intermediate 76b was reduced under standard $Zn/NH_4Cl$ condition to afford aniline 76.

Example 77: 6-Methoxy-1,2,3,4-tetrahydroisoquinoline-1,1-$d_2$ (77)

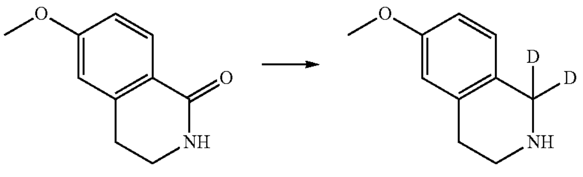

65a 77

To a solution of 6-methoxy-3,4-dihydroisoquinolin-1(2H)-one 65a (1.0 g, 5.64 mmol) in THF (10 mL) at 0° C. was slowly added $LiAlD_4$ and the reaction mixture was stirred at 0° C. until bubbling ceased. The resulting mixture was then stirred under reflux until no starting material was left (approximately 3 h). The reaction mixture was cooled to 0° C. and quenched with sequential addition of 0.4 mL of $H_2O$, 0.4 mL of 15% aqueous NaOH solution, and 1.2 mL of $H_2O$. After further stirring at rt for 30 min, the resulting solids were filtered off through celite and the filtrate was concentrated under reduced pressure. The resulting residue was partitioned between water and DCM and the organic layer was dried over anhydrous sodium sulfate, filtered and concentrated to give 6-methoxy-1,2,3,4-tetrahydroisoquinoline-1,1-$d_2$ 77 as an oil.

Method F

Example 78: 6-Methoxy-4,4-dimethyl-1,2,3,4-tetrahydroisoquinoline (78)

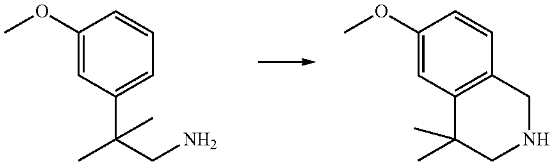

78a 78

To a mixture of 2-(3-methoxyphenyl)-2-methylpropan-1-amine 78a (1 g, 5.58 mmol) and formic acid (2.8 mL) at 0° C. was added paraformaldehyde (168 mg, 5.59 mmol) and the reaction mixture was stirred at 50° C. for 14 h. The resulting mixture was cooled to rt, diluted with water and extracted with DCM. The aqueous phase was separated, basified with 4 N NaOH solution, and extracted with DCM (5×). The combined organics were dried over anhydrous sodium sulfate, filtered, and concentrated to afford 2-(3-methoxyphenyl)-2-methylpropan-1-amine 78 as an oil.

Compound 79 in Table 7 was synthesized as described in Method F above using amine 79a shown herein below.

TABLE 7

| Example | Staring amine reagent | Tertiary amine intermediate |
|---|---|---|
| 79 | 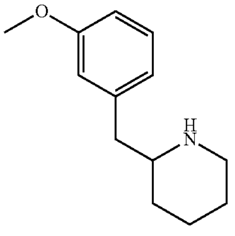 79a | 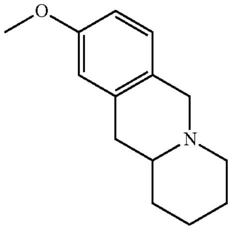 79 |

Example 80: 6-Methoxy-1,1,2-trimethyl-1,2,3,4-tetrahydroisoquinoline (80)

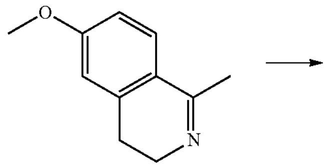

80a

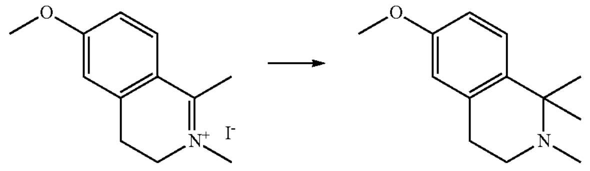

80b 80

To a solution of 6-methoxy-1-methyl-3,4-dihydroisoquinoline 80a (840 mg, 4.79 mmol, 1.0 eq) in acetone (20 mL) was added MeI (0.33 mL, 5.27 mmol, 1.1 eq) with stirring. The reaction mixture was stirred overnight, and then concentrated under vacuum to afford 6-methoxy-1,2-dimethyl-3,4-dihydroisoquinolin-2-ium iodide 80b as a yellow powder. 6-Methoxy-1,2-dimethyl-3,4-dihydroisoquinolin-2-ium iodide 80b (800 mg, 2.52 mmol, 1.0 eq) was suspended in 8 mL THF and cooled to −70° C. using a dry ice/acetone bath. 3 M methyl magnesium bromide in $Et_2O$ (2.52 mL, 7.57 mmol, 3.0 eq) was added under $N_2$ while stirring. After 1 h, the reaction mixture was gradually warmed to r.t. and stirred for 2-3 days. The mixture was then cooled to 0° C. and carefully quenched with water. The resulting mixture was extracted with EtOAc, and the combined organic layers were dried over anhydrous magnesium sulfate, filtered, and concentrated to afford 6-methoxy-1,1,2-trimethyl-1,2,3,4-tetrahydroisoquinoline 80 as an orange oil.

Biochemical Assays

Example 81: HPK1 Assay

The enzymatic activity of Wild Type HPK1 (MAP4K1) Kinase was measured in the presence or absence of an inhibitor compound of the present disclosure by preparation of a reaction mixture containing a fluorescein tagged peptide (2 micromolar final concentration), ATP (Adenosine Triphosphate, 500 micromolar final concentration) and Wild Type kinase (6 nM final concentration) in a buffer system comprising 50 mM HEPES (Buffer), 3 mM $MgCl_2$, 5% w/v Trehalose, 0.01% Brij 35 (Detergent), 0.1% Pluronic F127 (Surfactant), 0.1 mM EDTA (Ethylenediaminetetraacetic acid), 0.1 mM EGTA (ethylene glycol-bis(β-aminoethyl ether)-N,N,N',N'-tetraacetic acid) and 1 mM DTT (Dithiothreitol) and at a pH of 7.4. The reactions were quenched by the addition of EDTA to a final concentration of 25 mM. A Caliper EZ reader was used to measure the extent of substrate to product conversion.

The peptide substrate used in the HPK1 assay was designed based on the amino acid sequence surrounding serine residue 376 of SLP76-Lymphocyte cytosolic protein 2 (a known intracellular substrate of HPK1). This sequence SSFPQSAsLPPYFSQ was modified as follows for use in Caliper assays of HPK1: the serine residues on either side of serine 376 were replaced with alanine, three lysine residues were added at the N-terminus and a fluorescein tag (FAM) was attached to the C-terminus to produce the sequence, FAM-FPQAAsLPPYFAKKK.

Table 8: HPK1 activity of compounds of the invention in the HPK1 assay. ++++ indicates an $IC_{50}$ of less than about 5 nM, +++ indicates an $IC_{50}$ between about 5 nM and about 10 nM, ++ indicates an $IC_{50}$ between about 10 nM and about 100 nM, and + indicates an $IC_{50}$ greater than about 100 nM and less than about 10 μM.

TABLE 8

| HPK1 Assay. | | |
|---|---|---|
| Example | Method of Synthesis | $IC_{50}$ |
| I-1 | A | ++ |
| I-2 | A | ++++ |
| I-3 | A | ++ |
| I-4 | A | ++ |
| I-5 | A | ++++ |
| I-6 | A | ++++ |
| I-7 | A | +++ |
| I-8 | A | +++ |
| I-9 | A | ++ |
| I-10 | A | ++++ |
| I-11 | A | ++++ |
| I-12 | A | ++++ |
| I-13 | A | ++ |
| I-14 | A | +++ |
| I-15 | A | + |
| I-16 | A | + |
| I-17 | A | ++ |
| I-18 | A | ++++ |
| I-19 | A | ++++ |
| I-20 | A | ++++ |
| I-21 | A | ++++ |
| I-22 | A | ++++ |
| I-23 | A | +++ |
| I-24 | A | ++++ |
| I-25 | A | + |
| I-26 | A | ++ |
| I-27 | A | +++ |
| I-28 | A | ++ |
| I-29 | A | ++++ |
| II-1 | A | ++++ |
| II-2 | A | ++++ |
| II-3 | A | +++ |
| I-33 | A | + |
| I-34 | A | + |
| I-35 | A | + |
| I-36 | A | ++ |
| I-37 | B | ++ |
| I-38 | B | ++++ |
| I-39 | B | ++++ |
| I-40 | B | ++++ |
| I-41 | B | ++++ |
| I-42 | C | ++ |
| I-43 | C | ++++ |
| I-44 | C | +++ |
| I-45 | C | + |
| I-46 | D | ++++ |
| I-47 | D | + |
| I-48 | — | +++ |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula I:

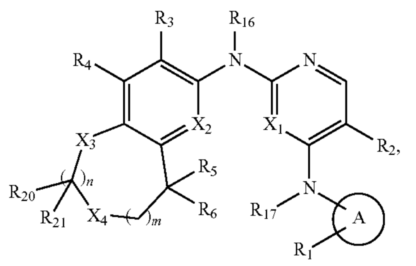

(I)

or a pharmaceutically acceptable salt, hydrate, solvate, stereoisomer, or tautomer thereof, wherein:

A is $C_{6-10}$ aryl or 5- or 6-membered heteroaryl;

$X_1$ is N;

$X_2$ is N or CH;

$X_3$ is $CR_7R_8$, NH, O, or $S(O)_q$;

$X_4$ is $NR_9$, O, $S(O)_q$ or $CR_{10}R_{11}$;

$R_1$ is $P(O)R_{12}R_{13}$;

$R_2$ is H, D, halogen, OH, $C_{1-6}$ alkyl, $C_{2-6}$ alkenyl, $C_{2-6}$ alkynyl, $C_{1-6}$ alkoxy, $C_{6-10}$ aryl, 5- to 7-membered heteroaryl, $C_{3-7}$ cycloalkyl, 3- to 7-membered heterocycloalkyl, CN, $NO_2$, $NR_{14}R_{15}$, $C(O)NR_{14}R_{15}$, $C(O)OR_{14}$, or $NR_{14}C(O)R_{12}$, wherein the $C_{1-6}$ alkyl, $C_{2-6}$ alkenyl, $C_{2-6}$ alkynyl, $C_{1-6}$ alkoxy, $C_{6-10}$ aryl, and 5- to 7-membered heteroaryl are optionally substituted with one or more substituents independently selected from the group consisting of $C_{1-6}$ alkyl, $C_{1-6}$ haloalkyl, halogen, $NR_{14}R_{15}$, CN, $NO_2$, and OH;

$R_3$ is H, D, halogen, OH, CN, $NO_2$, $C_{1-6}$ alkyl, $C_{2-6}$ alkenyl, $C_{2-6}$ alkynyl, $C_{1-6}$ alkoxy, $C(O)NR_{14}R_{15}$, $NR_{14}C(O)R_{12}$, or $NR_{14}R_{15}$ wherein the $C_{1-6}$ alkyl, $C_{2-6}$ alkenyl, $C_{2-6}$ alkynyl, and $C_{1-6}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH;

$R_4$ is H, D, halogen, OH, CN, $NO_2$, $C_{1-6}$ alkyl, $C_{2-6}$ alkenyl, $C_{2-6}$ alkynyl, $C_{1-6}$ alkoxy, $C(O)NR_{14}R_{15}$, $NR_{14}C(O)R_{12}$, or $NR_{14}R_{15}$ wherein the $C_{1-6}$ alkyl, $C_{2-6}$ alkenyl, $C_{2-6}$ alkynyl, $C_{1-6}$ alkoxy are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_3$ and $R_4$, together with the carbon atoms to which they are attached, form a $C_{5-7}$ cycloalkyl optionally substituted with one or more $R_{18}$; or $R_3$ and $R_4$, together with the carbon atoms to which they are attached, form a 5- to 7-membered heterocycloalkyl ring optionally substituted with one or more $R_{18}$; or $R_3$ and $R_4$, together with the carbon atoms to which they are attached, form a $C_{6-10}$ aryl ring optionally substituted with one or more $R_{18}$; or $R_3$ and $R_4$, together with the carbon atoms to which they are attached, form a 5- to 7-membered heteroaryl ring optionally substituted with one or more $R_{18}$;

$R_5$ and $R_6$ are each independently H, D, $C_{1-6}$ alkyl, $C_{2-6}$ alkenyl, $C_{2-6}$ alkynyl, $C_{3-7}$ cycloalkyl, 3- to 7-membered heterocycloalkyl, $NH_2$, $C_{1-6}$ alkylamino, or $C_{1-6}$ dialkylamino, wherein the $C_{1-6}$ alkyl, $C_{2-6}$ alkenyl, $C_{2-6}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_5$ and $R_6$ together with the carbon atom to which they are attached form an oxo group; or $R_5$ and $R_6$ together with the carbon atom to which they are attached form a $C_{3-7}$ cycloalkyl; or $R_5$ and $R_6$ together with the carbon atom to which they are attached form a 3- to 7-membered heterocycloalkyl ring;

$R_7$ and $R_8$ are each independently H, D, $C_{1-6}$ alkyl, $C_{2-6}$ alkenyl, $C_{2-6}$ alkynyl, $C_{3-7}$ cycloalkyl, 3- to 7-membered heterocycloalkyl, or $NH_2$, wherein the $C_{1-6}$ alkyl, $C_{2-6}$ alkenyl, $C_{2-6}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, halogen, $NR_{14}R_{15}$, CN, $NO_2$, and OH; or $R_7$ and $R_8$, together with the carbon atom to which they are attached, form a $C_{5-7}$ cycloalkyl ring optionally substituted with one or more $R_{19}$; or $R_7$ and $R_8$, together with the carbon atom to which they are attached, form a 5- to 7-membered heterocycloalkyl ring optionally substituted with one or more $R_{19}$; or $R_7$ and $R_8$, together with the carbon atom to which they are attached, form a $C_{6-10}$ aryl ring optionally substituted with one or more $R_{19}$; or $R_7$ and $R_8$, together with the carbon atom to which they are attached, form a 5- to 7-membered heteroaryl ring optionally substituted with one or more $R_{19}$;

$R_9$ is H, D, $C_{1-6}$ alkyl, $C_{2-6}$ alkenyl, $C_{2-6}$ alkynyl, —$C(O)R_{12}$; $C_{3-7}$ cycloalkyl, or 3- to 7-membered heterocycloalkyl, wherein the $C_{1-6}$ alkyl, $C_{2-6}$ alkenyl, $C_{2-6}$ alkynyl, $C_{3-7}$ cycloalkyl, and 3- to 7-membered heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH;

$R_{10}$ and $R_{11}$ are each independently H, D, $C_{1-6}$ alkyl, $C_{2-6}$ alkenyl, $C_{2-6}$ alkynyl, $C_{3-7}$ cycloalkyl, or 3- to 7-membered heterocycloalkyl, wherein $C_{1-6}$ alkyl, $C_{2-6}$ alkenyl, $C_{2-6}$ alkynyl, $C_{3-7}$ cycloalkyl, and heterocycloalkyl are optionally substituted with one or more substituents independently selected from the group consisting of $C_{1-6}$ alkyl, $C_{1-6}$ haloalkyl, $C_{1-6}$ hydroxyalkyl, halogen, $NR_{14}R_{15}$, CN, $NO_2$, and OH;

$R_{12}$ and $R_{13}$ are each independently $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-7}$ cycloalkyl, or 3- to 7-membered heterocycloalkyl; or $R_{12}$ and $R_{13}$ together with the phosphorus atom to which they are attached form a 3-8 membered heterocycloalkyl ring;

$R_{14}$ and $R_{15}$ are each independently H, D, $C_{1-6}$ alkyl, $C_{2-6}$ alkenyl, $C_{2-6}$ alkynyl, $C_{1-6}$ haloalkyl, $C_{3-7}$ cycloalkyl, or 5- to 7-membered heterocycloalkyl; or $R_{14}$ and $R_{15}$ together with the nitrogen atom to which they are attached form a 3- to 8-membered heterocycloalkyl ring optionally substituted with one or more substituents independently selected from the group consisting of $C_{1-6}$ alkyl, $C_{1-6}$ haloalkyl, $C_{1-6}$ hydroxyalkyl, halogen, $NR_{16}R_{17}$, CN, $NO_2$, and OH;

$R_{16}$ and $R_{17}$ are each independently H, D, or $C_{1-6}$ alkyl;

each $R_{18}$ is independently selected from the group consisting of halogen, OH, CN, $C_{1-6}$ alkyl, $C_{1-6}$ haloalkyl, $C_{2-6}$ alkenyl, $C_{2-6}$ alkynyl, $C_{1-6}$ alkoxy, haloalkoxy, $C(O)NR_{14}R_{15}$, $NR_{14}C(O)R_{12}$, and $NR_{14}R_{15}$;

each $R_{19}$ is independently selected from the group consisting of halogen, OH, CN, $C_{1-6}$ alkyl, $C_{1-6}$ haloalkyl, $C_{2-6}$ alkenyl, $C_{2-6}$ alkynyl, $C_{1-6}$ alkoxy, haloalkoxy, $C(O)NR_{14}R_{15}$, $NR_{14}C(O)R_{12}$, and $NR_{14}R_{15}$;

$R_{20}$ and $R_{21}$ are each independently H, D, or $C_{1-6}$ alkyl; or $R_{20}$ and $R_9$, when on adjacent atoms, together with the atoms to which they are attached form a 5- to 7-membered heterocycloalkyl ring;

each m and n is independently 0, 1, or 2, wherein the sum of m and n is 0, 1, or 2; and q is 0, 1, or 2.

2. The compound of claim 1, wherein $R_{12}$ and $R_{13}$ are $C_{1-6}$ alkyl.

3. The compound of claim 2, wherein $R_{12}$ and $R_{13}$ are each $—CH_3$.

4. The compound of claim 1, having Formula (Ia) or (Ib):

(Ia)

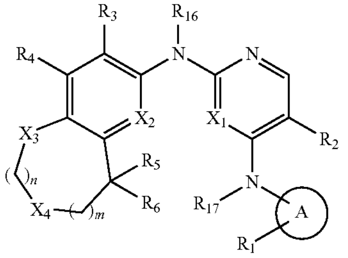

or (Ib)

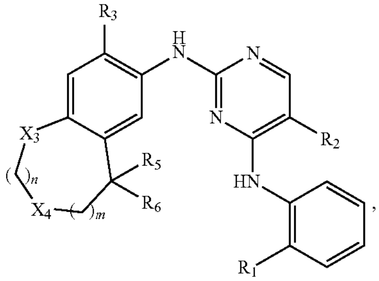

or a pharmaceutically acceptable salt, hydrate, solvate, stereoisomer, or tautomer thereof.

5. The compound of claim 1, having one of the following Formulae (Ic), (Id), or (Ie):

(Ic)

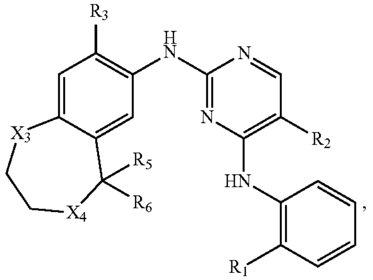

-continued (Id)

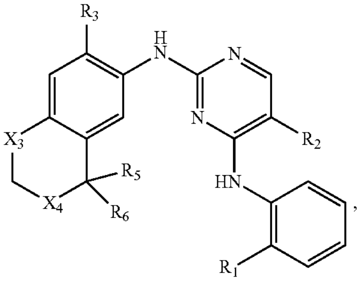

or (Ie)

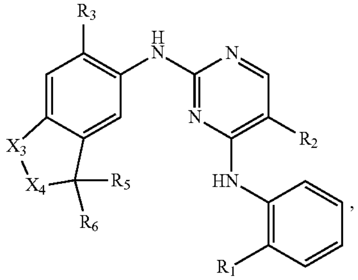

or a pharmaceutically acceptable salt, hydrate, solvate, stereoisomer, or tautomer thereof.

6. The compound of claim 1, having one of the following Formulae (If), (Ig), (Ih), or (Ii):

(If)

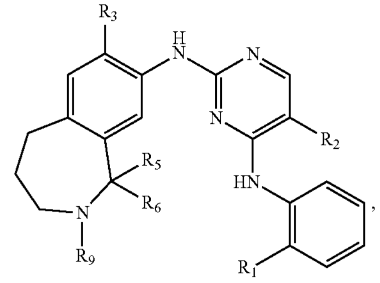

(Ig)

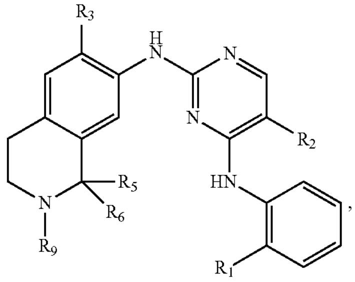

(Ih)

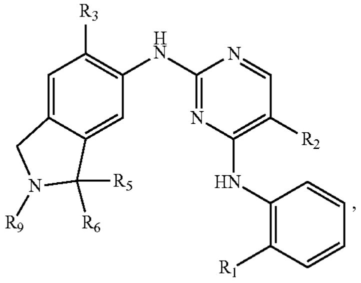

or

-continued (Ii)

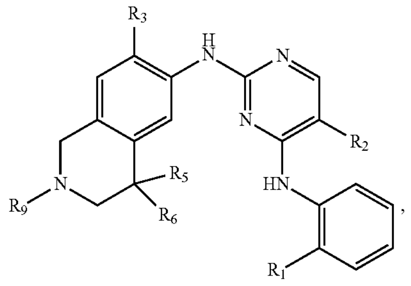

or a pharmaceutically acceptable salt, hydrate, solvate, stereoisomer, or tautomer thereof.

7. The compound of claim 4, wherein $R_9$ is H or $C_{1-6}$ alkyl.

8. The compound of claim 4, wherein $R_5$ is H and $R_6$ is H.

9. The compound of claim 4, wherein $R_3$ is methoxy and $R_2$ is selected from the group consisting of H, $C_{1-6}$ alkyl, $C_{1-6}$ haloalkyl, and $C_{2-6}$ alkenyl; or $R_2$ is chloro and $R_3$ is selected from the group consisting of $C_{1-6}$ alkyl, halogen, and $C_{1-6}$ alkoxy.

10. The compound of claim 9, wherein $R_5$ is H, $R_6$ is H, and $R_9$ is methyl.

11. A compound selected from the group consisting of:

(2-((5-Chloro-2-((6-methoxy-2-methylisoindolin-5-yl)amino)pyrimidin-4-yl)amino)phenyl)dimethylphosphine oxide;

(2-((5-chloro-2-((6-methoxy-2-methyl-1,2,3,4-tetrahydroisoquinolin-7-yl)amino)pyrimidin-4-yl)amino)phenyl)dimethylphosphine oxide;

(2-((5-chloro-2-((8-methoxy-3-methyl-2,3,4,5-tetrahydro-1H-benzo[d]azepin-7-yl)amino)pyrimidin-4-yl)amino)phenyl)dimethylphosphine oxide;

(2-((5-chloro-2-((8-methoxy-2-methyl-2,3,4,5-tetrahydro-1H-benzo[c]azepin-7-yl)amino)pyrimidin-4-yl)amino)phenyl)dimethylphosphine oxide;

(2-((5-chloro-2-((6-fluoro-2-methyl-1,2,3,4-tetrahydroisoquinolin-7-yl)amino)pyrimidin-4-yl)amino)phenyl)dimethylphosphine oxide;

5-chloro-$N^2$-(6-chloro-2-methyl-3,4-dihydro-1H-isoquinolin-7-yl)-$N^4$-(2-dimethylphosphorylphenyl)pyrimidine-2,4-diamine;

5-chloro-$N^4$-(2-dimethylphosphorylphenyl)-$N^2$-(6-ethyl-2-methyl-3,4-dihydro-1H-isoquinolin-7-yl)pyrimidine-2,4-diamine;

5-chloro-$N^4$-(2-dimethylphosphorylphenyl)-$N^2$-(2-methyl-6-vinyl-3,4-dihydro-1H-isoquinolin-7-yl)pyrimidine-2,4-diamine;

$N^8$-[5-chloro-4-(2-dimethylphosphorylanilino)pyrimidin-2-yl]-9-methoxy-2,3,4,6,11,11a-hexahydro-1H-benzo[b]quinolizine-8,10- diamine;

5-chloro-$N^4$-(2-dimethylphosphorylphenyl)-$N^2$-(9-methoxy-2,3,4,6,11,11a-hexahydro-1H-benzo[b]quinolizin-8-yl)pyrimidine-2,4-diamine;

(2-((5-chloro-2-((2-isopropyl-6-methoxy-1,2,3,4-tetrahydroisoquinolin-7-yl)amino)pyrimidin-4-yl)amino)phenyl)dimethylphosphine oxide;

(2-((5-chloro-2-((2-ethyl-6-methoxy-1,2,3,4-tetrahydroisoquinolin-7-yl)amino)pyrimidin-4-yl)amino)phenyl)dimethylphoshine oxide;

(R)-(2-((5-chloro-2-((8-(dimethylamino)-3-methoxy-5,6,7,8-tetrahydronaphthalen-2-yl)amino)pyrimidin-4-yl)amino)phenyl)dimethylphosphine oxide;

(R)-(2-((5-chloro-2-((3-(dimethylamino)-6-methoxy-2,3-dihydro-1H-inden-5-yl)amino)pyrimidin-4-yl)amino)phenyl)dimethylphosphine oxide;

(S)-(2-((5-chloro-2-((8-(dimethylamino)-3-methoxy-5,6,7,8-tetrahydronaphthalen-2-yl)amino)pyrimidin-4-yl)amino)phenyl)dimethylphosphine oxide;

(S)-(2-((5-chloro-2-((3-(dimethylamino)-6-methoxy-2,3-dihydro-1H-inden-5-yl)amino)pyrimidin-4-yl)amino)phenyl)dimethylphosphine oxide;

(2-((5-chloro-2-((2-(dimethylamino)-6-methoxy-2,3-dihydro-1H-inden-5-yl)amino)pyrimidin-4-yl)amino)phenyl)dimethylphosphine oxide;

(2-((5-chloro-2-((7-methoxy-2-methyl-1,2,3,4-tetrahydroisoquinolin-6-yl)amino)pyrimidin-4-yl)amino)phenyl)dimethylphosphine oxide;

(2-((5-chloro-2-((6-methoxy-2-methyl-1,2,3,4-tetrahydroisoquinolin-7-yl)amino)pyrimidin-4-yl)amino)phenyl)diethylphosphine oxide;

(2-((5-chloro-2-((6-chloro-2-methyl-1,2,3,4-tetrahydroisoquinolin-7-yl)amino)pyrimidin-4-yl)amino)phenyl)diethylphosphine oxide;

(2-((5-chloro-2-((7-chloro-2-methyl-1,2,3,4-tetrahydroisoquinolin-6-yl)amino)pyrimidin-4-yl)amino)phenyl)dimethylphosphine oxide;

(2-((5-bromo-2-((6-methoxy-2-methyl-1,2,3,4-tetrahydroisoquinolin-7-yl)amino)pyrimidin-4-yl)amino)phenyl)dimethylphosphine oxide;

(2-((5-methoxy-2-((6-methoxy-2-methyl-1,2,3,4-tetrahydroisoquinolin-7-yl)amino)pyrimidin-4-yl)amino)phenyl)dimethylphosphine oxide;

(2-((2-((5-bromo-2-methyl-1,2,3,4-tetrahydroisoquinolin-7-yl)amino)-5-chloropyrimidin-4-yl)amino)phenyl)dimethylphosphine oxide;

(2-((2-((6-methoxy-2-methyl-1,2,3,4-tetrahydroisoquinolin-7-yl)amino)pyrimidin-4-yl)amino)phenyl)dimethylphosphine oxide;

(2-((5-fluoro-2-((6-methoxy-2-methyl-1,2,3,4-tetrahydroisoquinolin-7-yl)amino)pyrimidin-4-yl)amino)phenyl)dimethylphosphine oxide;

(2-((2-((6-methoxy-2-methyl-1,2,3,4-tetrahydroisoquinolin-7-yl)amino)-5-(trifluoromethyl)pyrimidin-4-yl)amino)phenyl)dimethylphosphine oxide;

(2-((5-chloro-2-((6-methoxy-1,1,2-trimethyl-1,2,3,4-tetrahydroisoquinolin-7-yl)amino)pyrimidin-4-yl)amino)phenyl)dimethylphosphine oxide;

(2-((5-chloro-2-((6-methoxy-1,2-dimethyl-1,2,3,4-tetrahydroisoquinolin-7-yl)amino)pyrimidin-4-yl)amino)phenyl)dimethylphosphine oxide;

7-((5-chloro-4-((2-(dimethylphosphoryl)phenyl)amino)pyrimidin-2-yl)amino)-6-methoxy-3,4-dihydroisoquinolin-1(2H)-one;

8-((5-chloro-4-((2-(dimethylphosphoryl)phenyl)amino)pyrimidin-2-yl)amino)-7-methoxy-2-methyl-2,3,4,5-tetrahydro-1H-benzo[c]azepin-1-one;

(2-((5-chloro-2-((7-methoxy-2-methyl-2,3,4,5-tetrahydro-1H-benzo[c]azepin-8-yl)amino)pyrimidin-4-yl)amino)phenyl)dimethylphosphine oxide;

(2-((5-chloro-2-((6-ethoxy-2-methyl-1,2,3,4-tetrahydroisoquinolin-7-yl)amino)pyrimidin-4-yl)amino)phenyl)dimethylphosphine oxide;

(2-((5-Chloro-2-((6-(trifluoromethyl)-1,2,3,4-tetrahydroisoquinolin-7-yl)amino)pyrimidin-4-yl)amino)phenyl)dimethylphosphine oxide;

(2-((5-chloro-2-((7-methoxy-1,2,3,4-tetrahydroisoquinolin-6-yl)amino)pyrimidin-4-yl)amino)phenyl)dimethylphosphine oxide;

(2-((5-chloro-2-((6-methoxy-1,2,3,4-tetrahydroisoquinolin-7-yl-1,1-d2)amino)pyrimidin-4-yl)amino)phenyl)dimethyl-phosphine oxide;

(2-((5-chloro-2-((6-methoxy-4,4-dimethyl-1,2,3,4-tetrahydroisoquinolin-7-yl)amino)pyrimidin-4-yl)amino)phenyl)dimethylphosphine oxide;

(2-((5-chloro-2-((6-methoxy-1,2,3,4-tetrahydroisoquinolin-7-yl)amino)pyrimidin-4-yl)amino)phenyl)dimethylphosphine oxide;

(2-((5-Chloro-2-((6-methoxy-2-(oxetan-3-yl)-1,2,3,4-tetrahydroisoquinolin-7-yl)amino)pyrimidin-4-yl)amino)phenyl)dimethylphosphine oxide;

(2-((5-chloro-2-((2-isopropyl-6-methoxy-1,2,3,4-tetrahydroiso-quinolin-7-yl-1,1-d2)amino)pyrimidin-4-yl)amino)phenyl)- dimethylphosphine oxide;

(2-((5-chloro-2-((6-methoxy-2,4,4-trimethyl-1,2,3,4-tetrahydroisoquinolin-7-yl)amino)pyrimidin-4-yl)amino)phenyl)-dimethylphosphine oxide;

(2-((5-chloro-2-((2-methyl-6-(trifluoromethyl)-1,2,3,4-tetrahydroiso-quinolin-7-yl)amino)-pyrimidin-4-yl)-amino)phenyl)dimethylphosphine oxide;

(2-((2-((6-Methoxy-2-methyl-1,2,3,4-tetrahydroisoquinolin-7-yl)amino)-5-vinylpyrimidin-4-yl)amino)phenyl)dimethylphosphine oxide;

(2-((2-((6-methoxy-2-methyl-1,2,3,4-tetrahydroisoquinolin-7-yl)amino)-5-(1-methyl-1H-pyrazol-4-yl)pyrimidin-4-yl)amino)phenyl)dimethylphosphine oxide; and (2-((5-Ethyl-2-((6-methoxy-2-methyl-1,2,3,4-tetrahydroisoquinolin-7-yl)amino)pyrimidin-4-yl)amino)phenyl)dimethylphosphine oxide, or a pharmaceutically acceptable salt, hydrate, solvate, stereoisomer, or tautomer thereof.

12. A pharmaceutical composition comprising a compound of claim 1, or a pharmaceutically acceptable salt, hydrate, solvate, stereoisomer, or tautomer thereof, and a pharmaceutically acceptable diluent, excipient or carrier.

* * * * *